(12) United States Patent
Copeland

(10) Patent No.: US 10,076,556 B2
(45) Date of Patent: *Sep. 18, 2018

(54) METHODS FOR INHIBITING TUMOR GROWTH

(71) Applicant: Oxyrase, Inc., Mansfield, OH (US)

(72) Inventor: James C. Copeland, Mansfield, OH (US)

(73) Assignee: OXYRASE, INC., Mansfield, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,913

(22) Filed: Jan. 28, 2016

(65) Prior Publication Data

US 2016/0220646 A1   Aug. 4, 2016

Related U.S. Application Data

(60) Provisional application No. 62/109,136, filed on Jan. 29, 2015.

(51) Int. Cl.
  *A61K 35/74* (2015.01)
  *A61K 31/19* (2006.01)
  *A61K 38/43* (2006.01)
  *A61K 45/06* (2006.01)

(52) U.S. Cl.
  CPC .............. *A61K 38/43* (2013.01); *A61K 31/19* (2013.01); *A61K 35/74* (2013.01); *A61K 45/06* (2013.01); *Y02A 50/473* (2018.01); *Y02A 50/481* (2018.01)

(58) Field of Classification Search
  None
  See application file for complete search history.

(56) References Cited

U.S. PATENT DOCUMENTS

| | | |
|---|---|---|
| 4,476,224 A | 10/1984 | Adler |
| 4,744,985 A | 5/1988 | Tamai et al. |
| 4,996,073 A | 2/1991 | Copeland et al. |
| 5,240,853 A | 8/1993 | Copeland et al. |
| 5,432,083 A | 7/1995 | Copeland et al. |
| 6,190,657 B1 | 2/2001 | Pawelek et al. |
| 6,685,935 B1 | 2/2004 | Pawelek et al. |
| 7,344,710 B2 | 3/2008 | Dang et al. |
| 7,374,905 B2 | 5/2008 | Copeland et al. |
| 7,740,835 B2 | 6/2010 | Fujimori et al. |
| 8,007,782 B2 | 8/2011 | Dang et al. |
| 8,591,921 B2 | 11/2013 | Lee et al. |
| 8,613,917 B2 | 12/2013 | Dang et al. |
| 8,722,116 B2 | 5/2014 | Huang |
| 8,821,875 B2 | 9/2014 | Bauer |
| 2007/0141044 A1 | 6/2007 | Hirschman |
| 2009/0169591 A1 | 7/2009 | Kaul |
| 2010/0158952 A1* | 6/2010 | Goletz ............. C07K 16/3092 424/243.1 |

FOREIGN PATENT DOCUMENTS

WO   WO 2009111177 A2 *  9/2009 ............ A61K 35/74

OTHER PUBLICATIONS

Liu "Noninvasive Imaging of Infection after treatment with Tumor Homing Bacteria Using Chemical Exchange Transfer (CEST) MRI" Magnetic Resonance in Medicine 70 (2013) 1690-1698.*
Oxyrase "Oxyrase Enzyme: System Product Insert" Oxyrase Inc. Mansfield OH, Jan. 2011.*
Linnebacher "Lysates of *S. pyogenes* Serotype M49 Induce Pancreatic Tumor Growth Delay by Specific and Unspecific Antitumor Immune Responses" Journal of Immunotherapy, vol. 31, Issue 8, Oct. 2008.*
Chakrabarty, "Microorganisms and Cancer: Quest for a Therapy",. J. Bacteriol, 2003, vol. 185, No. 9, pp. 2683-2686.
Cummins et al., "Bacteria and Tumors: Causative agents or opportunistic inhabitants?", Infectioud Agents and Cancer, 2013, vol. 8, No. 11.
Dang et al., Combination bacteriolytic therapy for the treatment of experimental tumors, PNAS, Dec. 18, 2001, vol. 98, No. 26, pp. 15155-15160.
Hoffman, "Back to the Future: Are Tumor-Targeting Bacteria the Next-Generation Cancer Therapy?", Gene Therapy of Solid Cancers: Methods in Molecular Biology, 2015, vol. 1317, pp. 239-260.
Patyar et al., "Bacteria in cancer therapy: a novel experimental strategy", J. Biomed. Sci., 2010, vol. 17, No. 21.
Taniguchi et al., "Targeting solid tumors with non-pathogenic obligate anaerobic bacteria", Cancer Sci, Sep. 2010, vol. 101, No. 9, pp. 1925-1932.
Theys et al., "Specific targeting of cytosine deaminase to solid tumors by engineered Clostridium acetobutylicum", Cancer Gene Therapy, 2001, vol. 8, No. 4, pp. 294-297.
International Search Report and Written Opinion from PCT/US2016/015321 dated Mar. 31, 2016.
Dong et al., "Antioxidants, Oxyrase, and mitochondrial uncoupler 2,4-dinitrophenol improved postthaw survival of rhesus monkey sperm from ejaculates with low cryosurvival", Fertility and Sterility, Nov. 2010, vol. 94, No. 6, pp. 2359-2361.
Mazur Rt Al., "The enhancement of the ability of mouse sperm to survive freezing and thawing by the use of high concentrations of glycerol and the presence of an *Escherichia coli* membrane preparation (Oxyrase) to lower the oxygen concentration", Cryobiology, May 2000, vol. 40, No. 3, pp. 187-209.
Supplementary European Search Report for European Patent Application No. 16744089.0 dated Jul. 10, 2018.

* cited by examiner

*Primary Examiner* — Robert J Yamasaki
*Assistant Examiner* — Charles Zoltan Constantine
(74) *Attorney, Agent, or Firm* — Fay Sharpe LLP

(57) ABSTRACT

Methods of inhibiting or reducing tumor metabolism and growth are disclosed. A composition containing oxygen scavenging membrane fragments is administered within a tumor to create a hypoxic environment. This interferes with tumor growth and metabolism, and can lead to tumor death.

18 Claims, 47 Drawing Sheets
(36 of 47 Drawing Sheet(s) Filed in Color)

METHODS FOR INHIBITING TUMOR GROWTH

CROSS-REFERENCE TO RELATED APPLICATIONS

This application claims priority to U.S. Provisional Patent Application Ser. No. 62/109,136, filed on Jan. 29, 2015, the disclosure of which is hereby fully incorporated by reference.

BACKGROUND

The present disclosure relates to methods for inhibiting or reducing cancerous tumor metabolism growth and proliferation. Compositions for use in such methods are also disclosed.

Cancer is the abnormal growth of cells, which can create masses of tissue that can become malignant tumors or neoplasms. These formations can invade and destroy surrounding tissues, and may spread to other parts of the body (metastasis).

Physicians are constantly seeking new forms of cancer treatment to either bolster the effects of or supplant current cancer treatments such as chemotherapy, immunotherapy, radiation therapy, drug therapy, and cell transplantation. Alone, many of these treatments require repeated administrations with no guarantee of a reduction in tumor cell growth and proliferation. Further, many of these treatments result in adverse side effects, requiring subjects to undergo further discomfort and therapies. It would be desirable to identify additional methods of treating cancerous tumors.

BRIEF DESCRIPTION

Disclosed in various embodiments herein are methods for inhibiting cancerous tumor metabolism, growth and/or proliferation, both in vitro and in vivo. Generally speaking, a composition comprising oxygen reducing membrane fragments is administered intratumorally. It is believed that the membrane fragments under certain conditions create an anaerobic environment within the tumor, inhibiting growth or resulting in cell death. Because it affects a fundamental attribute of the tumor, i.e. the metabolic need for oxygen, this inhibition and treatment process should impact all types of tumors. The impact may also be dose-dependent.

In one aspect, the present disclosure is directed to compositions, and methods of utilizing the same, to reduce dissolved oxygen in vitro from a body or mass containing cancerous tumor cells. The compositions contain oxygen scavenging membrane fragments.

In yet another additional aspect, the present disclosure relates to methods for the inhibition of growth and proliferation of tumor cells in vivo, said method including: providing a composition comprising oxygen scavenging membrane fragments which contain an electron transport system which reduces oxygen to water in the presence of a hydrogen donor; and inoculating a tumor mass of a subject intratumorally with the composition.

In yet another additional aspect, the present disclosure relates to methods for the inhibition of growth and proliferation of tumor cells in vivo, said method including: providing a composition comprising oxygen scavenging membrane fragments which contain an electron transport system which reduces oxygen to water in the presence of a hydrogen donor, along with anaerobe bacteria; and inoculating a tumor mass of a subject intratumorally with the composition.

Further disclosed herein in various embodiments are methods for treating a cancerous tumor, comprising intratumorally administering to a patient, including a human or other mammal, a composition comprising a pharmaceutically effective amount of oxygen scavenging membrane fragments.

The oxygen scavenging membrane fragments can be derived from the cytoplasmic membranes of *Escherichia coli, Salmonella typhimurium, Gluconobacter oxydans, Pseudomonas aeruginosa*, or *Acetobacter*. In particular embodiments, the oxygen scavenging membrane fragments are derived from *Escherichia coli*.

The composition can further comprise a hydrogen donating substance. In particular embodiments, the hydrogen donating substance is lactic acid, succinic acid, alpha-glycerol phosphate, formic acid, malic acid, or a salt thereof.

The composition may be in the form of an injection, solution, suspension, or emulsion. The composition may contain the oxygen scavenging membrane fragments in an amount of about 0.01 units per milliliter to about 100 units per milliliter.

The cancerous tumors treated by these methods can be breast, cervical, colon, liver, lung, ovarian, pancreatic, prostate, brain, or bone cancer tumors.

The compositions can be administered in combination with chemotherapy, immunotherapy, radiation therapy, drug therapy, or cell transplantation.

Desirably, the administration of the composition creates localized hypoxia and fosters replication of anaerobes.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
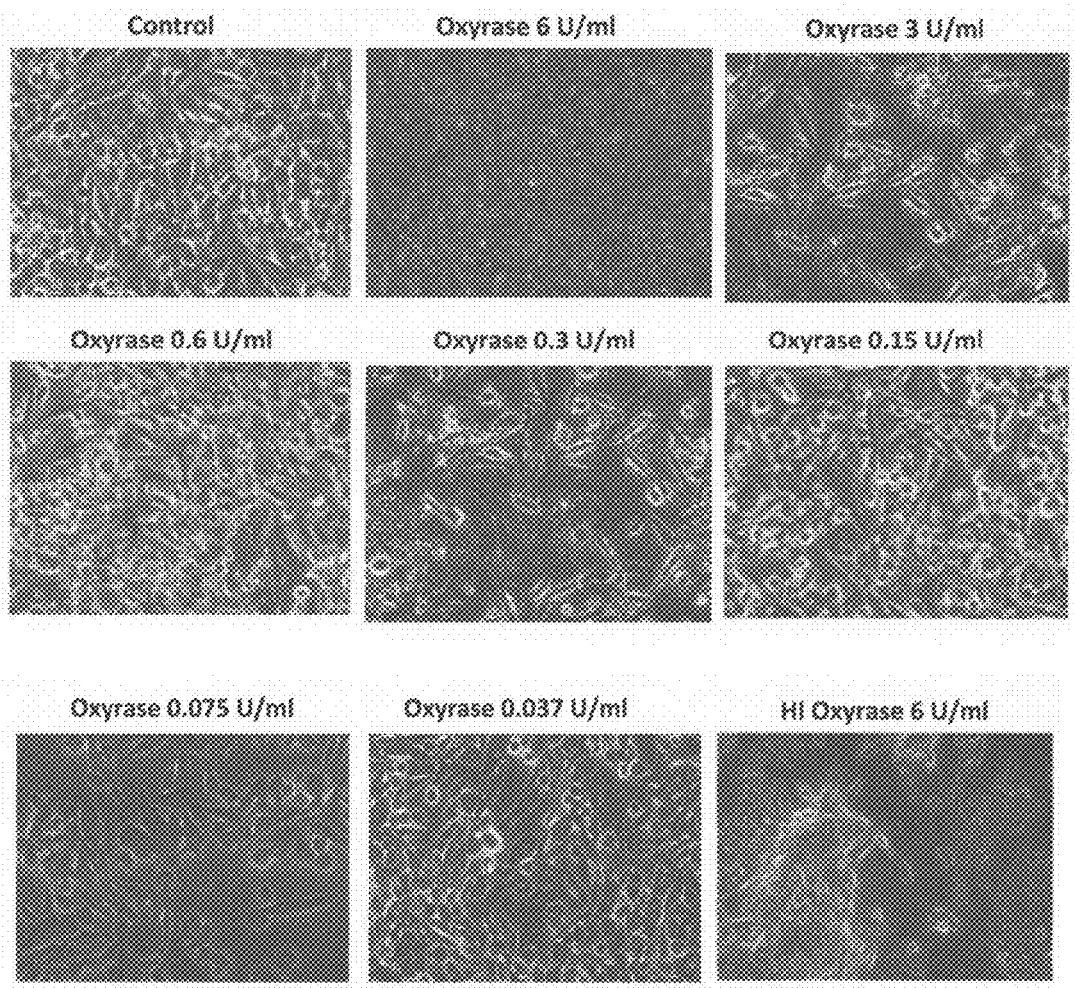
FIG. 1 is a set of images showing the effects of different concentrations of oxygen reducing membrane fragments (Oxyrase®) in the in vitro treatment of MDA-MB-231 human breast cancer cells after 72 hours.

The present disclosure may be understood more readily by reference to the following detailed description of desired embodiments and the examples included therein. In the following specification and the claims which follow, reference will be made to a number of terms which will be defined to have the following meanings.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

"Oxyrase®" is a commercially available enzyme system (from Oxyrase, Inc.) obtained from the cytoplasmic membranes of *Escherichia coli* to produce anaerobic conditions in a wide variety of environments.

The term "MTT assay" refers to a colorimetric assay for assessing cell viability. This assay uses NADPH-dependent cellular oxireductase enzymes, under defined conditions, to reflect the number of viable cells present. Those skilled in the art will recognize the procedure utilized.

The term "tumor" is used herein to refer both to a neoplasm that has formed a lump and to a neoplasm that has not formed a lump. The tumor can be malignant, or potentially malignant, or a secondary tumor.

The term "unit" is used herein to refer to a given amount of membrane fragments. One unit is defined as the amount of oxygen scavenging membrane fragments that will reduce dissolved oxygen in one milliliter of air saturated 40 mM phosphate buffer, pH 8.4, at 37 degrees Celsius, at the rate of 1% per second.

Cancerous tumors require oxygen to grow to a clinically important size, and need a blood supply to provide the oxygen. However, tumors consistently grow more quickly than new blood vessels can be formed, resulting in large regions that are poorly vascularized. Oxygen concentrations will vary widely within a single tumor, but developing hypoxia (i.e. a condition where the tumor is deprived of adequate oxygen supply) is significant in inducing tumor cells to undergo necrosis. Although tumor cells have a wide variety of responses to hypoxia, this strategy is still useful in treating cancerous tumors.

Hypoxia may also lead to suitable environments for fostering the growth of anaerobe bacteria. Generally, the interiors of tumors are not hospitable to anaerobes, and anaerobes have been found to only replicate in necrotic areas of tumors. Upon escaping tumors, anaerobes are generally not expected to survive. However, by creating hypoxic conditions, tumor infection by any anaerobes that are present might be enhanced, ultimately leading to tumor demise.

The present disclosure relates to methods for removing oxygen from in vivo and/or in vitro environments using pharmaceutical compositions comprising oxygen scavenging membrane fragments. The pharmaceutical compositions can also include, if desired, a hydrogen donating substance. When these compositions are applied to cancerous tumors, they create localized hypoxia and essentially starve tumors of oxygen, resulting in reduced cell proliferation and growth, and possibly cell death. The created oxygen-deprived environments provide optimal conditions for anaerobe bacteria infection and replication, which may lead to tumor necrosis.

The present application also relates to methods for removing oxygen from in vivo and/or in vitro environments using pharmaceutical compositions comprising oxygen scavenging membrane fragments and anaerobe bacteria. In this manner, tumors which may not yet have been colonized by such bacteria are inoculated, with the goal of causing tumor necrosis.

In this regard, the present disclosure removes oxygen through the use of specific oxygen scavenging membrane fragments. The membrane fragments, which contain an electron transport system that reduces oxygen to water, may be obtained from various sources. It is known that a great number of bacteria have cytoplasmic membranes which contain the electron transport system that effectively reduces oxygen to water if a suitable hydrogen donor is present in the medium. Some suitable bacterial sources include *Escherichia coli, Salmonella typhimurium, Gluconobacter oxydans, Pseudomonas aeruginosa*, and *Acetobacter*. These bacterial membranes have also been shown to be effective in removing oxygen from media and other aqueous and semi-solid environments.

The oxygen reducing effects produced by the cell membrane fragments from the bacterial sources indicated above can also be obtained by the use of oxygen reducing membranes from, for example, the mitochondrial organelles of a large number of higher non-bacterial organisms. More particularly, a great number of fungi, yeasts, plants, and animals have mitochondria that reduce oxygen to water if a suitable hydrogen donor is present in the medium. Some of the sources of oxygen reducing membranes from these mitochondria are: beef heart muscle, potato tuber, spinach, *Saccharomyces, Neurospora, Aspergillus, Euglena*, and *Chlamydomonas*.

Oxygen scavenging fragments are commercially available as Oxyrase®.

Oxyrase® consists of an enzyme system derived from the cytoplasmic membranes of microorganisms. Sterile (EC) and nonsterile (EC/NS) Oxyrase® in particular are derived from the cell membrane fragments of *E. coli* (0.2 microns or smaller) suspended in 20 mM phosphate buffer at a neutral pH. Substrates for Oxyrase® include lactic acid, succinic acid, formic acid, or their salts, and alpha-glycerol phosphate in addition to oxygen. One unit/ml Oxyrase® activity will reduce dissolved oxygen (air saturated 40 mM phosphate buffer, pH 8.4, at 37 degrees Celsius) at the rate of 1% per second. The rate of oxygen removal increases with temperature, and above 55 degrees Celsius, Oxyrase® begins to be inactivated but will persist up to 80 degrees Celsius. Oxyrase® is active over a wide pH range of 6.8 to 8.4.

The exact amount of membranes containing the enzyme systems needed to reduce oxygen in the tumor can vary by a number of parameters including pH, temperature, kinds and amounts of substrate present, and amount of oxygen present within the tumor. Some experimentation may be necessary to optimize the effectiveness of the membranes on the various different types of tumors. In some embodiments, the pharmaceutical composition contains the oxygen scavenging membrane fragments in the amount of about 0.01 units/mL to about 100 units/mL, or from about 0.01 units/mL to about 10 units/mL, or from about 0.3 unit/mL to about 10 units/mL, or from about 1 unit/mL to about 10 units/mL.

A hydrogen donating substance (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts. The hydrogen donating substance may also be present in the pharmaceutical composition.

Moreover, in another embodiment, at least one anaerobe bacteria species or a mix of anaerobe bacteria may be included in the pharmaceutical composition or administered in tandem with said pharmaceutical composition. The terms "anaerobic" and "anaerobe" are used herein to refer specifically to bacteria that will die in the presence of oxygen, i.e. obligate anaerobes. The anaerobe bacteria species may be *Bacteroides fragilis, Bifidobacterium adolescentis, Clostridium perfringens, Fusobacterium nucleatum, Porphyromonas levii, Peptostreptococcus anaerobius,* or *Prevotella melaninogenica,* for example. Alternatively, the anaerobe bacteria may be genetically engineered. The anaerobe bacteria can be present in the amount of $10^6$ to $10^8$ colony-forming units (CFU) per milliliter of the composition. The anaerobe bacteria may be present in the composition in any form, for example as spores or as cells.

The pharmaceutical compositions containing the oxygen reducing membrane fragments are contemplated to be administered intratumorally. The dose used in a particular formulation or application can be determined by one of ordinary skill in the art. It is contemplated that the compositions can be used to treat several different types of tumors, including breast, cervical, colon, liver, lung, ovarian, pancreatic, prostate, brain, or bone cancer tumors.

In particular embodiments, the composition may contain the oxygen scavenging membrane fragments in an amount of about 0.01 units per milliliter (u/mL) to about 100 units per milliliter. Specifically, the composition may contain the oxygen scavenging membrane fragments in an amount of greater than 0.1 units per milliliter, or in an amount of at least 0.5 units per milliliter, or in an amount of at least 5 units per milliliter.

The pharmaceutical composition may be in the form of an injection, solution, suspension, or emulsion. It is contemplated that the composition will be delivered by injection.

The pharmaceutical composition may include a pharmaceutically acceptable carrier. The carrier acts as a vehicle for delivering the membrane fragments. Examples of pharmaceutically acceptable carriers include liquid carriers like water, oil, and alcohols, in which the molecular antagonists can be dissolved or suspended.

The pharmaceutical composition may also include excipients. Particular excipients include buffering agents, preservative agents, polymers, and stabilizers. Buffering agents are used to control the pH of the composition. Preservatives are used to prevent microbial growth. Examples of preservatives include benzyl alcohol, m-cresol, and phenol. Hydrophilic polymers such as dextran, hydroxyl ethyl starch, polyethylene glycols, and gelatin can be used to stabilize proteins. Protein stabilizers can include polyols, sugars, amino acids, amines, and salts. Suitable sugars include sucrose and trehalose. Amino acids include histidine, arginine, glycine, methionine, proline, lysine, glutamic acid, and mixtures thereof. It should be noted that particular molecules can serve multiple purposes. For example, histidine can act as a buffering agent and an antioxidant.

Dose will depend on a variety of factors, including the disease type, patient age, patient weight, and tolerance. The dose of a particular patient can be determined by the skilled clinician using standard pharmacological approaches in view of the above factors. The response to treatment may be monitored by known methods. The skilled clinician will adjust the dose based on the response to treatment revealed by these measurements. A single administration may usually be sufficient to produce a therapeutic effect, but it is contemplated that multiple administrations will be used to assure continued response over a substantial period of time. It is believed that the composition may need to be administered once a week but desirably at lower intervals such as once or twice a month.

It is contemplated that the pharmaceutical compositions of the present disclosure can be used in combination with other therapies, such as chemotherapy, immunotherapy, radiation therapy, drug therapy, or cell transplantation. Together, these combination treatments should produce a greater or longer-lasting decrease in the growth of the tumor or in the death of the tumor. For example, using the oxygen scavenging membrane fragments together with anti-angiogenic agents (e.g. microtubule inhibitors or other drugs that inhibit growth of blood vessels) should encourage hypoxia to occur within larger volumes or for longer time periods. Alternatively, some drugs may target tumor cells in well-perfused regions, and the hypoxia created by the oxygen scavenging membrane fragments would target tumor cells in poorly perfused regions. As another example, there are some drugs which are activated only in hypoxic environments, such as tirapazamine.

Infection of a tumor by anaerobes should be especially therapeutic when used in a combination treatment with the oxygen-scavenging membrane fragments. Anaerobe infection of a tumor is disruptive and may lead to tumor necrosis; however anaerobes have been found to replicate only in necrotic areas of a tumor. The addition of Oxyrase® overcomes this limitation, permitting anaerobe replication in oxygen-deprived environment, thereby exacerbating the effects of Oxyrase® alone to disrupt tumors and lead to tumor necrosis. As discussed above, the pharmaceutical composition itself may include anaerobe bacteria, so that tumors not already infected can become inoculated thereby.

Because of the nature of Oxyrase® and because it is injected intratumorally, there should be no adverse systemic effects on the patient, unlike other cancer treating pharmaceuticals.

The present disclosure is further illustrated in the following non-limiting working examples, it being understood that these examples are intended to be illustrative only and that the disclosure is not intended to be limited to the materials, conditions, process parameters and the like recited herein.

EXAMPLES

Prior to all in vitro and in vivo testing, Oxyrase® (i.e. oxygen scavenging membrane fragments) was tested to see whether its use would affect the luciferase or MTT assays that were to be used to measure cell viability.

In this regard, higher luciferase expression correlates to a higher number of viable cells. Higher absorbance in the MTT assay also correlates to a higher number of viable cells.

Additional examples assessed the in vitro cytotoxic effect of Oxyrase® on cancer cell lines through CellTiter Glo® assays. Further examples assessed the effect of Oxyrase® with anaerobes on cancer cells lines.

First Set of Experiments

Materials and Methods

Luciferase labeled MDA-MB-231 human breast cancer cells and luciferase labeled U87 human brain tumor cells were obtained and plated into a set of 24-well plates and a set of 96 well-plates. The cells were allowed to adhere overnight in a 5% carbon dioxide incubator at 37 degrees Celsius. Half of the plates were then placed in a hypoxia chamber under low oxygen conditions (0.5-1% $O_2$) to simulate the in vivo environment of certain tumors.

The culture medium was replaced with fresh medium containing the substrate dl-lactate (20 mM) and Oxyrase® at multiple concentrations (0, 0.037, 0.075, 0.15, 0.3, 0.6, 3, or 6 u/mL) to each group of at least six replicates. In one set of wells, the cells were treated with heat-inactivated (HI) Oxyrase® as a control, and in another set of wells, the cells were incubated with fresh media as an additional control. The pH of the media was maintained at 8.4 to support the enzymatic activity of Oxyrase®.

The 24-well plates were incubated at 37 degrees Celsius for 5 days and tumor cell growth evaluated at 1, 3, and 5 days by measurement of bioluminescence generated by luciferase-expressing cells with the Lumina XR imaging instrument after adding the luciferin substrate. During this time, any change in the cell morphology was monitored. To ensure that the luciferase expression measured by bioluminescence correlated specifically with the number of proliferating healthy cells, viable cells from the wells were counted after trypsinization.

Heat inhibited Oxyrase® (HI-Oxyrase®), which is incubated at 85 degrees Celsius for 30 minutes to inactivate oxygen-removing activity, served as an additional control, and was added to wells at a concentration of 6 u/mL based on its original activity.

Results

Based on FIG. 1, it seems the effects of Oxyrase® on MDA-MB-231 human breast cancer cells are concentration dependent. At 0.037 u/mL, the cells still show fairly normal morphology but are less numerous than they were under controlled conditions. As the dosage concentrations gradually increased, cells began to lose their defined structures and slow in proliferation. Particularly, Oxyrase® administered at a concentration of 6 u/mL seemed the most effective after 72 hours of inhibiting cell growth and proliferation. To a lesser extent, HI-Oxyrase® administered at 6 u/mL also inhibited cell growth and proliferation but not to the same extent as normal Oxyrase® did.

Figure 2:
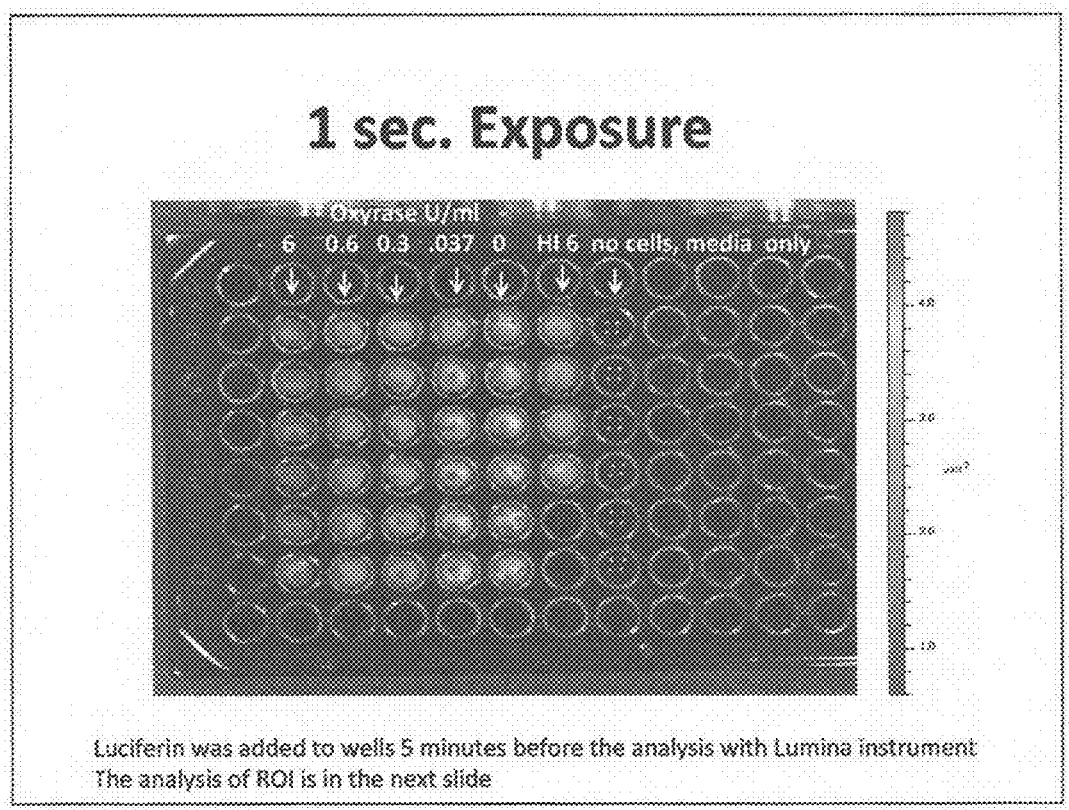
FIG. 2 is an image from the Lumina instrument showing the effects of different concentrations of Oxyrase® in the in vitro treatment of MDA-MB-231 human breast cancer cells after a 1 second exposure.

Luciferin was added to the wells. After five minutes, the Lumina instrument was used with a one-second exposure. FIG. 2 shows the results, and confirms that Oxyrase® exhibits concentration-dependent effects on MDA-MB-231 cells. The most effective concentration was 6 u/mL, but effects were illustrated at as little as 0.037 u/mL. As the concentration of Oxyrase® increased, the number of cells decreased, suggesting that cells stopped growing or died upon exposure to increasing concentrations of Oxyrase®.

Figure 3:
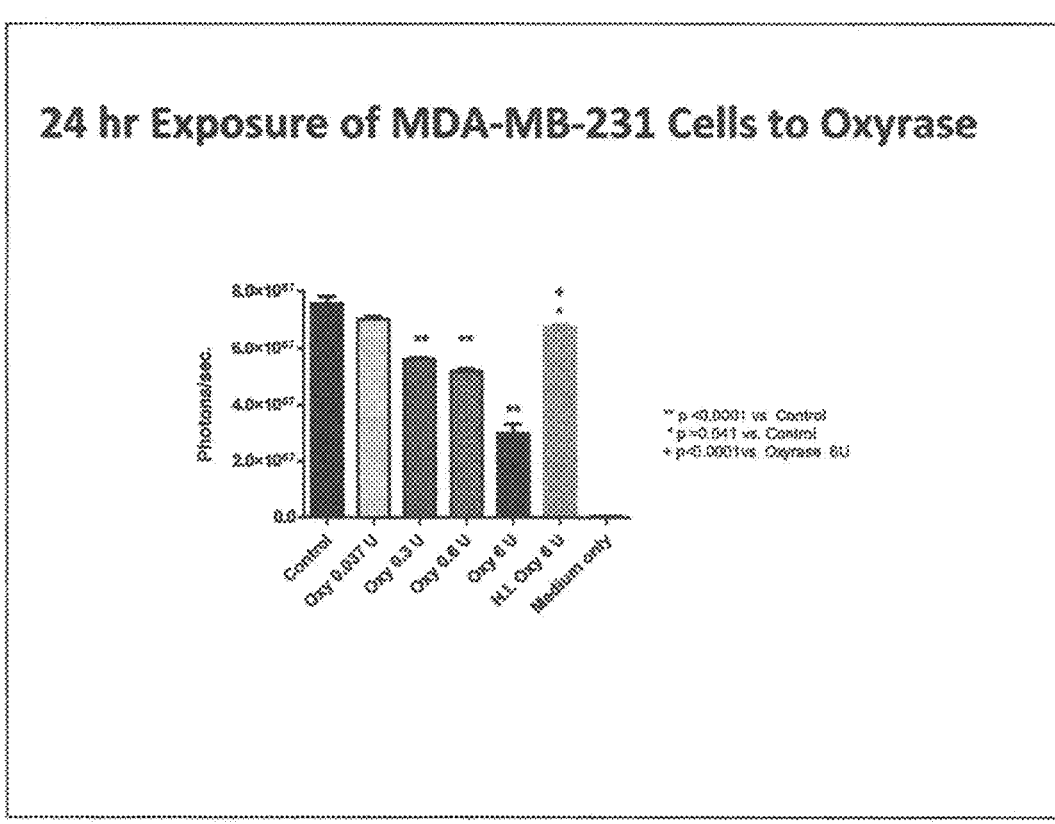
FIG. 3 is a graph that shows the effects of different dosages of Oxyrase® on absorbance of luciferin after 24 hours. The y-axis is photons per second.

FIG. 3 is a graphic interpretation of data collected after a 24 hour exposure of MDA-MB-231 cells to Oxyrase® at different concentrations. As can be seen by the decrease in luciferin expression, the increasing concentrations of Oxyrase® had a significant effect on activity. Oxyrase® administered at a concentration of 6 u/mL exhibited less than half the activity as that of the control (i.e. untreated MDA-MB-231 cells alone). Further, HI-Oxyrase® had no effect compared to the control.

Figure 4:
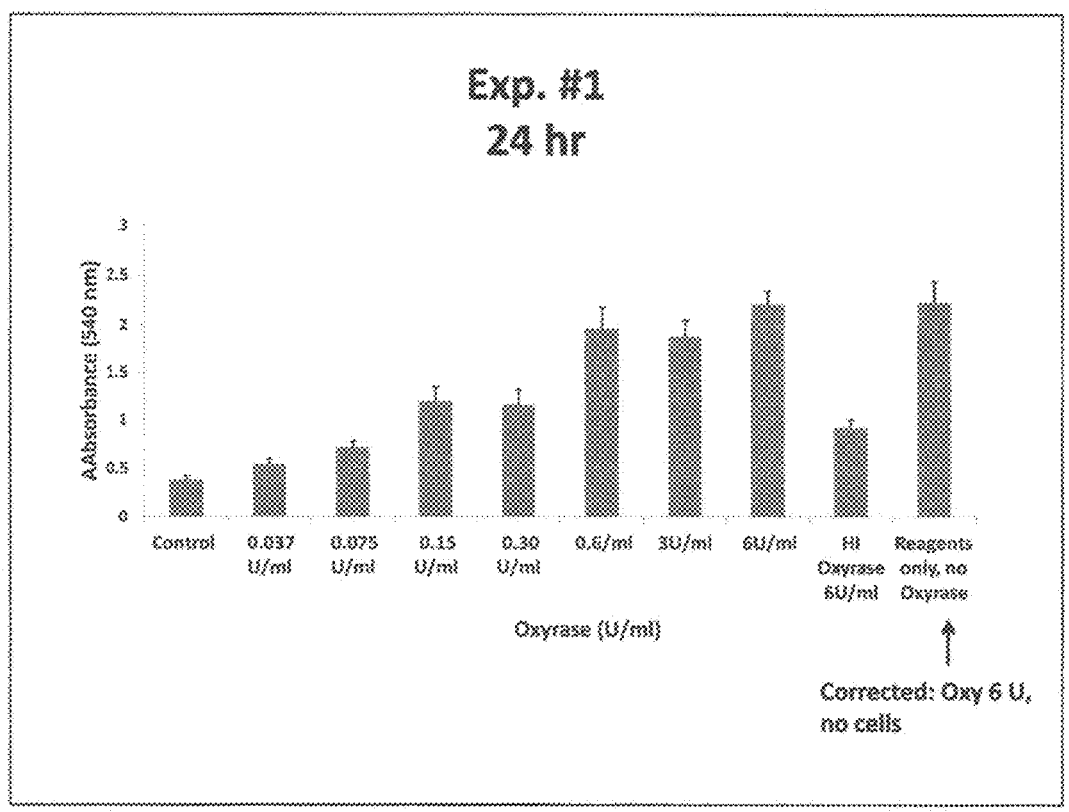
FIG. 4 is a graph that shows the effects of different dosages of Oxyrase® on absorbance of luciferin after 24 hours.
Figure 5:
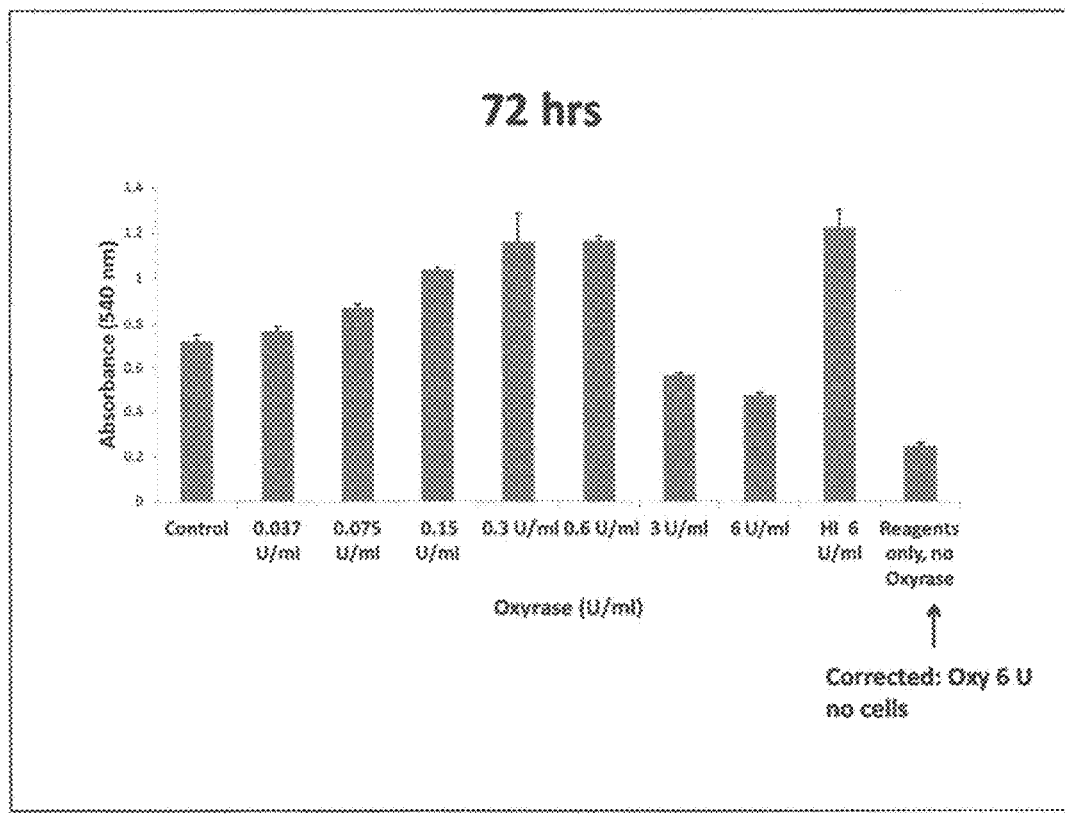
FIG. 5 is a graph that shows the effects of different dosages of Oxyrase® on absorbance of luciferin after 72 hours.

FIG. 4 and FIG. 5 are graphs of data collected after a 24 hour exposure and a 72 hour exposure, respectively, of MDA-MB-231 cells to Oxyrase® at different concentrations. Oxyrase® increased absorbance in the MTT assay in a concentration-dependent fashion. Further the HI-Oxyrase® exhibited a weaker effect. The results after 24 hours as depicted in FIG. 4 are inaccurate, as high absorbance values were detected in wells containing only 6 u/ml Oxyrase® with no cells (last bar on the right), suggesting that Oxyrase® affected the MTT assay. However, FIG. 5 demonstrates that this effect significantly decreased over the next 48 hours. After 72 hours of exposure, Oxyrase® decreased absorbance at the high concentrations of 3 and 6 u/mL while HI-Oxyrase® did not. As Oxyrase® did not affect the MTT assay to the extent it did after 24 hours, the 72 hour absorbance value was subtracted from the other values in order to normalize the results.

It is noted that the increasing absorbances shown in FIG. 4 and FIG. 5 are attributed to the effect of Oxyrase® on the MTT assay, and does not show that increasing concentrations of Oxyrase® result in a higher number of viable cells.

With respect to the U87 human brain cancer cells, no significant response was observed after exposure to Oxyrase®.

Second Set of Experiments

Materials and Methods

In a second procedure, the 96-well plates were analyzed for cell proliferation using the MTT assay. After 48-72 hours, the cells were incubated with 1 mg/mL thiazolyl blue tetrazolium bromide for 3 hours. The assays were covered with an oxygen impermeable film. The medium was then removed and the MTT crystals solubilized in DMSO before reading the plate with microplate reader instrumentation (540 nm absorbance).

Results

Figure 6:
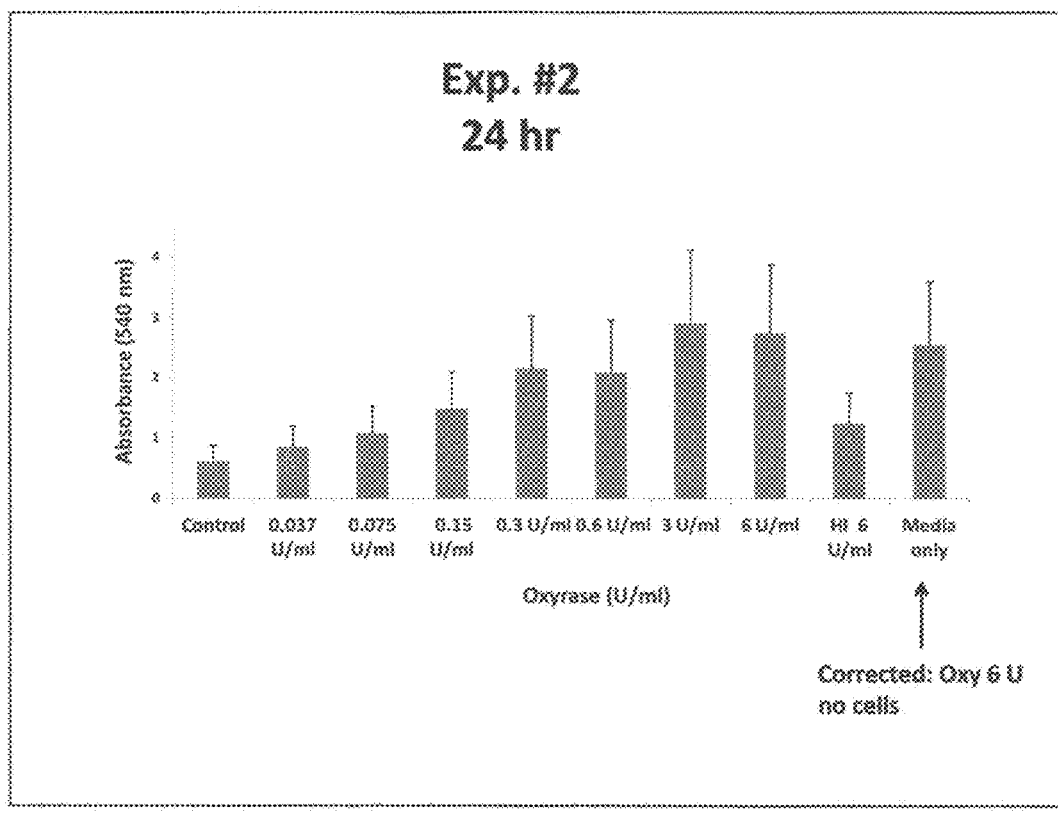
FIG. 6 is a graph that shows the effects of different dosages of Oxyrase® on absorbance of luciferin after 24 hours and MTT assaying.
Figure 7:
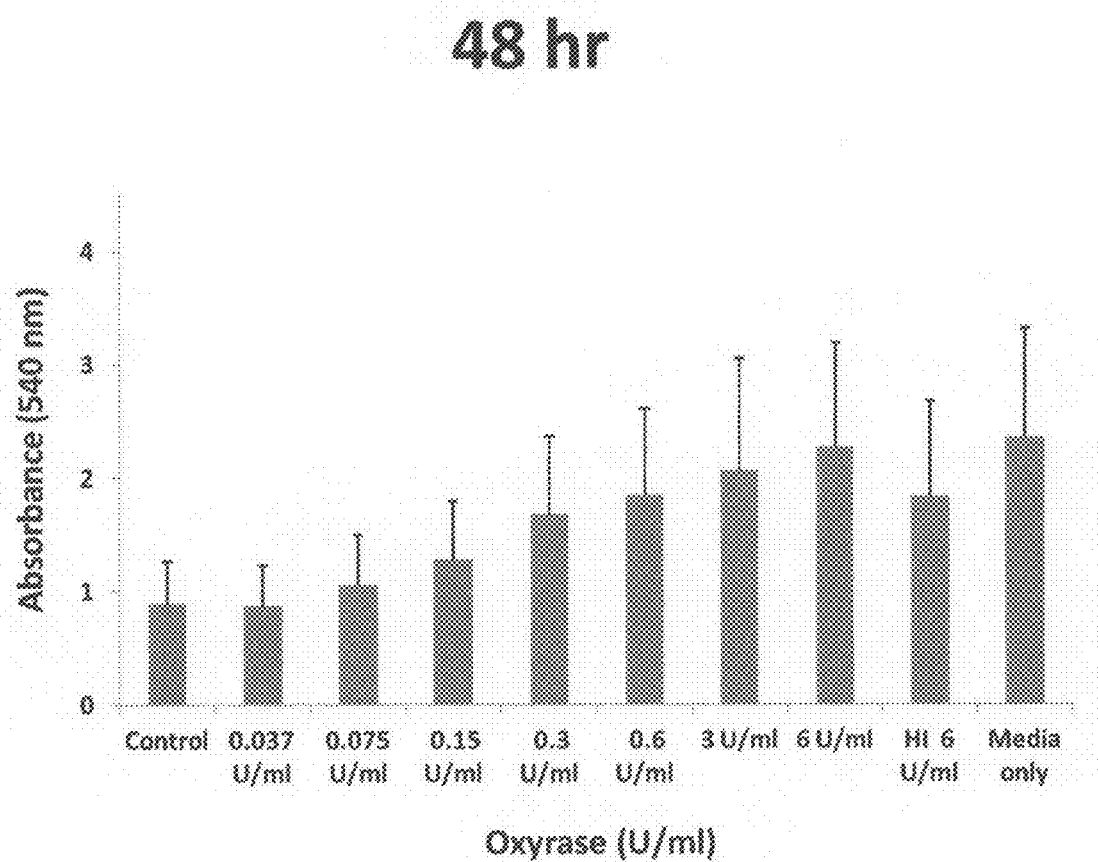
FIG. 7 is a graph that shows the effects of different dosages of Oxyrase® on absorbance of luciferin after 48 hours and MTT assaying.

FIG. 6 and FIG. 7 are graphic interpretations of data collected after 24 and 48 hour exposures respectively and MTT assaying of MDA-MB-231 human breast cancer cells to Oxyrase® at different concentrations. As compared to the first set of experiments seen in FIGS. 3-5, there is more variability but the overall results are quite similar, with concentrations of 3 and 6 u/mL having the greatest effect on absorbance.

Again, it is noted that the increasing absorbances shown in FIG. 6 and FIG. 7 are attributed to the effect of Oxyrase® on the MTT assay, and does not show that increasing concentrations of Oxyrase® result in a higher number of viable cells.

Figure 8:
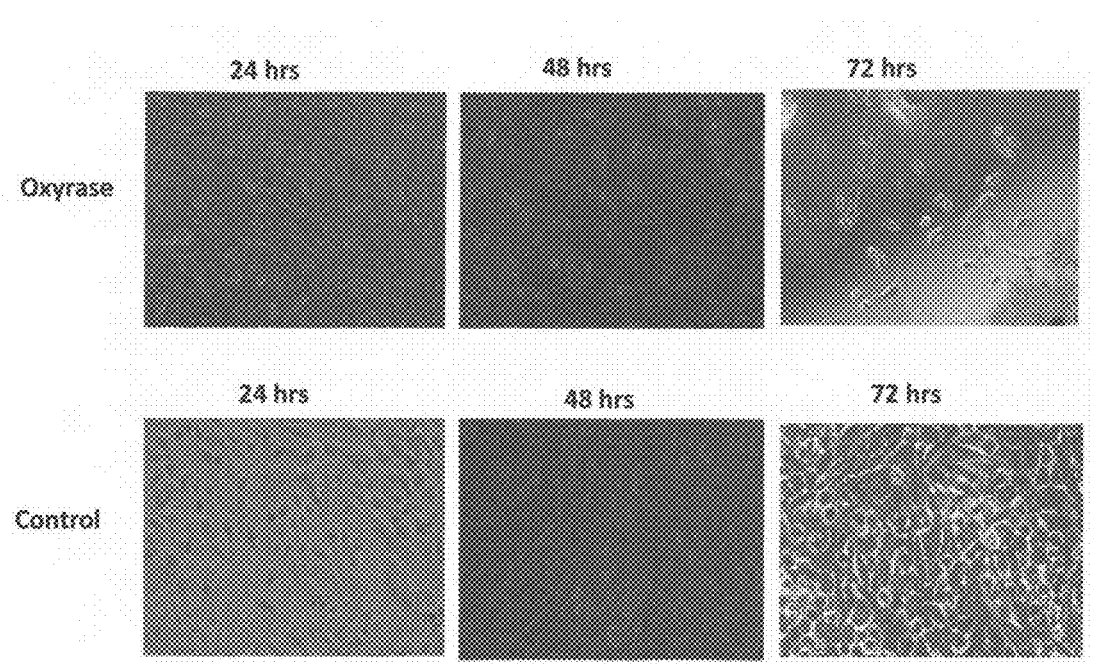
FIG. 8 is a set of images showing the effects 72 hours after treating MDA-MB-231 human breast cancer cells in vitro with 6 u/mL Oxyrase®.

As shown in the microscopic images of FIG. 8, Oxyrase® has a continuous effect on MDA-MB-231 cells. After treatment with 6 u/mL Oxyrase®, cells were unable to maintain their morphology. At 72 hours, very few cells remain with limited structures compared to those shown in the control group panel.

Third Set of Experiments

Materials and Methods

To verify that the Oxyrase® did not have a background or adverse effect on the MTT assay, the second procedure of the second set of experiments was repeated; however, the medium containing Oxyrase® was removed from all the wells prior to the addition of the MTT dye and stopping/solubilization solution. This verification experiment determined the true effect of Oxyrase® at 6 u/mL on cell proliferation.

Results

Figure 9:
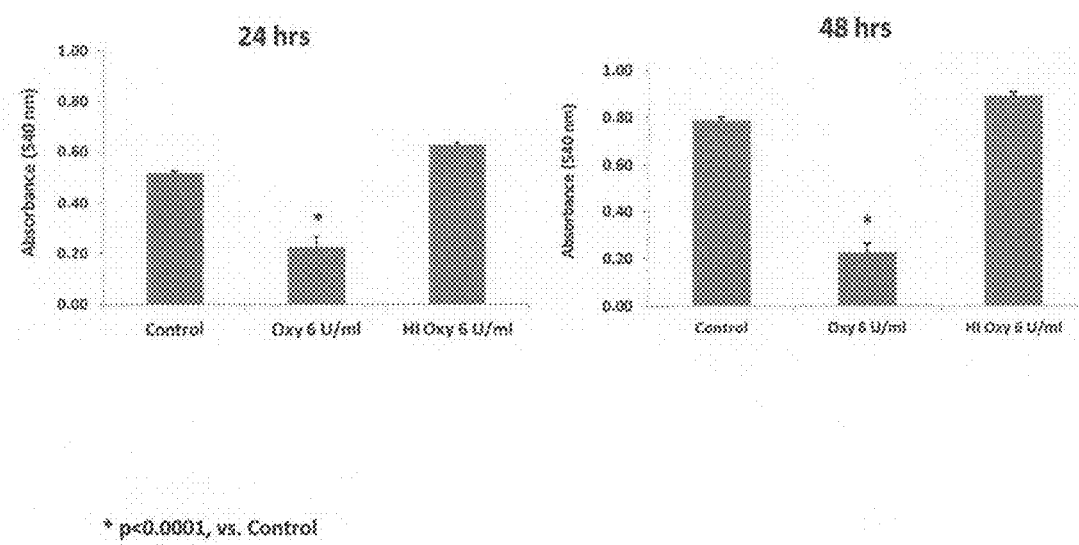
FIG. 9 is a graph that shows Oxyrase® inhibition corrected for the Oxyrase® background effect on the assay.

As shown in FIG. 9, the non-specific effect of Oxyrase® on the MTT assay was successfully eliminated. The removal of Oxyrase® prior to the addition of the MTT dye resulted in depressed absorbance following administration of Oxyrase® at a concentration of 6 u/mL.

Fourth Set of Experiments

Materials and Methods

In a fourth procedure, luciferase labeled MDA-MB-231 human breast cancer cells were implanted in a quantity of $5 \times 10^6$ cells into the mammary fat pad of mice at each side of three athymic nude mice. The growth of tumors was first measured by determining the increase of the bioluminescent signal from day 15 to day 19 post cell implantation. Treatment began with an intratumoral administration of Oxyrase® or heat-inactivated Oxyrase® (as a control) at the dose of 6 u/mL.

Five days post treatment initiation, the mice were imaged 15 minutes after intraperitoneal administration of the substrate luciferin and tumors were measured for growth.

Results

Figure 10:
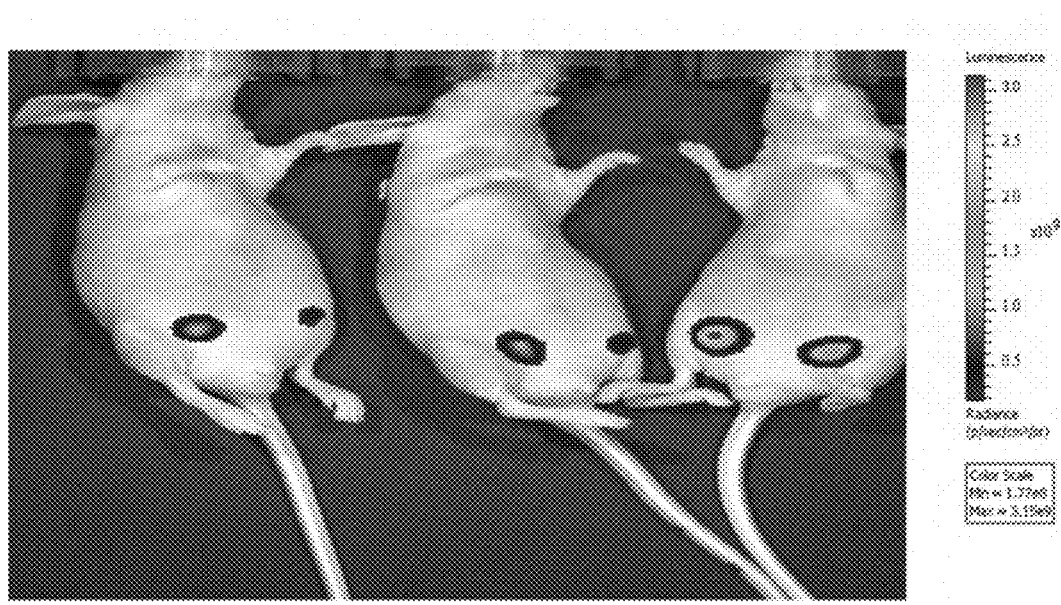
FIG. 10 is an image of the bioluminescence of MDA-MB-231 human breast cancer cells 15 days after in vivo implantation into mammary fat pads of mice.

FIG. 10 is an image confirming MDA-MB-231 human breast cancer cell bioluminescence in the mammary fat pads of the three mice 15 days after implantation.

Figure 11:
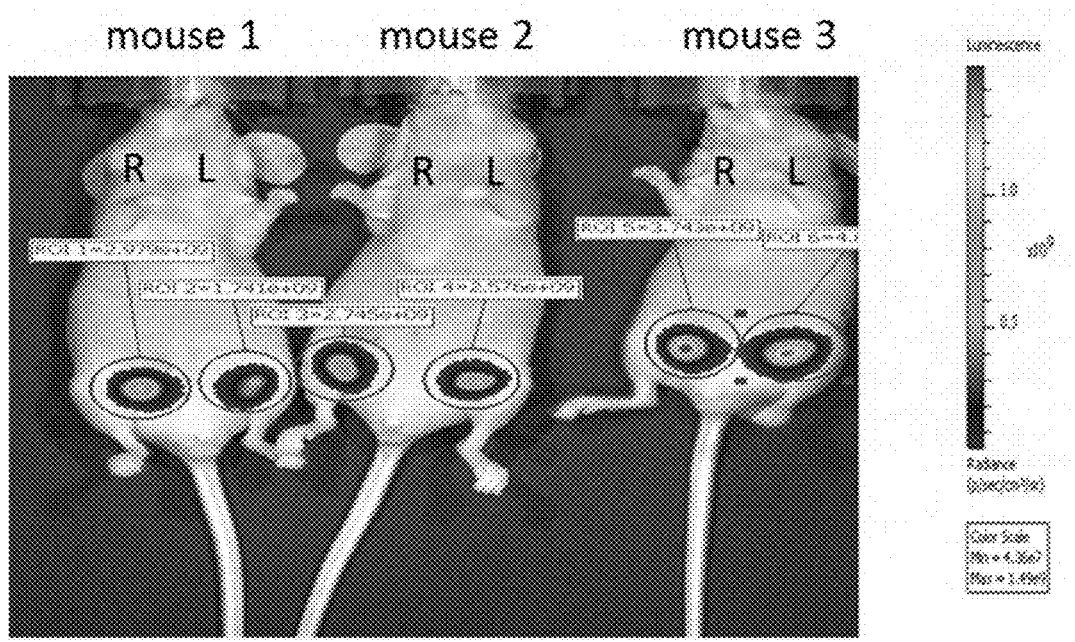
FIG. 11 is an image of the bioluminescence of MDA-MB-231 human breast cancer cells 19 days after in vivo implantation into mammary fat pads and on the first day of treatment with either 6 u/mL Oxyrase® or 6 u/mL heat-inactivated Oxyrase®.

FIG. 11 is an image showing the administration scheme of either 6 u/mL Oxyrase® or 6 u/mL heat-inactivated Oxyrase® to the MDA-MB-231 tumors in the three mice 19 days after implantation. Mouse 1 was administered with 6 u/mL Oxyrase® to both its right and left mammary fat pads. Mouse 2 was administered with 6 u/mL heat-inactivated Oxyrase® to both its right and left mammary fat pads. Mouse 3 was administered with 6 u/mL Oxyrase® to its right mammary fat pad and 6 u/mL heat-inactivated Oxyrase® to its left mammary fat pad.

Figure 12:
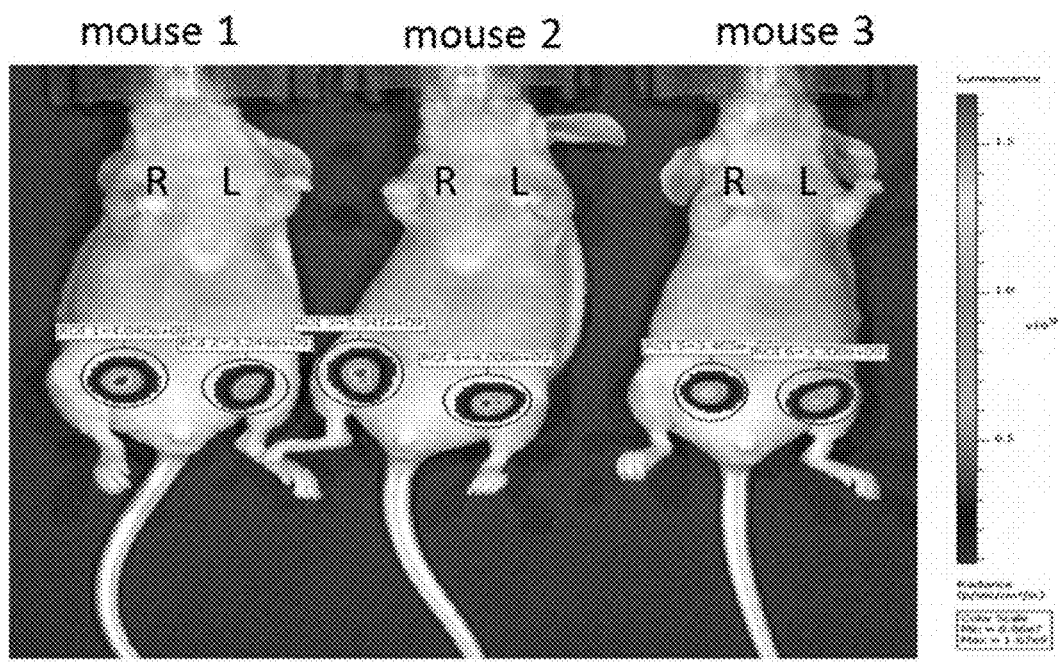
FIG. 12 is an image of the bioluminescence of MDA-MB-231 human breast cancer cells 24 days after in vivo implantation into mammary fat pads and 5 days after initiating treatment with Oxyrase®.

As shown in FIG. 12 and Table 1 below, the bioluminescence of the MDA-MB-231 cells was suppressed over a period of 5 days of treatment with Oxyrase® compared to cells treated with heat-inactivated Oxyrase®, which exhibited increases in bioluminescence.

TABLE 1

| Mouse (side) | Treatment Scheme | Bioluminescence at Day 1 of Treatment | Bioluminescence at Day 5 of Treatment |
|---|---|---|---|
| Mouse 1 (Right) | Oxyrase ® | $2.979 \times 10^9$ | $4.840 \times 10^9$ |
| Mouse 1 (Left) | Oxyrase ® | $2.741 \times 10^9$ | $3.244 \times 10^9$ |
| Mouse 2 (Right) | Heat-inactivated Oxyrase ® | $2.745 \times 10^9$ | $5.341 \times 10^9$ |
| Mouse 2 (Left) | Heat-inactivated Oxyrase ® | $2.576 \times 10^9$ | $4.008 \times 10^9$ |
| Mouse 3 (Right) | Oxyrase ® | $3.743 \times 10^9$ | $3.465 \times 10^9$ |
| Mouse 3 (Left) | Heat-inactivated Oxyrase ® | $4.6 \times 10^9$ | $3.308 \times 10^9$ |

Figure 13:
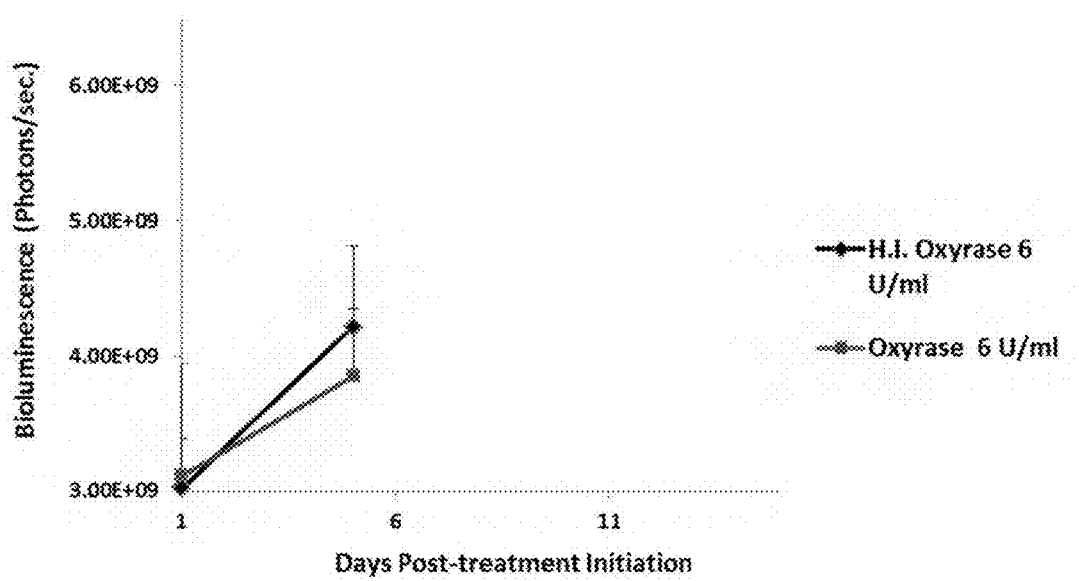
FIG. 13 is a graph that shows the increase in bioluminescence of MDA-MB-231 human breast cancer cells implanted in vivo over 5 days of treatment with either Oxyrase® or heat-inactivated Oxyrase®.

The above results are visualized in the graph of FIG. 13, which illustrates that those tumors treated with Oxyrase®, rather than the control, exhibited less bioluminescence after 5 days of treatment. Specifically, Oxyrase® reduced the bioluminescent signal by an average of 38%.

Figure 14:
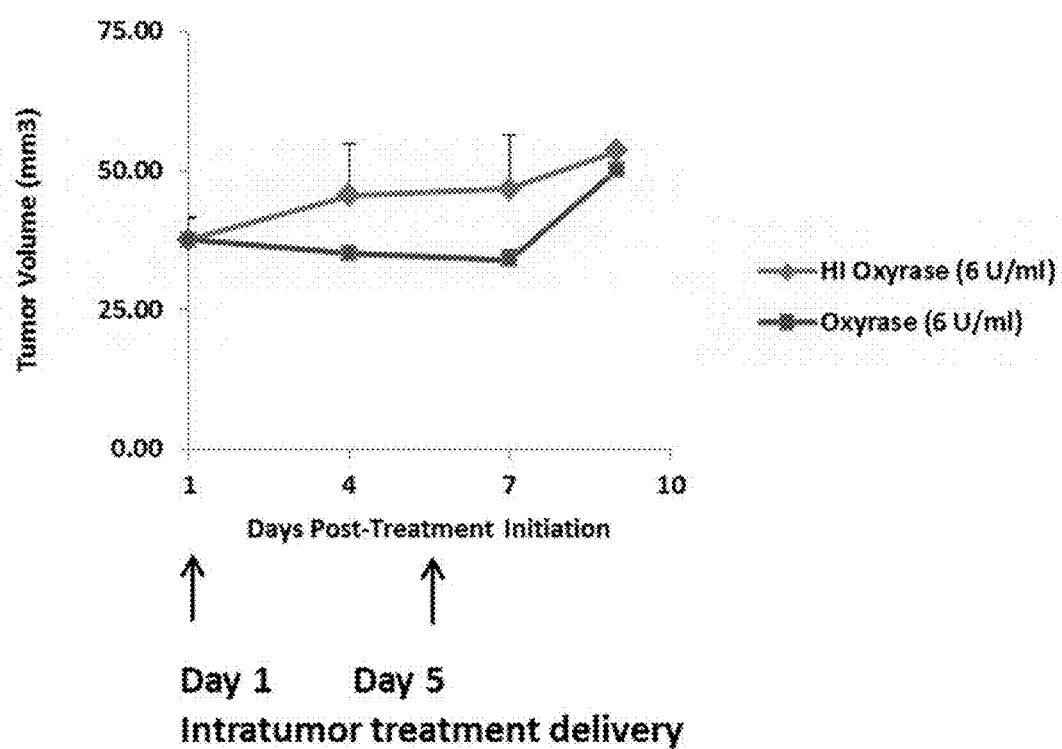
FIG. 14 is a graph that evaluates tumor growth of MDA-MB-231 human breast cancer cells implanted in vivo over 10 days of treatment with either Oxyrase® or heat-inactivated Oxyrase®.

Further, those tumors treated Oxyrase® decreased in actual size over a period of 7 days post treatment, as shown in FIG. 14, which depicts the evaluation of tumor growth by caliper measurement over 10 days. However, after one week of treatment, decrease in tumor growth attenuated.

Fifth Set of Experiments

Materials and Methods

In a fifth procedure, luciferase labeled MDA-MB-231 human breast cancer cells and U87 human brain tumor cells were implanted in 12 female athymic nude mice (6 mice/model) on both sides of each animal to induce formation of tumors (12 tumors/model). MDA-MB-231 cells were implanted in the mammary fat pad at the number of $5 \times 10^6$ and U87 cells were implanted subcutaneously at the number of $3 \times 10^6$, both with 50% Matrigel. When the tumors reached the size of at least 150-200 mm³, Oxyrase® was directly delivered to 6 tumors and heat-inactivated Oxyrase® was directly delivered to the other 6 tumors. Treatment with Oxyrase® continued every 4-5 days for at least 2 weeks. The tumor bearing mice received intraperitoneal injections of luciferin substrate (150 mg/Kg) and were imaged with the Lumina XR instrument before delivery of Oxyrase® (pre-dosage) and at different times following initiation of treatment (i.e. Days 1, 3, and 5 to determine the luciferase expression of viable tumor cells by measure of bioluminescence).

Sixth Set of Experiments

Materials and Methods

MCF-7 human breast cancer cells were obtained and cultured for 3 passages in recommended media (DMEM medium, F12-K medium, McCoys 5a medium) and 10% fetal bovine serum (FBS). Cells were harvested by trypsinization, counted on ViCell, then plated at a density of 20,000 cells per well in ten clear bottom Perkin Elmer 96 well view plates and ten clear Costar 96 well plates. Oxyrase® and substrate were added to wells in quadruplicate: a first column of 4 wells had cells alone in each well; a second column of 4 wells contained Oxyrase® (20 units/mL) and cells; a third column of 4 wells contained L-Lactate at 40 mM and cells; and a fourth column of 4 wells contained cells and buffer, the latter added at equal volume to Oxyrase®. Five Perkin Elmer 96 well view plates and five clear Costar 96 well plates were placed in an incubator at 37 degrees Celsius and supplied with 5% carbon dioxide and 10% humidity. The remaining plates were placed in an incubator in anaerobic boxes containing oxygen depleting packets.

On days 0, 1, 3, 5, and 7, one Perkin Elmer 96 well view plate each from aerobic and anaerobic incubators were removed and a CellTiter Glo® assay was performed. CellTiter Glo® reagents were thawed at room temperature and mixed just before being added to each plate. Equal volume (maximum 125 µL) of CellTiter Glo® reagent was added to the plate and the plate incubated in the dark for 15 minutes. Plates were read using a Wallac Victor2 plate reader using the luminescence range At the same time, one clear Costar 96 well plate each from aerobic and anaerobic incubators were removed, and cells were trypsinized and counted using a ViCell counter.

Results

Figure 15:
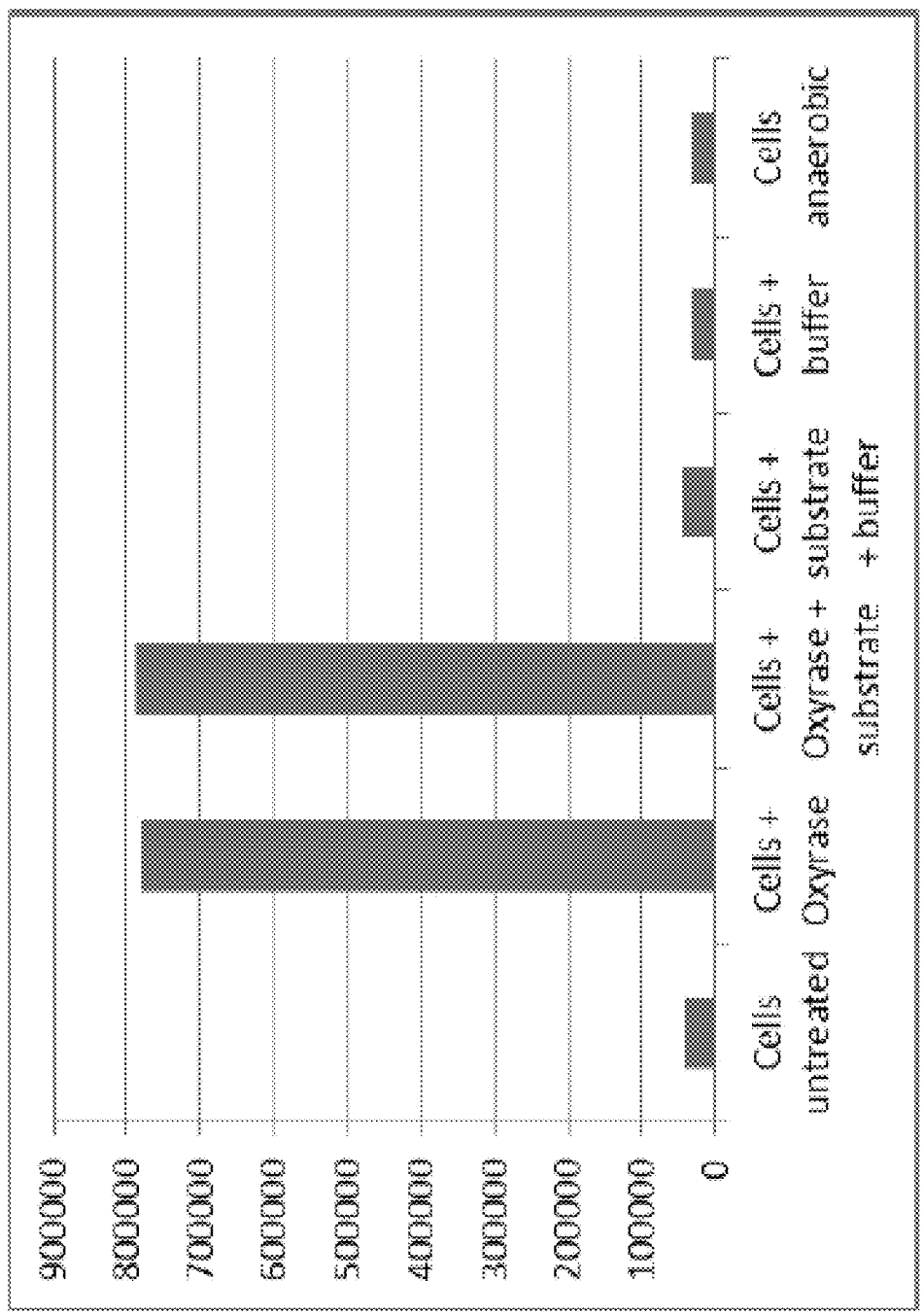
FIG. 15 is a graphical representation of the average number of anaerobic cells and MCF-7 human breast cancer cells untreated, treated with Oxyrase®, treated with Oxyrase® and a substrate, cultured in substrate and buffer, and cultured in buffer following a ViCell count. The y-axis is relative light units (RLU).
Figure 16:
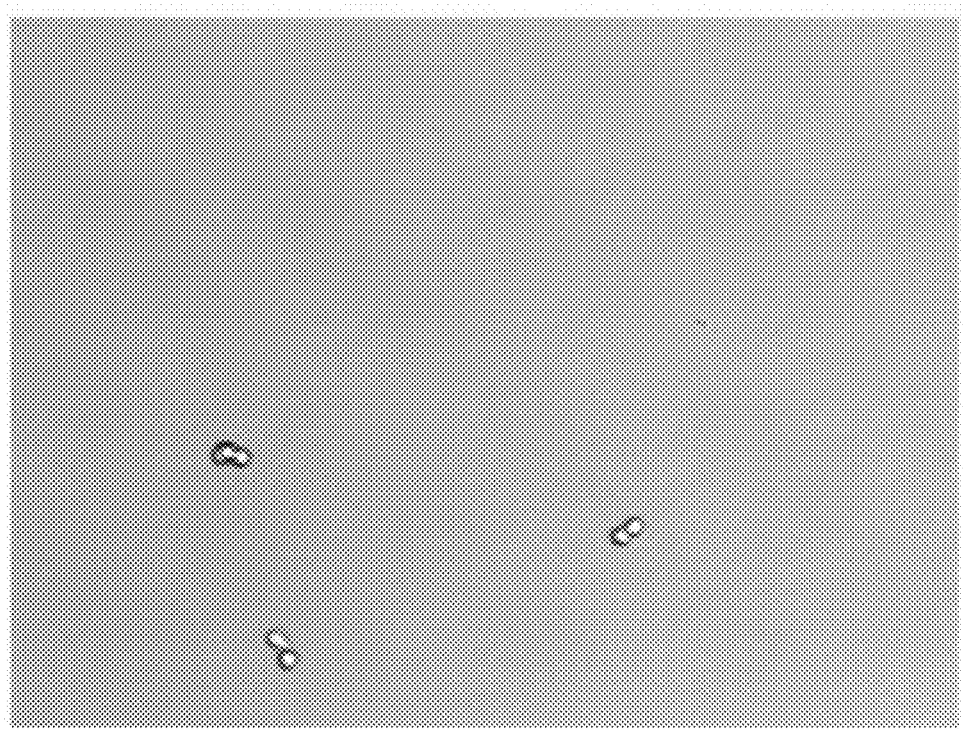
FIG. 16 is an image from the ViCell software showing the untreated MCF-7 human breast cancer cells on day 1.
Figure 17:
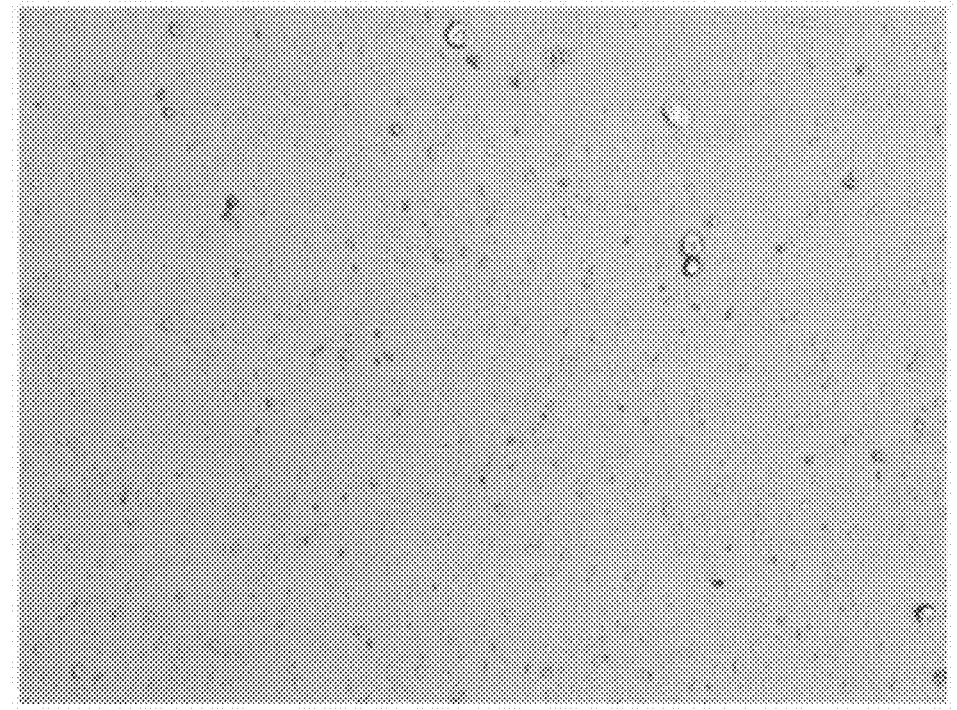
FIG. 17 is an image from the ViCell software showing the MCF-7 human breast cancer cells cultured with Oxyrase® on substrate on day 1.
Figure 18:
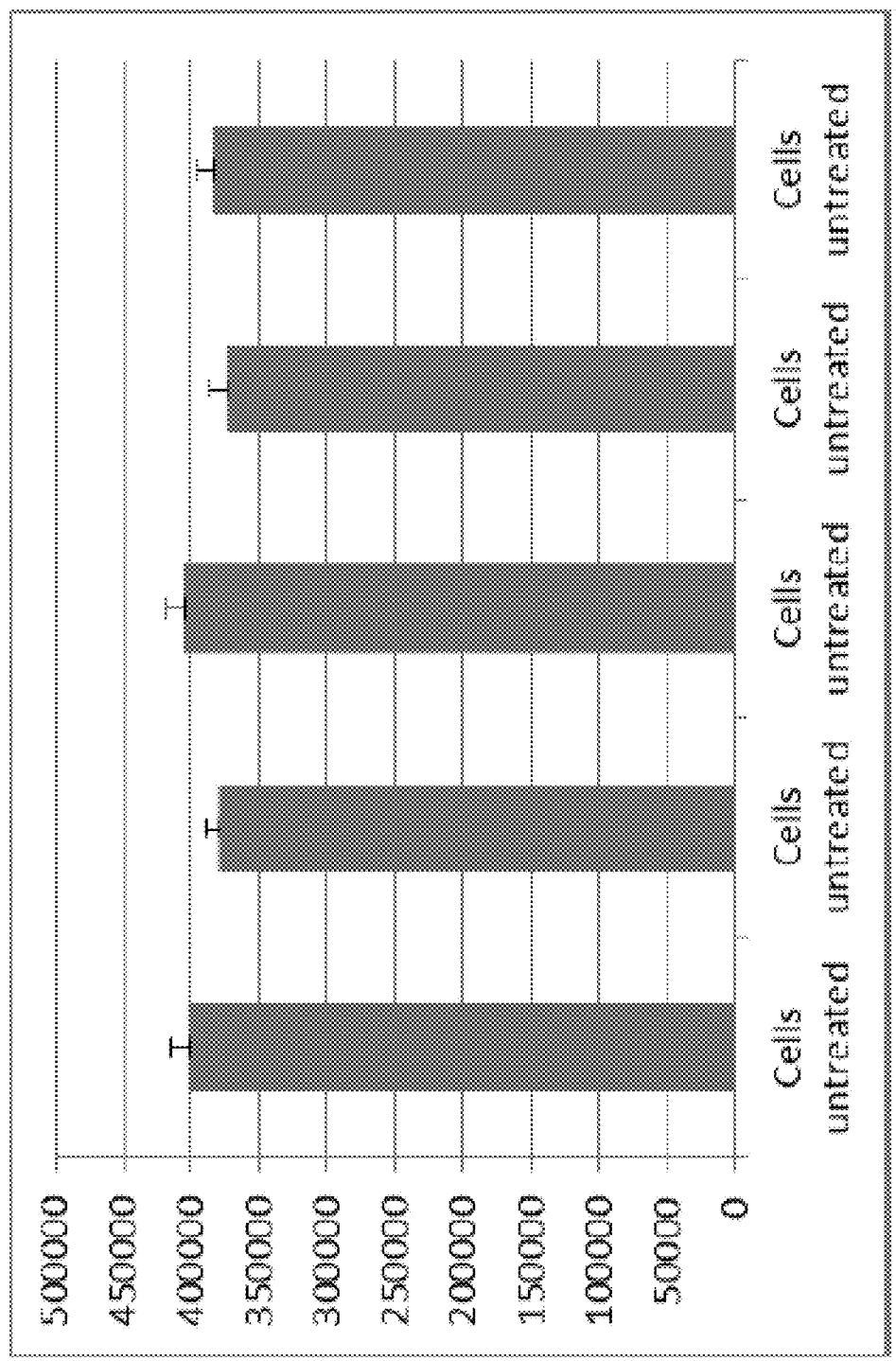
FIG. 18 is a graphical representation of the average number of untreated MCF-7 human breast cancer cells following a CellTiter Glo® assay at Day 0. The y-axis is relative light units (RLU).
Figure 19:
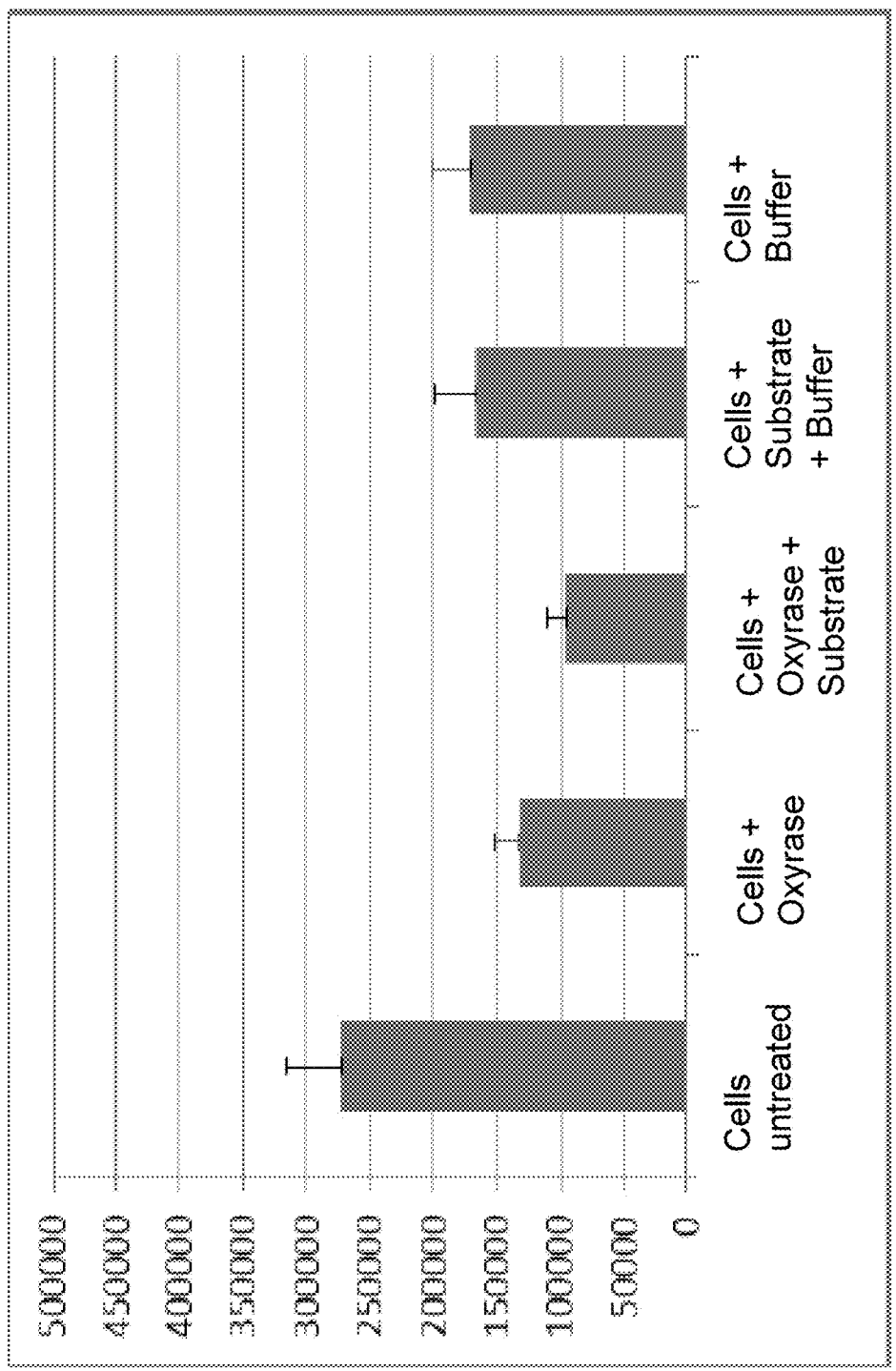
FIG. 19 is a graphical representation of the average number of MCF-7 human breast cancer cells untreated, cultured in Oxyrase® alone, cultured on substrate and Oxyrase®, cultured on substrate and buffer, and cultured in buffer following a CellTiter Glo® assay at Day 1. The y-axis is relative light units (RLU).
Figure 20:
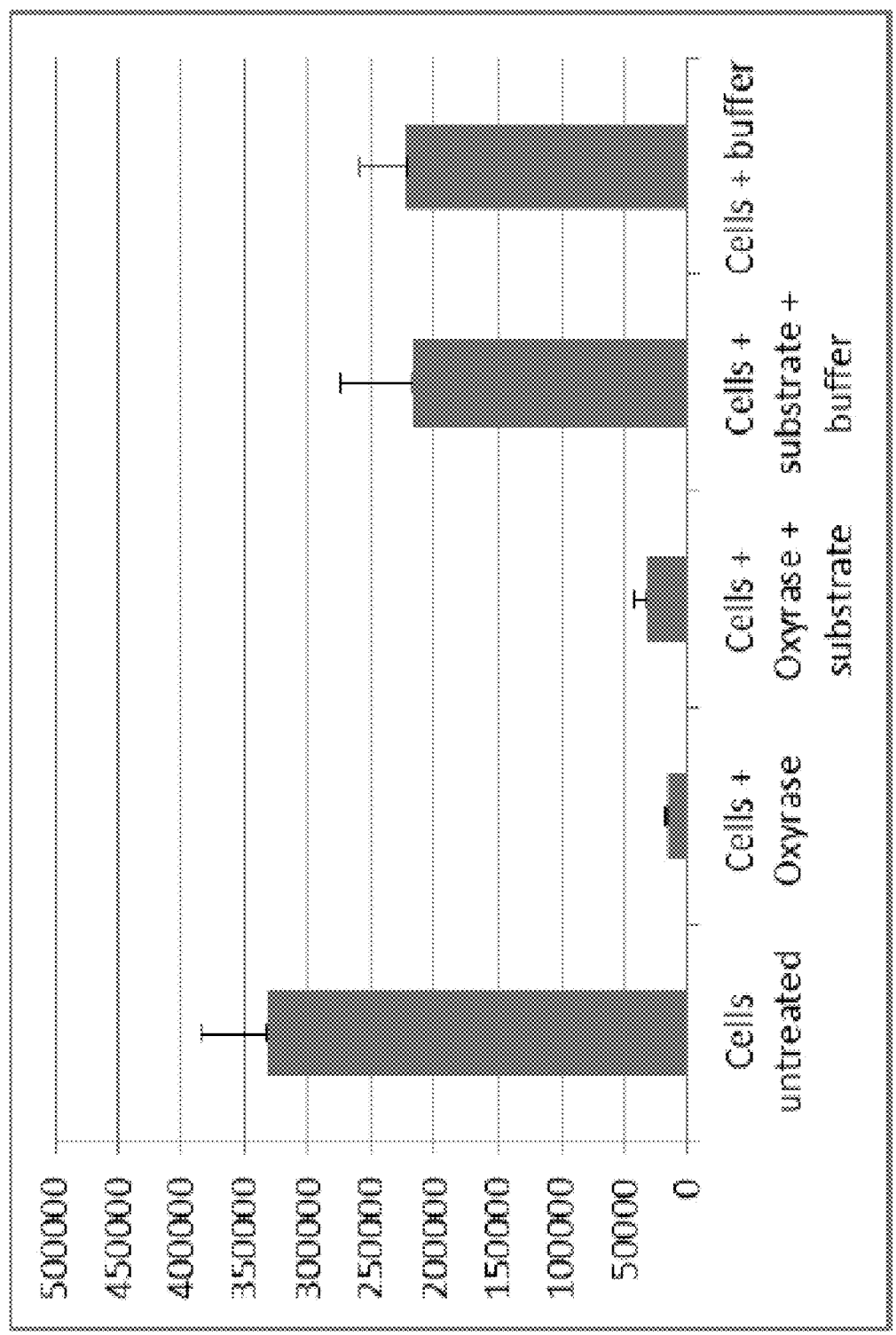
FIG. 20 is a graphical representation of the average number of MCF-7 human breast cancer cells untreated, cultured in Oxyrase® alone, cultured on substrate and Oxyrase®, cultured on substrate and buffer, and cultured in buffer following a CellTiter Glo® assay at Day 3. The y-axis is relative light units (RLU).
Figure 21:
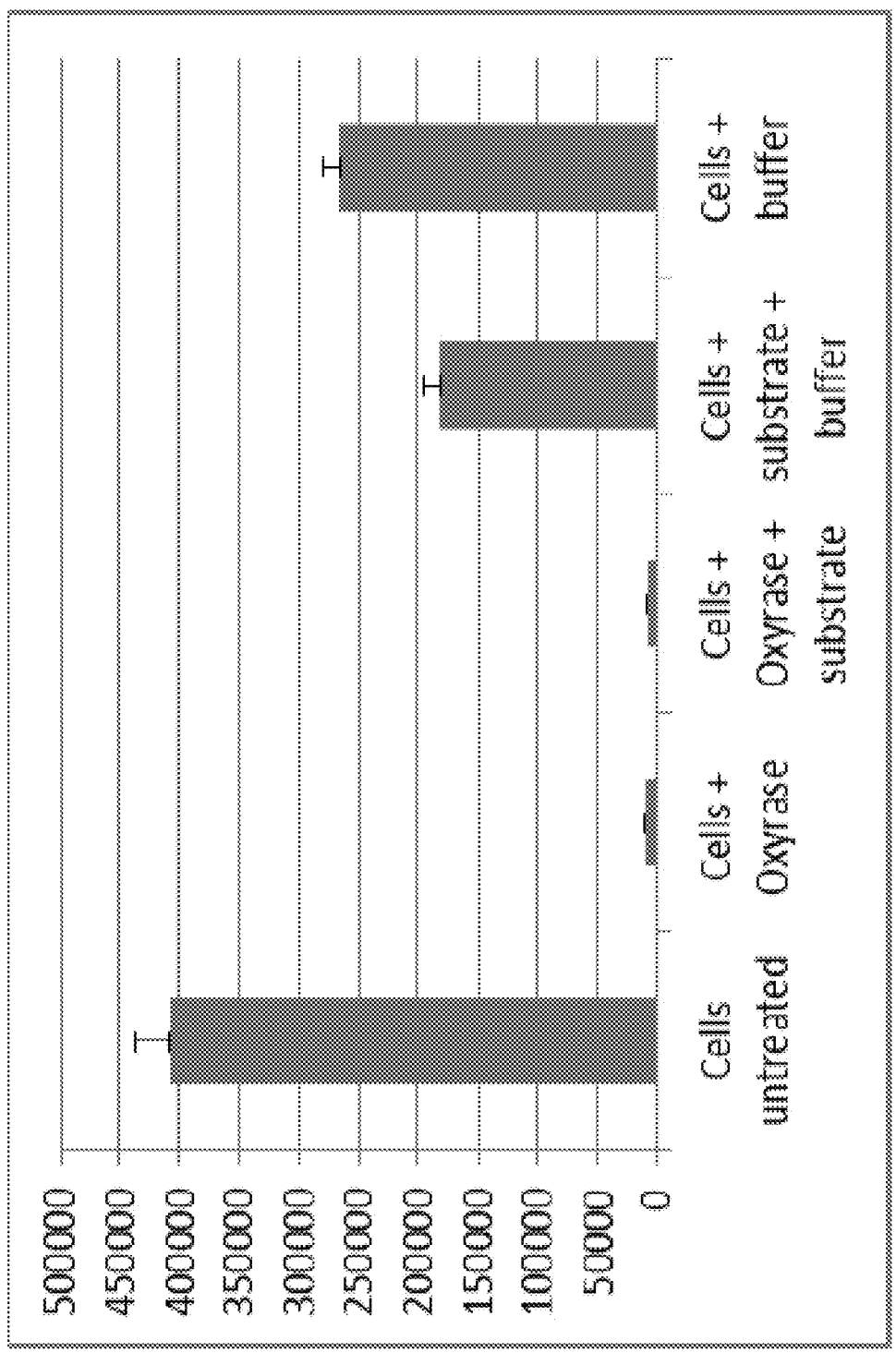
FIG. 21 is a graphical representation of the average number of MCF-7 human breast cancer cells untreated, cultured in Oxyrase® alone, cultured on substrate and Oxyrase®, cultured on substrate and buffer, and cultured in buffer following a CellTiter Glo® assay at Day 5. The y-axis is relative light units (RLU).
Figure 22:
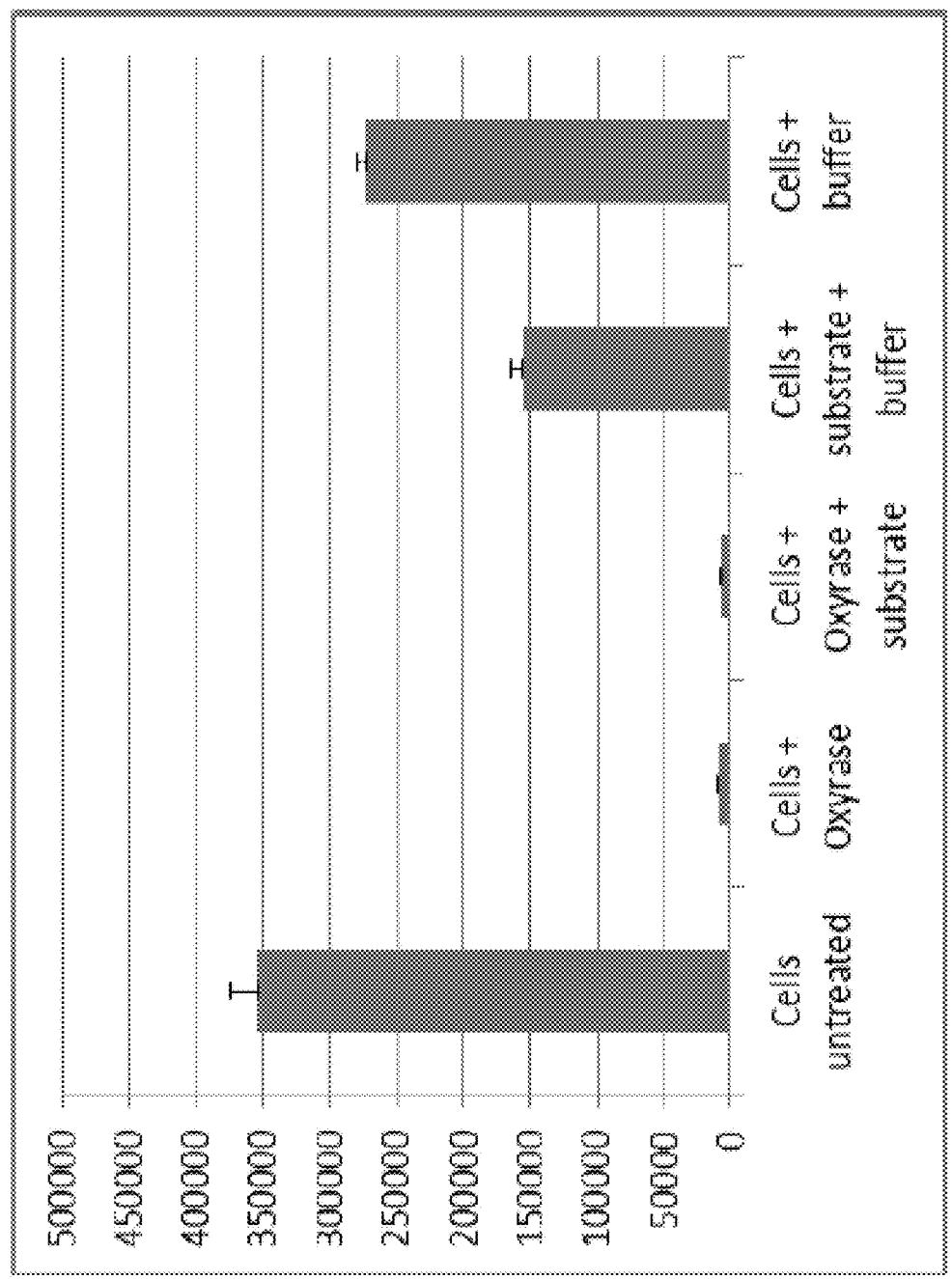
FIG. 22 is a graphical representation of the average number of MCF-7 human breast cancer cells untreated, cultured in Oxyrase® alone, cultured on substrate and Oxyrase®, cultured on substrate and buffer, and cultured in buffer following a CellTiter Glo® assay at Day 7. The y-axis is relative light units (RLU).
Figure 23:
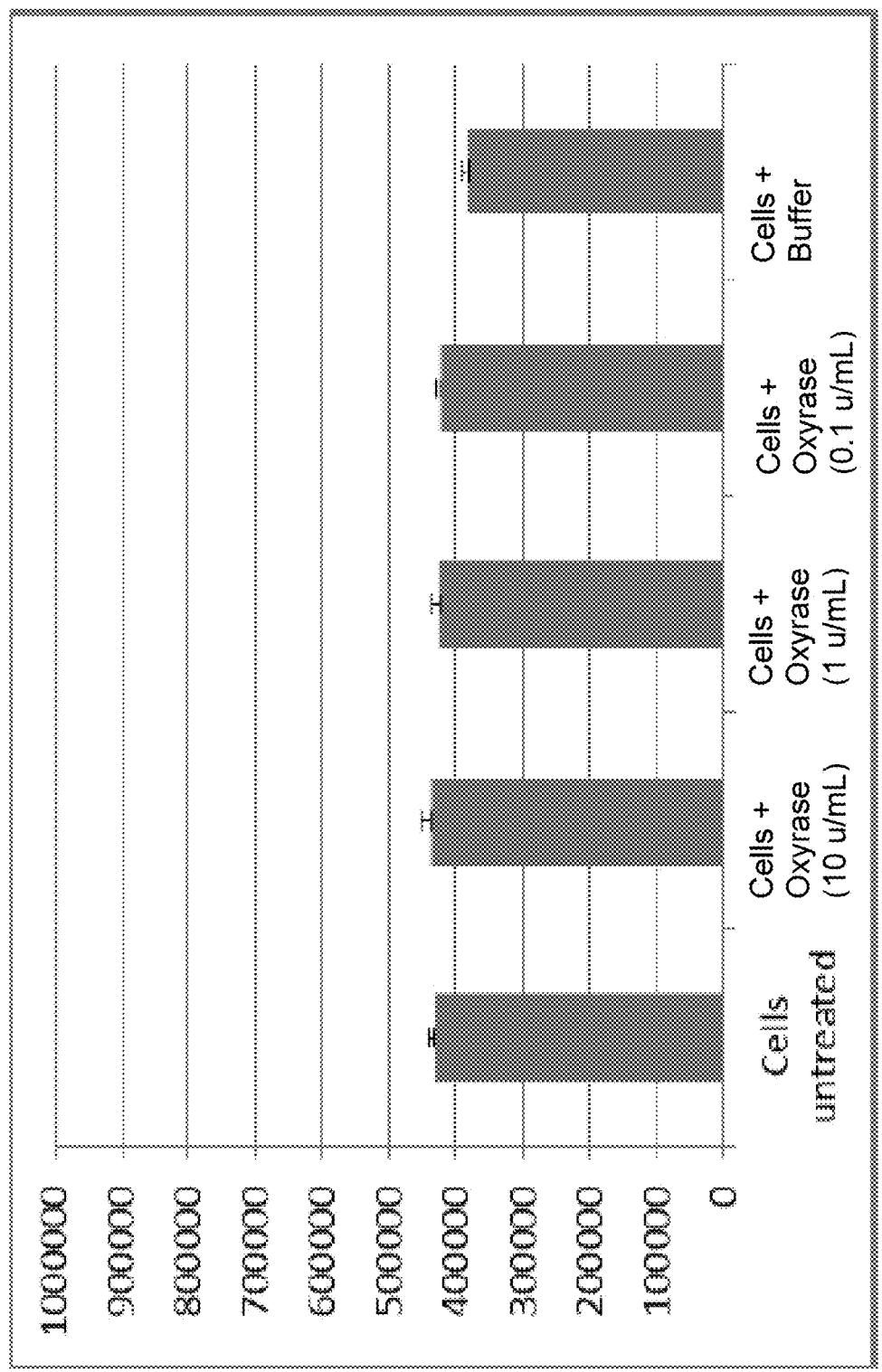
FIG. 23 is a graphical representation of the average number of untreated A375 human skin cancer cells following a CellTiter Glo® assay at Day 0. The y-axis is relative light units (RLU).
Figure 24:
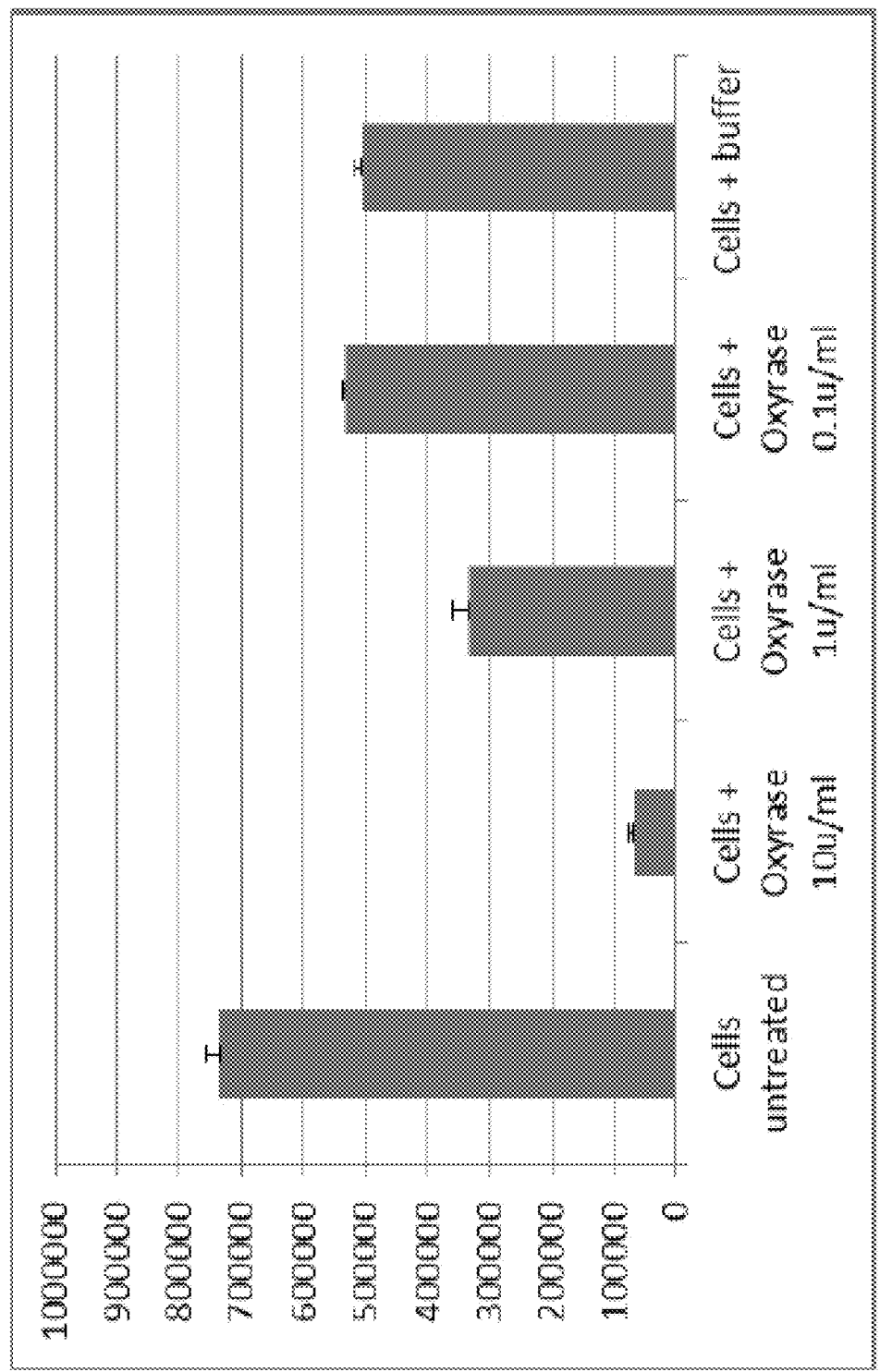
FIG. 24 is a graphical representation of the average number of A375 human skin cancer cells untreated, cultured in Oxyrase® alone, cultured on substrate and Oxyrase®, cultured on substrate and buffer, and cultured in buffer following a CellTiter Glo® assay at Day 1. The y-axis is relative light units (RLU).
Figure 25:
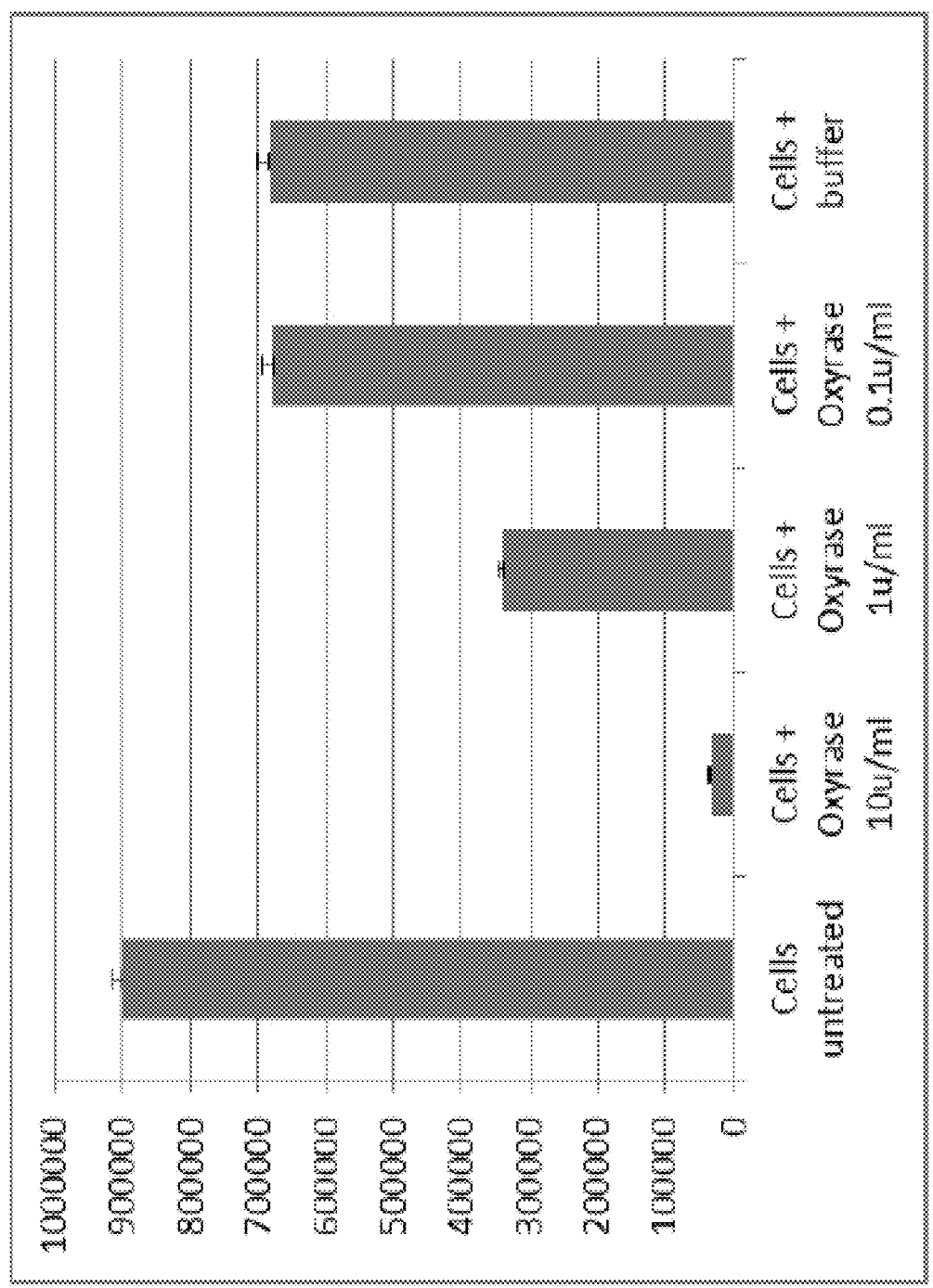
FIG. 25 is a graphical representation of the average number of A375 human skin cancer cells untreated, cultured in Oxyrase® alone, cultured on substrate and Oxyrase®, cultured on substrate and buffer, and cultured in buffer following a CellTiter Glo® assay at Day 3. The y-axis is relative light units (RLU).
Figure 26:
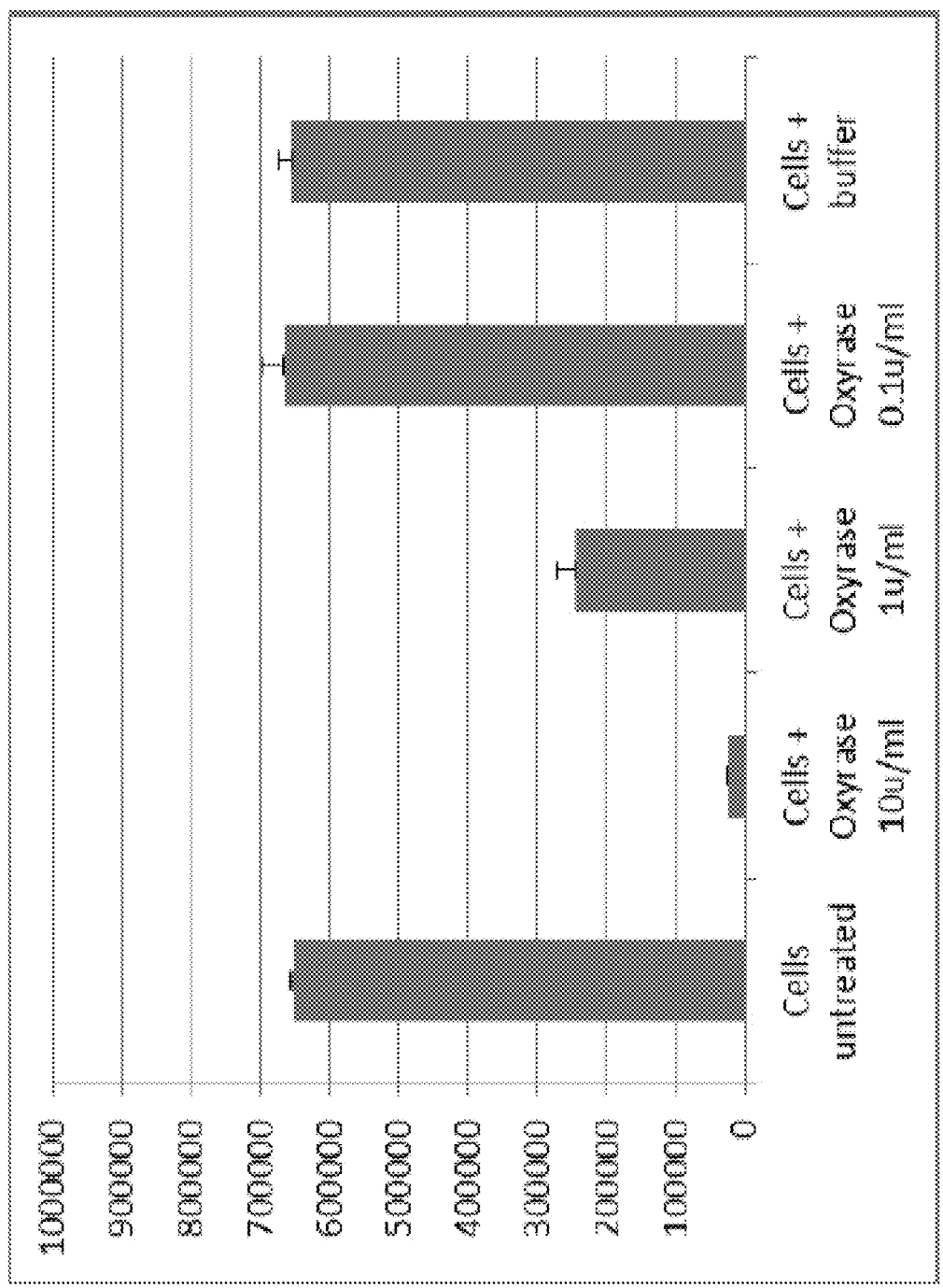
FIG. 26 is a graphical representation of the average number of A375 human skin cancer cells untreated, cultured in Oxyrase® alone, cultured on substrate and Oxyrase®, cultured on substrate and buffer, and cultured in buffer following a CellTiter Glo® assay at Day 5. The y-axis is relative light units (RLU).
Figure 27:
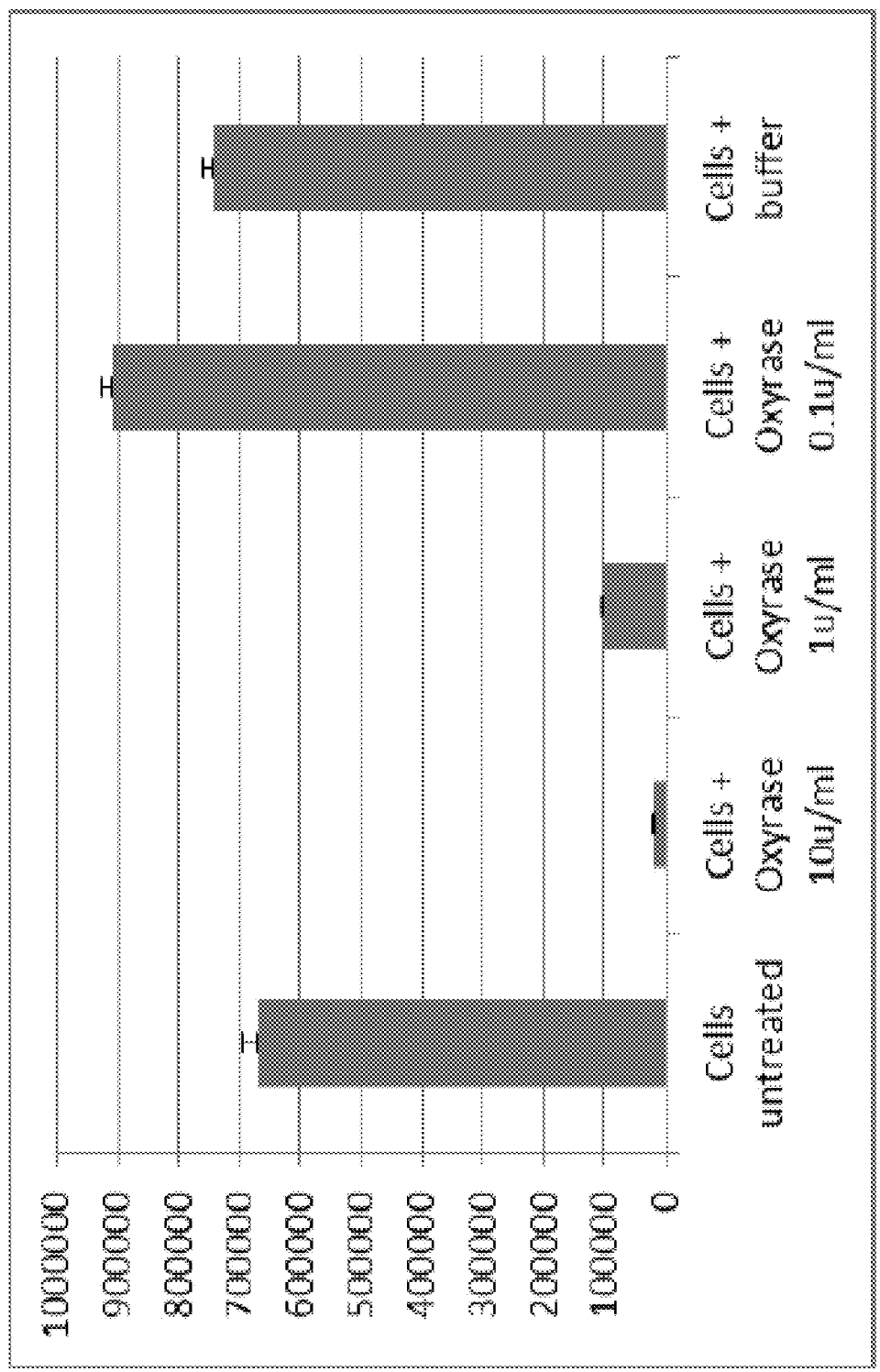
FIG. 27 is a graphical representation of the average number of A375 human skin cancer cells untreated, cultured in Oxyrase® alone, cultured on substrate and Oxyrase®, cultured on substrate and buffer, and cultured in buffer following a CellTiter Glo® assay at Day 7. The y-axis is relative light units (RLU).
Figure 28:
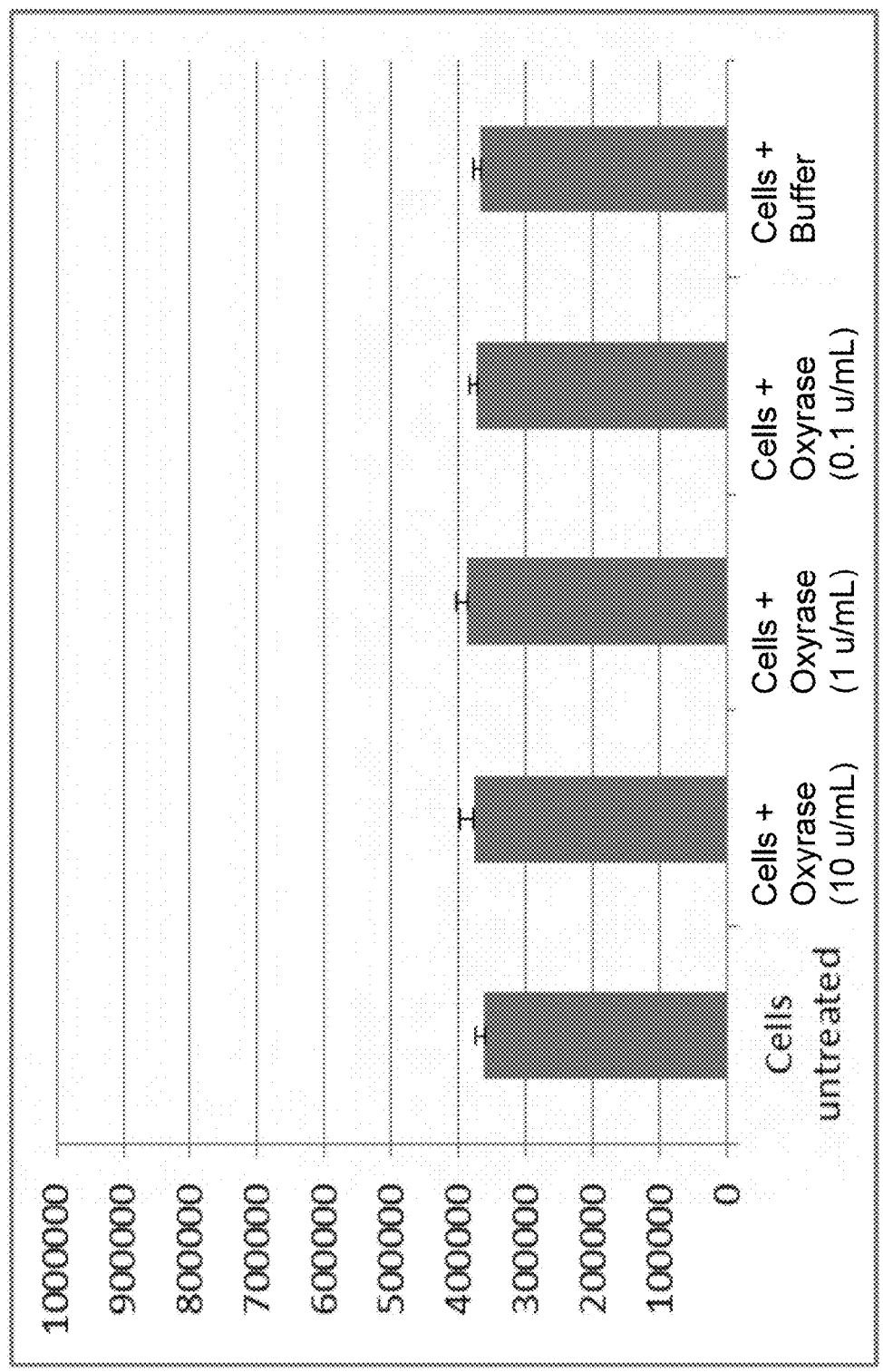
FIG. 28 is a graphical representation of the average number of untreated A549 human lung cancer cells following a CellTiter Glo® assay at Day 0. The y-axis is relative light units (RLU).
Figure 29:
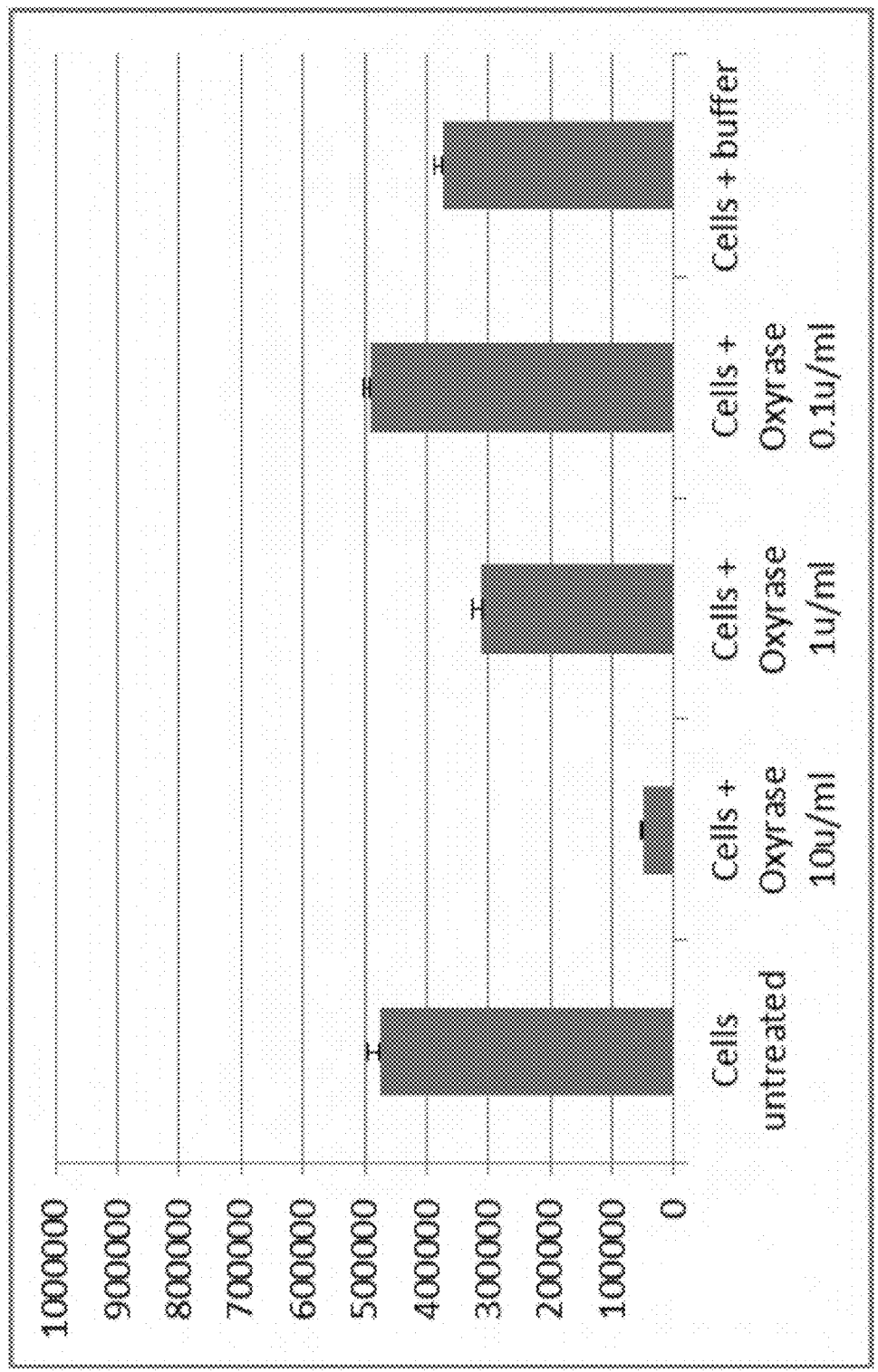
FIG. 29 is a graphical representation of the average number of A549 human lung cancer cells untreated, cultured in Oxyrase® alone, cultured on substrate and Oxyrase®, cultured on substrate and buffer, and cultured in buffer following a CellTiter Glo® assay at Day 1. The y-axis is relative light units (RLU).
Figure 30:
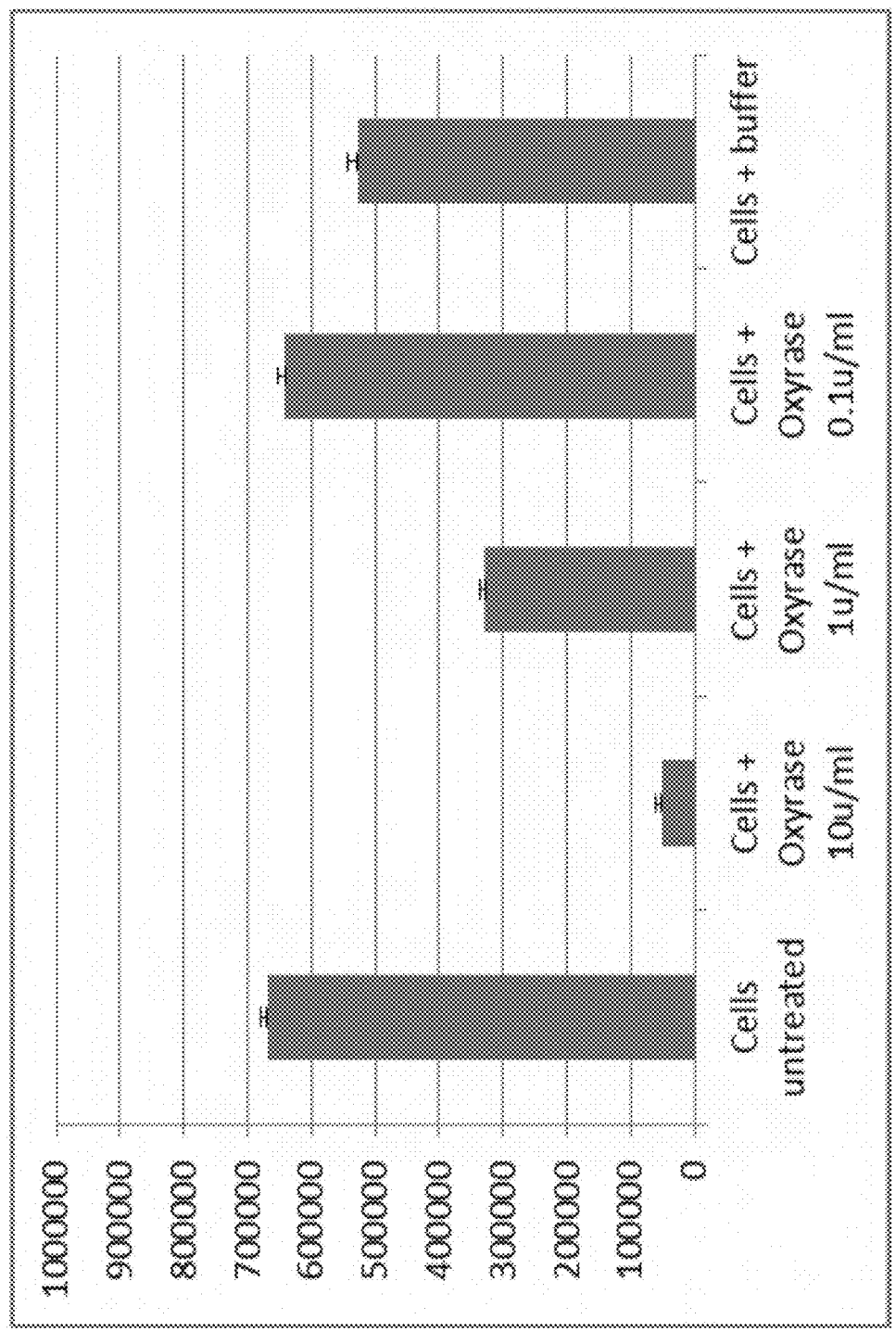
FIG. 30 is a graphical representation of the average number of A549 human lung cancer cells untreated, cultured in Oxyrase® alone, cultured on substrate and Oxyrase®, cultured on substrate and buffer, and cultured in buffer following a CellTiter Glo® assay at Day 3. The y-axis is relative light units (RLU).
Figure 31:
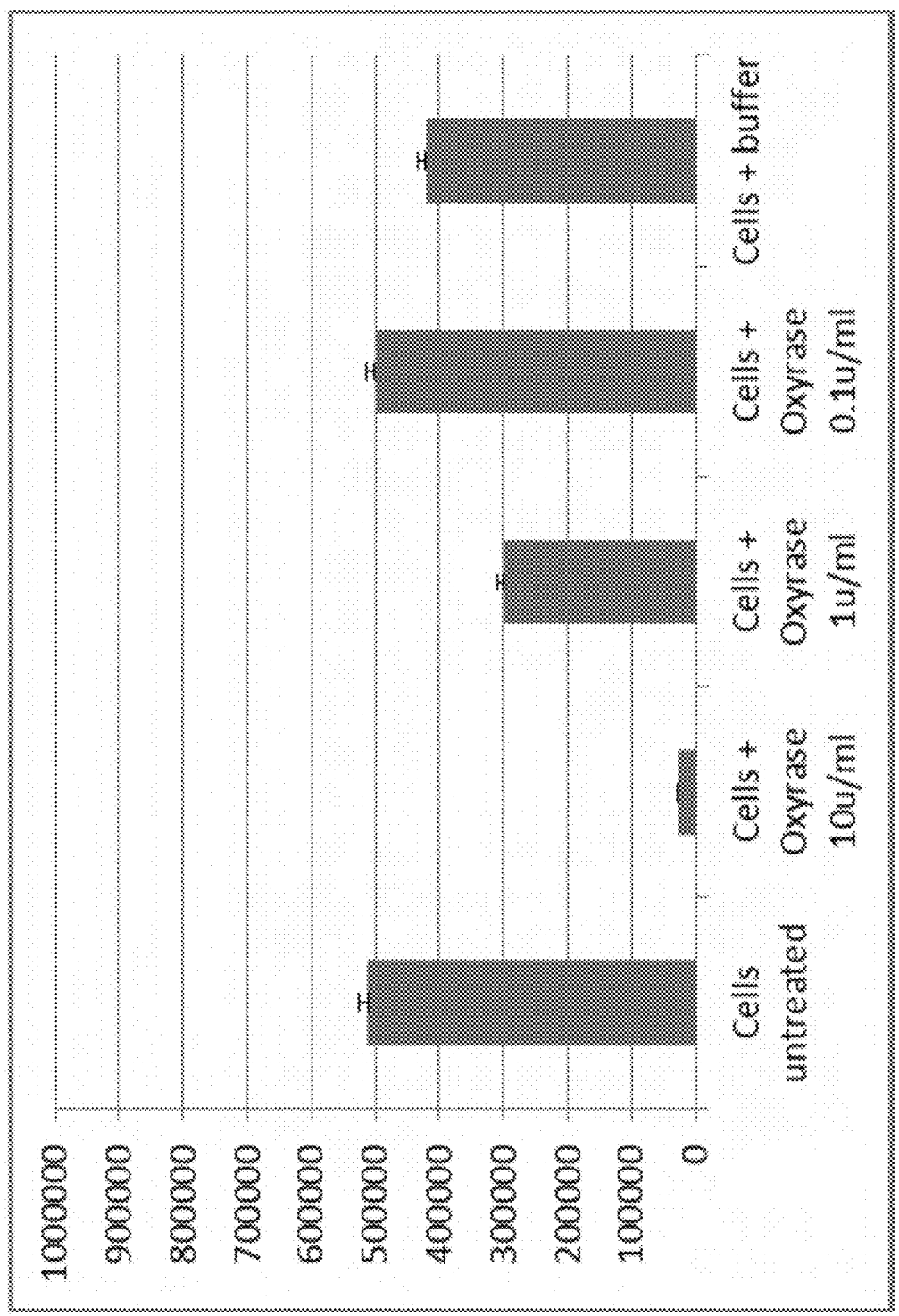
FIG. 31 is a graphical representation of the average number of A549 human lung cancer cells untreated, cultured in Oxyrase® alone, cultured on substrate and Oxyrase®, cultured on substrate and buffer, and cultured in buffer following a CellTiter Glo® assay at Day 5. The y-axis is relative light units (RLU).
Figure 32:
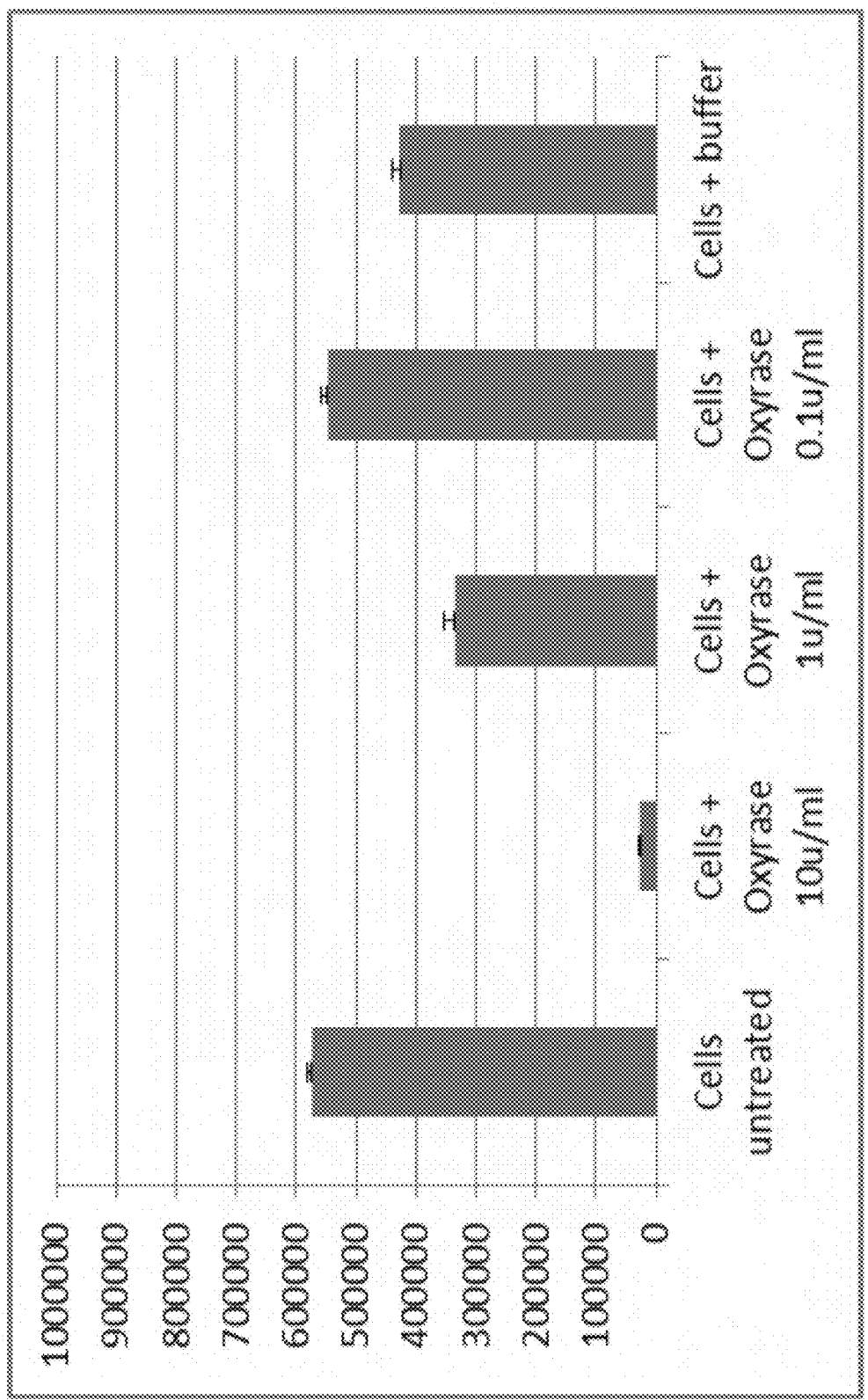
FIG. 32 is a graphical representation of the average number of A549 human lung cancer cells untreated, cultured in Oxyrase® alone, cultured on substrate and Oxyrase®, cultured on substrate and buffer, and cultured in buffer following a CellTiter Glo® assay at Day 7. The y-axis is relative light units (RLU).
Figure 33:
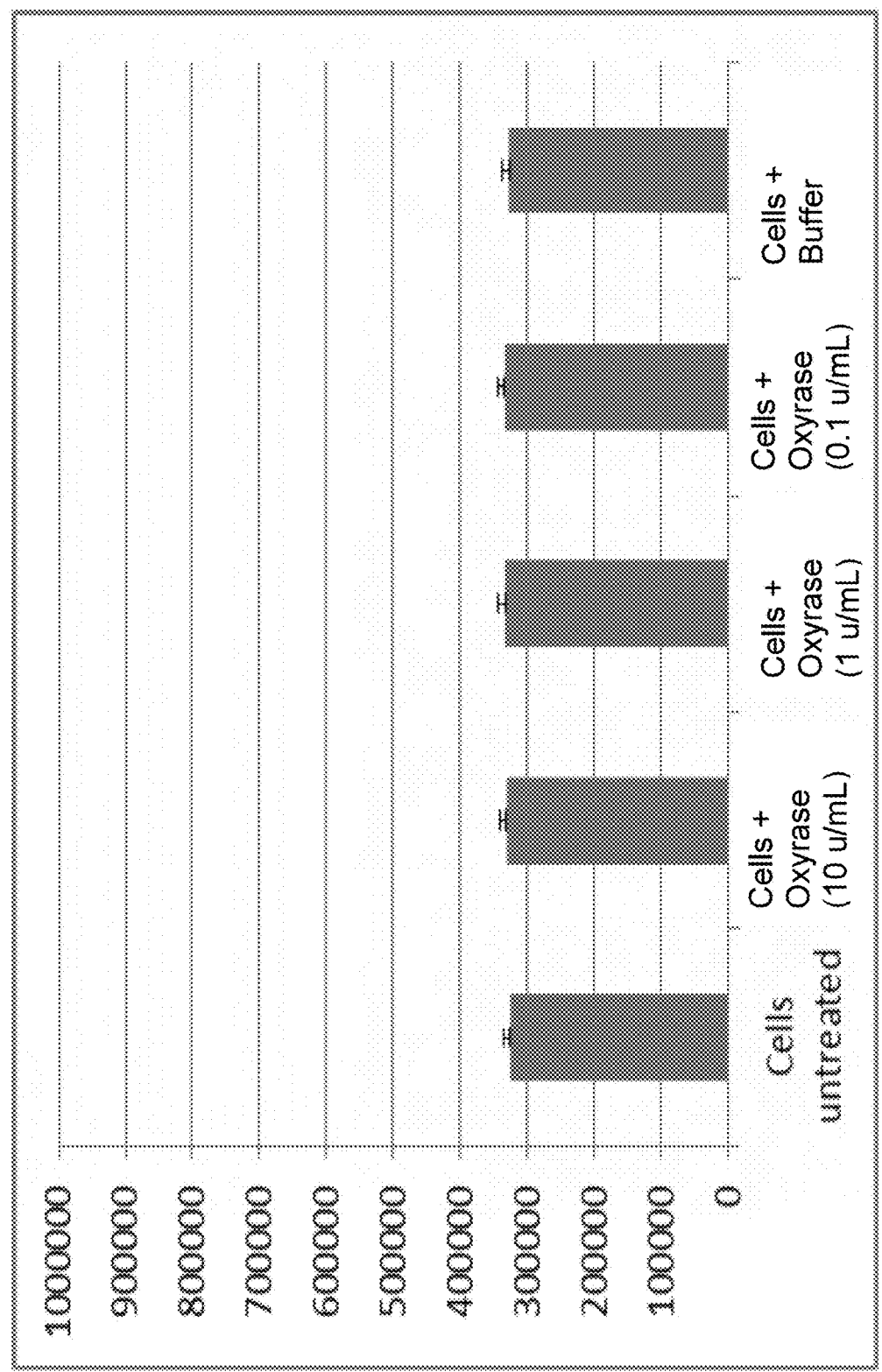
FIG. 33 is a graphical representation of the average number of untreated HT29 human colon cancer cells following a CellTiter Glo® assay at Day 0. The y-axis is relative light units (RLU).
Figure 34:
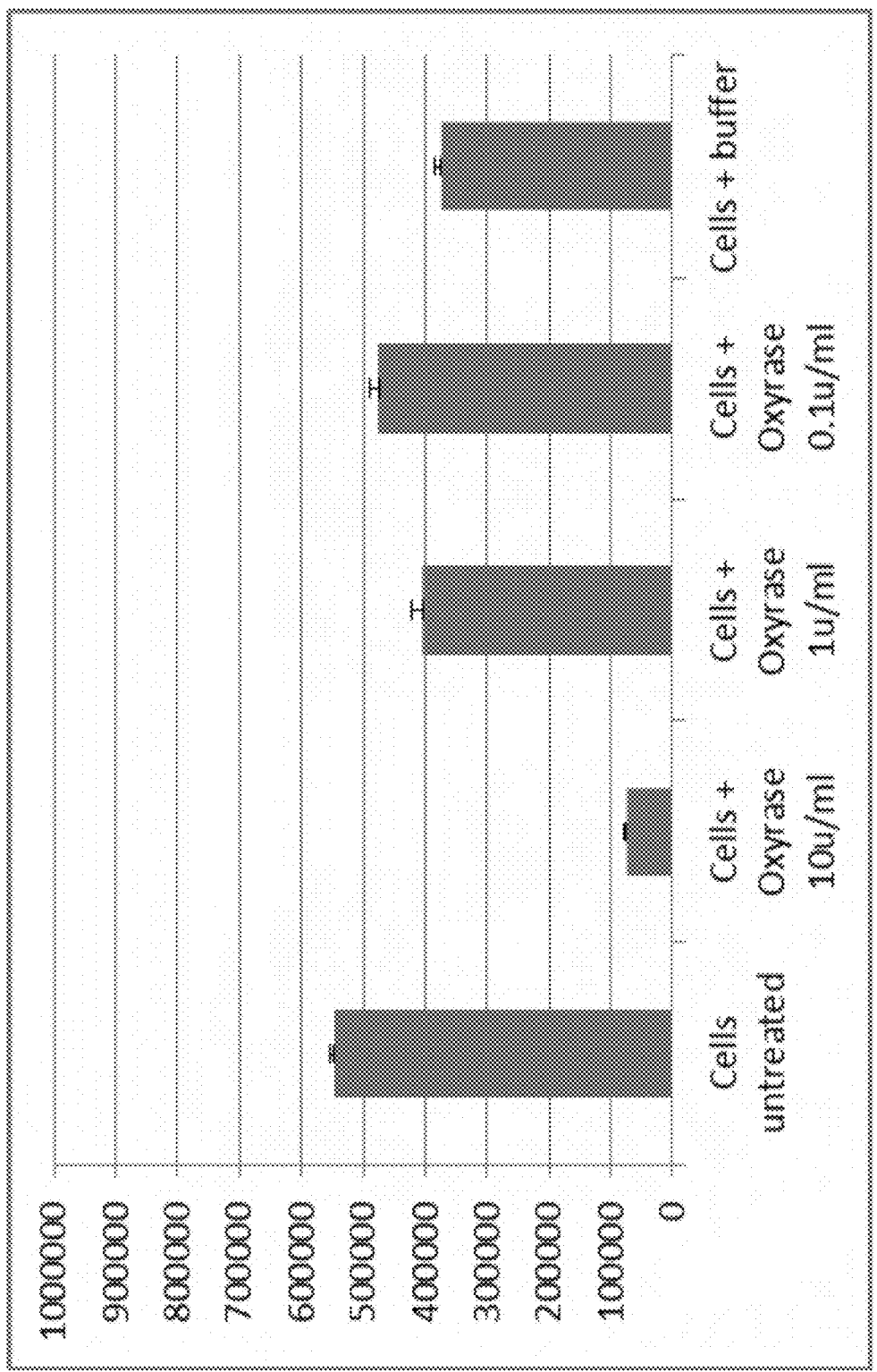
FIG. 34 is a graphical representation of the average number of HT29 human colon cancer cells untreated, cultured in Oxyrase® alone, cultured on substrate and Oxyrase®, cultured on substrate and buffer, and cultured in buffer following a CellTiter Glo® assay at Day 1. The y-axis is relative light units (RLU).
Figure 35:
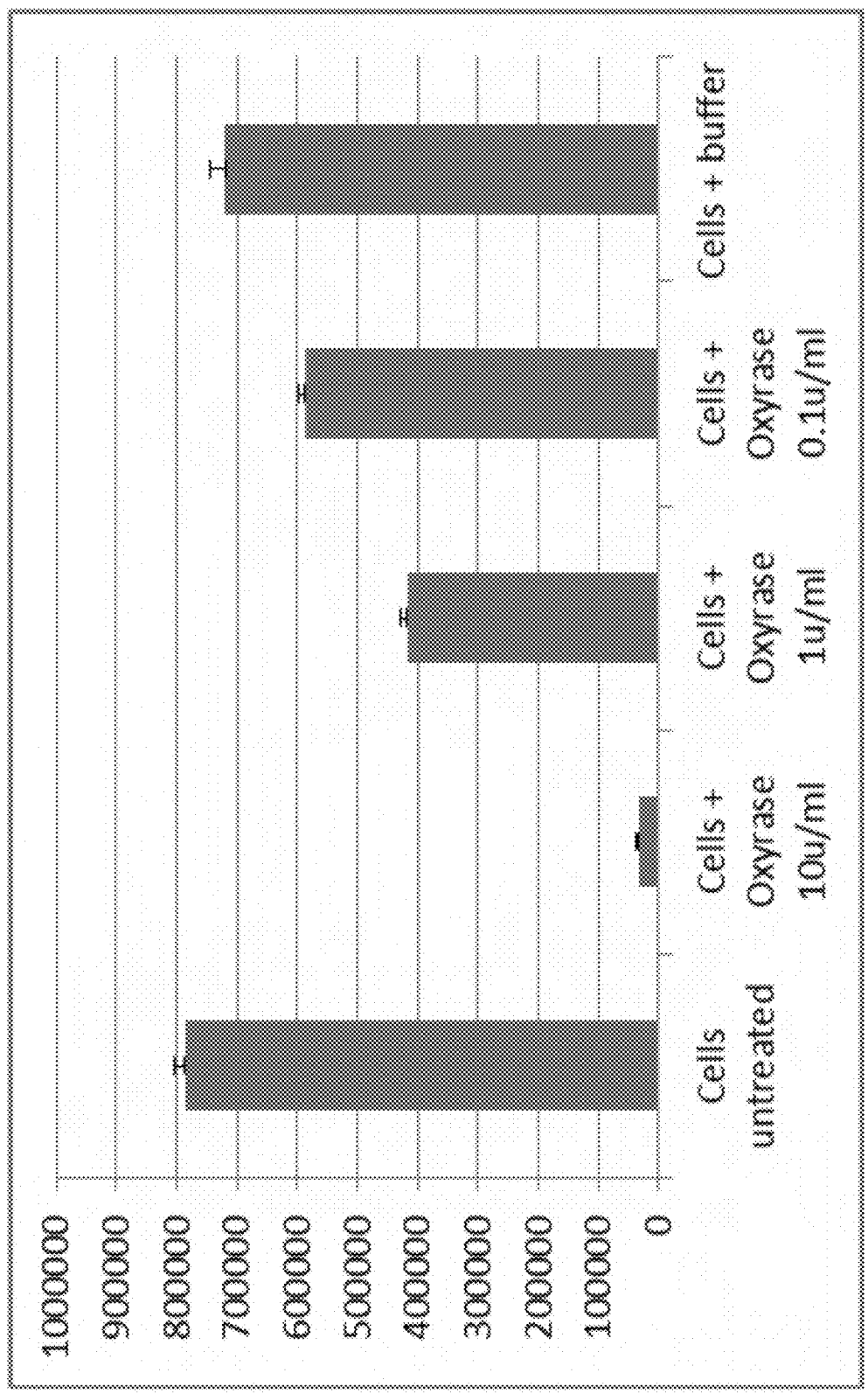
FIG. 35 is a graphical representation of the average number of HT29 human colon cancer cells untreated, cultured in Oxyrase® alone, cultured on substrate and Oxyrase®, cultured on substrate and buffer, and cultured in buffer following a CellTiter Glo® assay at Day 3. The y-axis is relative light units (RLU).
Figure 36:
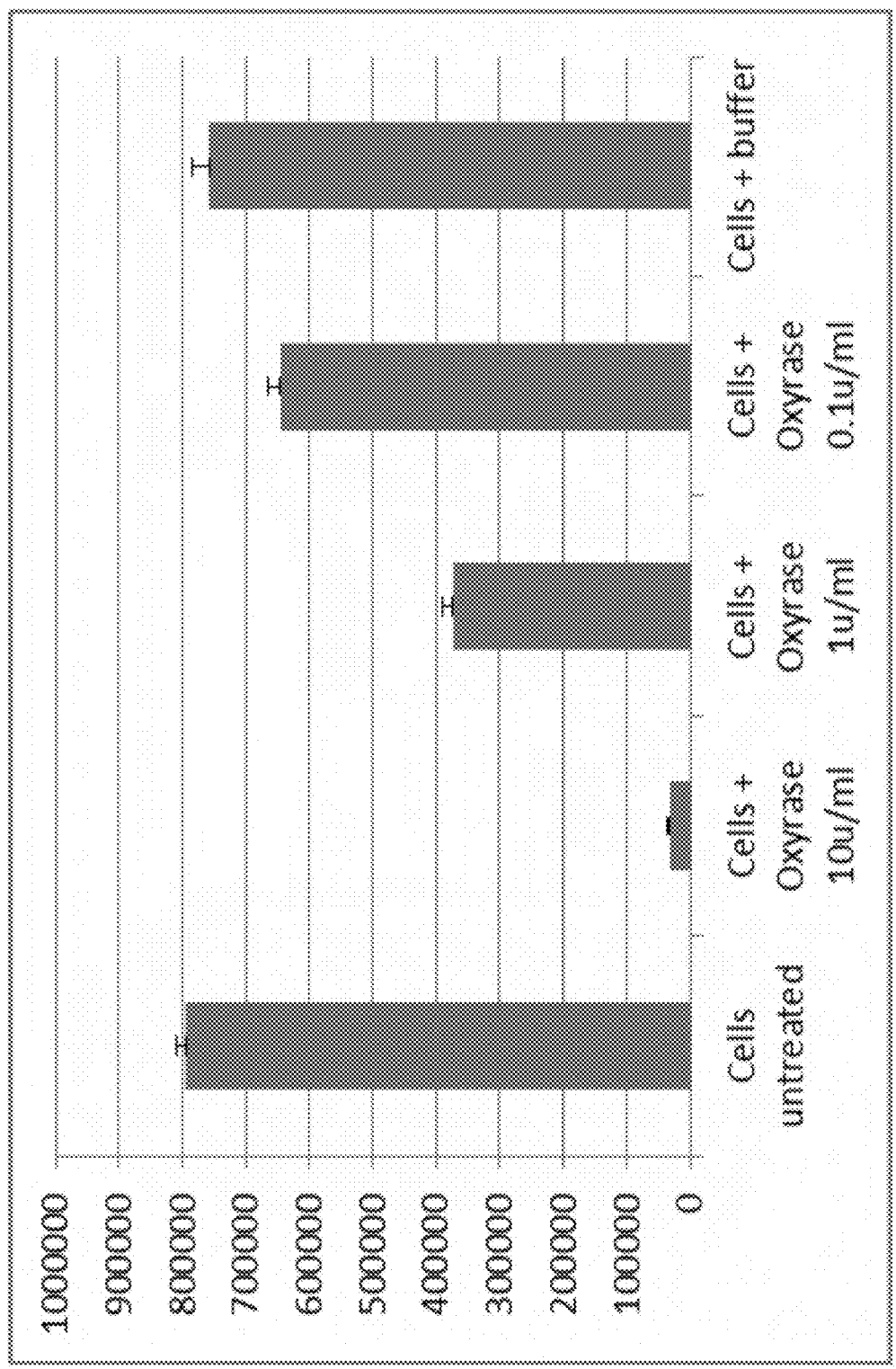
FIG. 36 is a graphical representation of the average number of HT29 human colon cancer cells untreated, cultured in Oxyrase® alone, cultured on substrate and Oxyrase®, cultured on substrate and buffer, and cultured in buffer following a CellTiter Glo® assay at Day 5. The y-axis is relative light units (RLU).
Figure 37:
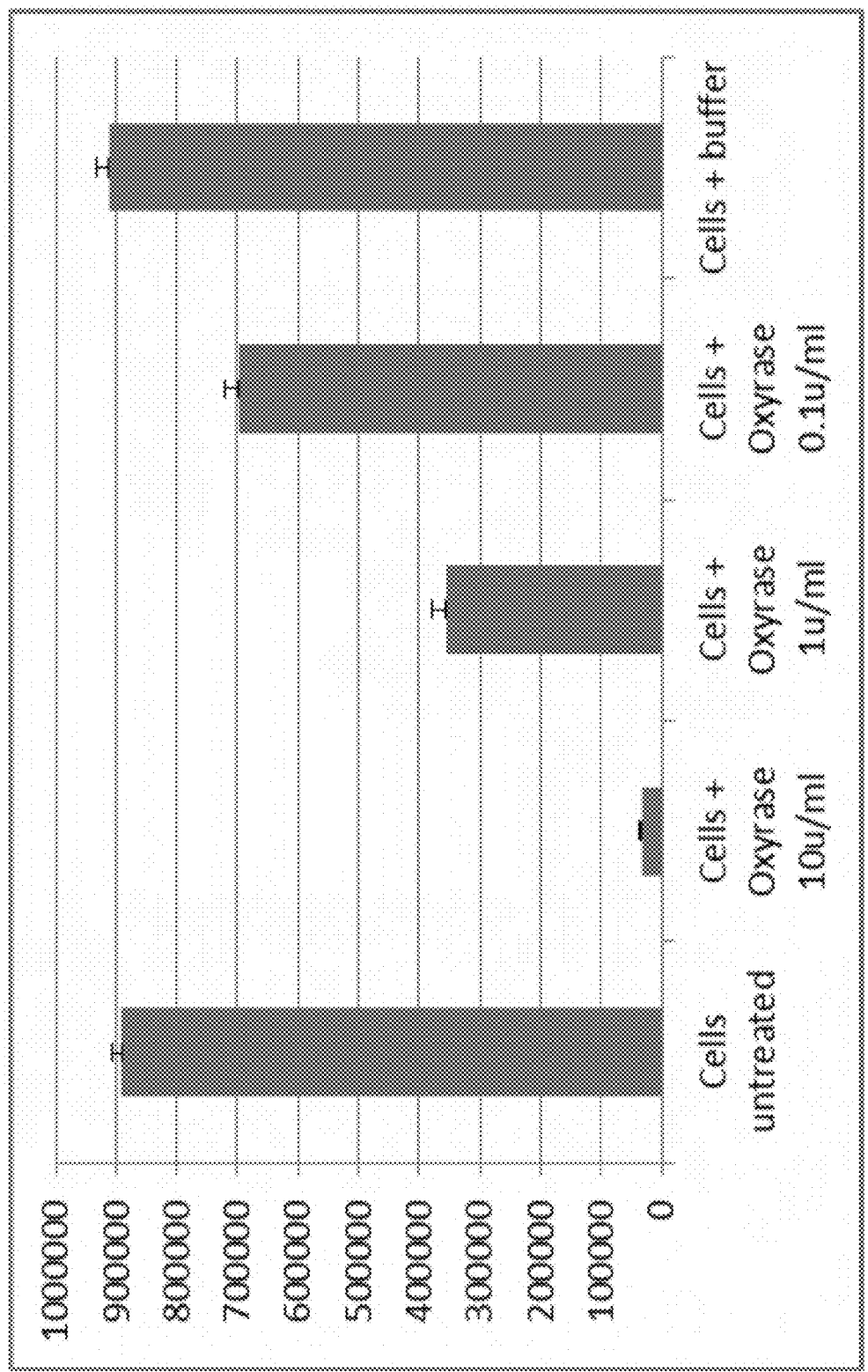
FIG. 37 is a graphical representation of the average number of HT29 human colon cancer cells untreated, cultured in Oxyrase® alone, cultured on substrate and Oxyrase®, cultured on substrate and buffer, and cultured in buffer following a CellTiter Glo® assay at Day 7. The y-axis is relative light units (RLU).
Figure 38:
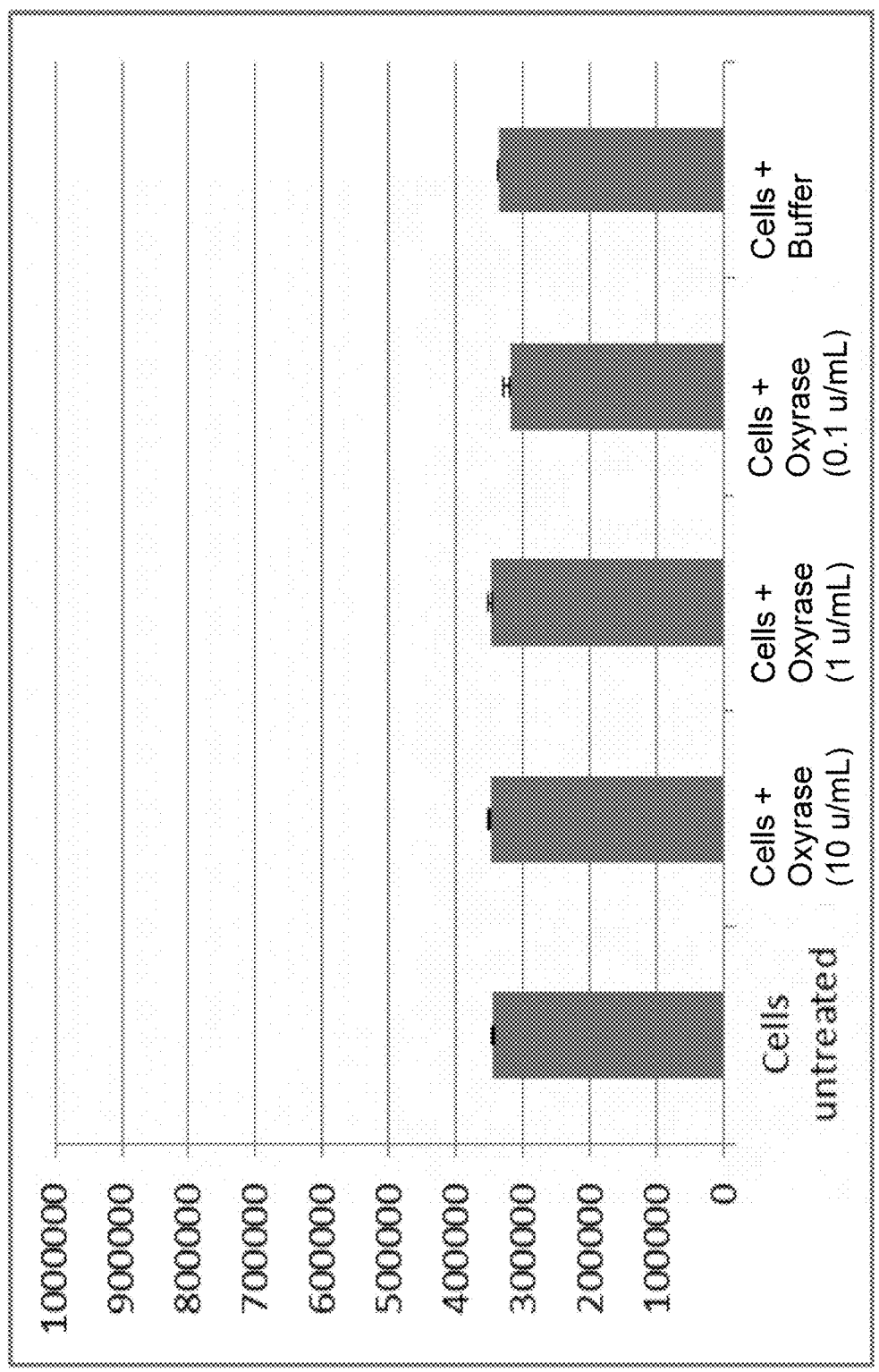
FIG. 38 is a graphical representation of the average number of untreated U87-MG human brain cancer cells following a CellTiter Glo® assay at Day 0. The y-axis is relative light units (RLU).
Figure 39:
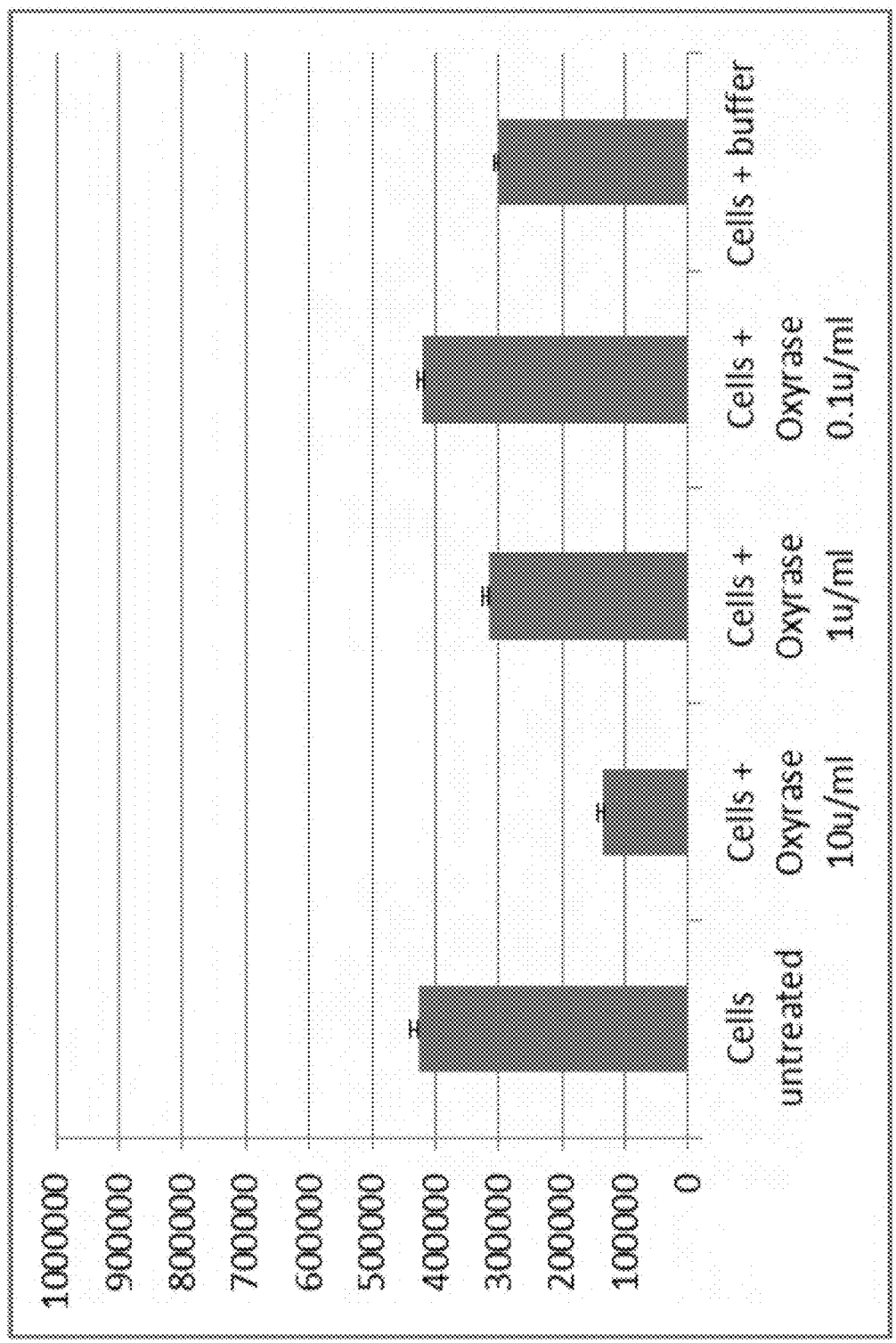
FIG. 39 is a graphical representation of the average number of U87-MG human brain cancer cells untreated, cultured in Oxyrase® alone, cultured on substrate and Oxyrase®, cultured on substrate and buffer, and cultured in buffer following a CellTiter Glo® assay at Day 1. The y-axis is relative light units (RLU).
Figure 40:
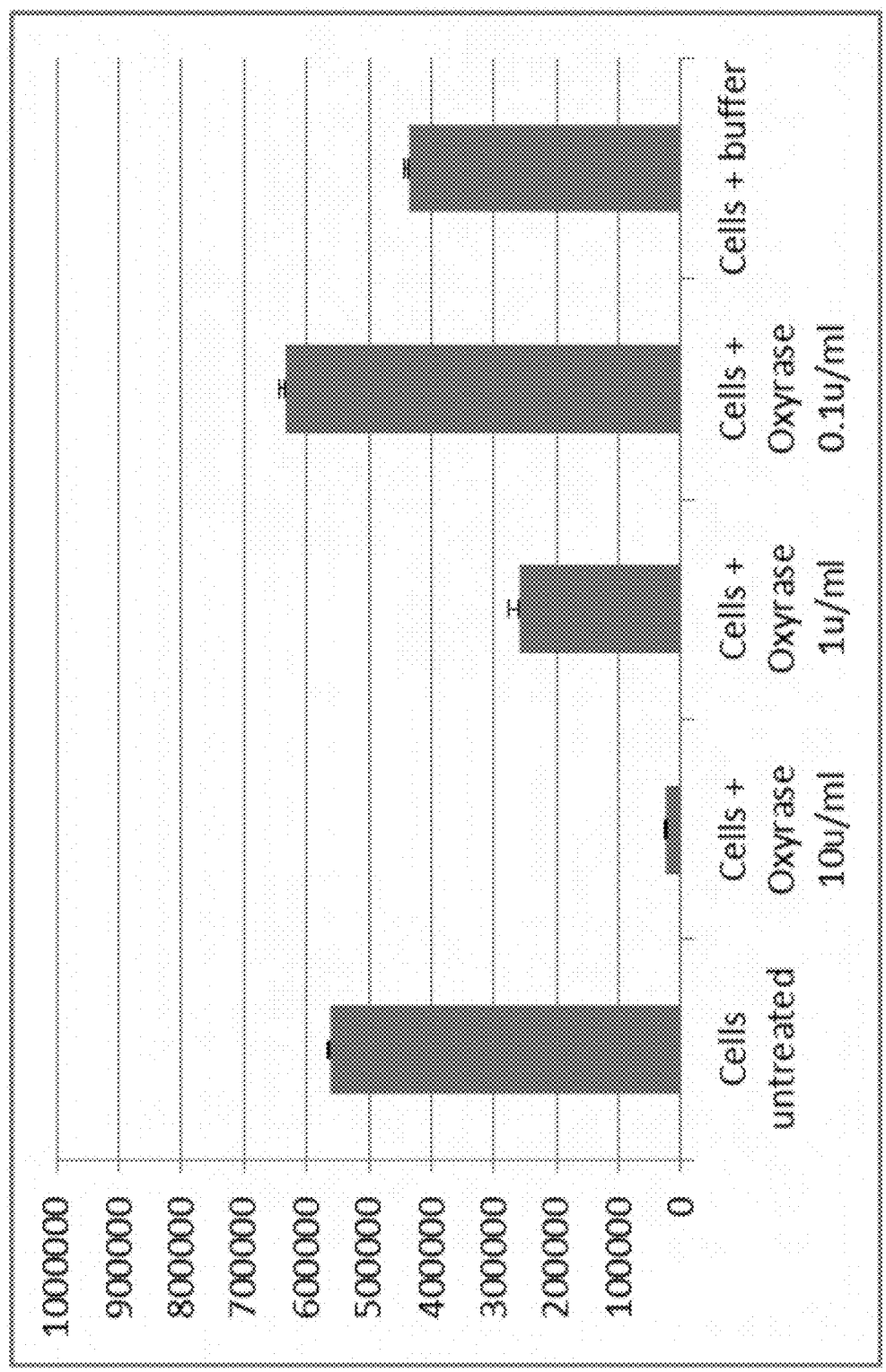
FIG. 40 is a graphical representation of the average number of U87-MG human brain cancer cells untreated, cultured in Oxyrase® alone, cultured on substrate and Oxyrase®, cultured on substrate and buffer, and cultured in buffer following a CellTiter Glo® assay at Day 3. The y-axis is relative light units (RLU).
Figure 41:
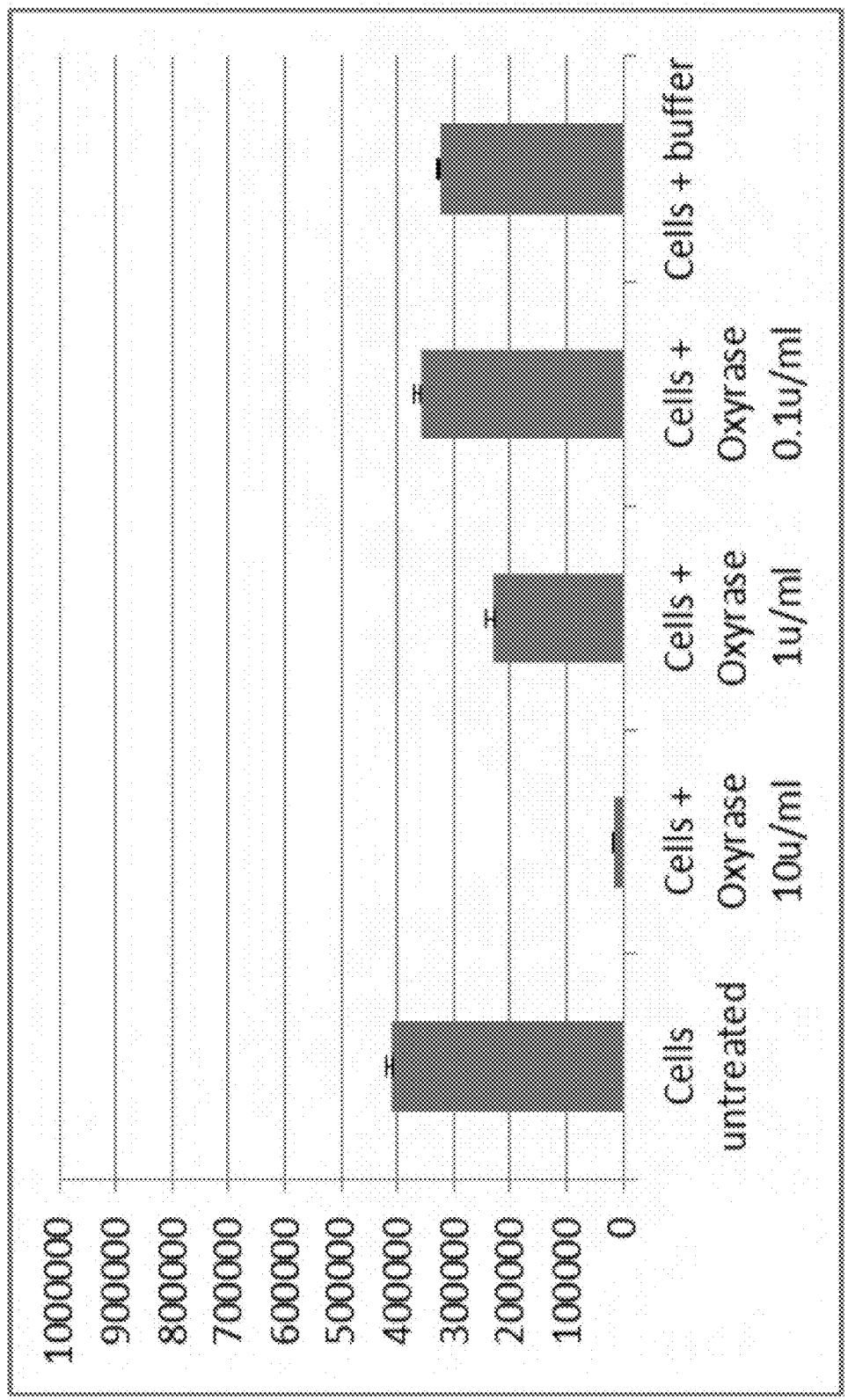
FIG. 41 is a graphical representation of the average number of U87-MG human brain cancer cells untreated, cultured in Oxyrase® alone, cultured on substrate and Oxyrase®, cultured on substrate and buffer, and cultured in buffer following a CellTiter Glo® assay at Day 5. The y-axis is relative light units (RLU).
Figure 42:
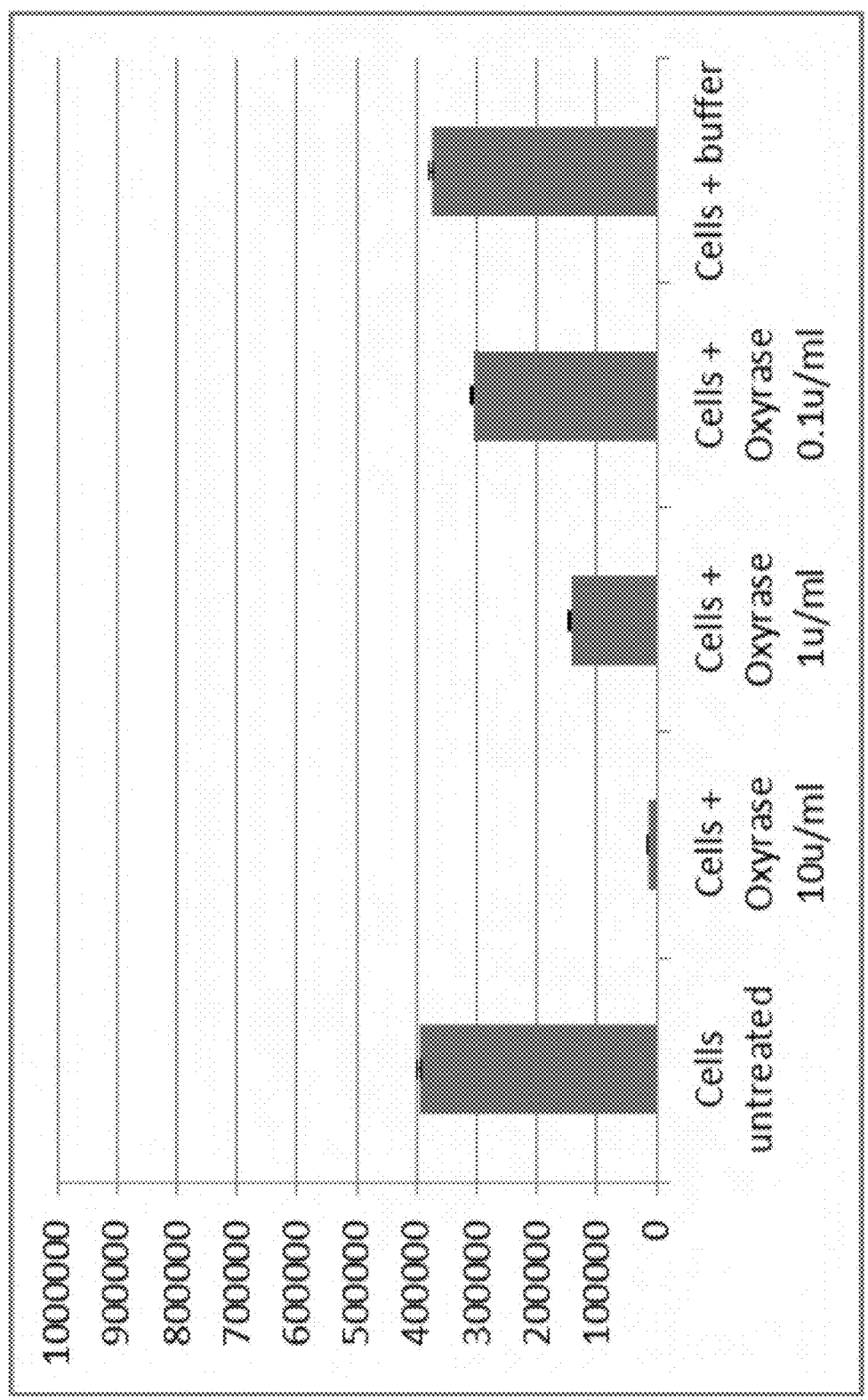
FIG. 42 is a graphical representation of the average number of U87-MG human brain cancer cells untreated, cultured in Oxyrase® alone, cultured on substrate and Oxyrase®, cultured on substrate and buffer, and cultured in buffer following a CellTiter Glo® assay at Day 7. The y-axis is relative light units (RLU).

In the ViCell assay, Oxyrase® with or without its substrate showed significant aggregation. The aggregates were in the same size range as the cells: 5 to 50 microns. The machine was unable to differentiate between the cells and the aggregates. Thus, the data was inconclusive. A graphical representation of the results from the ViCell assay is represented in FIG. 15. FIG. 16 is a ViCell image of untreated MCF-7 human breast cancer cells on day 1, while FIG. 17 is a ViCell image of MCF-7 cells treated with Oxyrase® and substrate on day 1.

According to the CellTiter Glo® assay, there was an approximately 90% reduction in ATP levels in Oxyrase® treated wells with or without the addition of substrate. Tables 2-6 below indicate the number of cells on days 0, 1, 3, 5 and 7 as well as the average numbers of cells per treatment, as measured by relative light units (RLU), and the standard deviations. These tables are graphically represented in FIGS. 18-22.

TABLE 2

MCF-7 Human Breast Cancer Cell Plates at Day 0

|  | Untreated cells | Oxyrase ® (20 u/mL) | Oxyrase ® + Substrate | Substrate + Buffer | Buffer |
|---|---|---|---|---|---|
|  | 371093 | 355759 | 379583 | 340018 | 356148 |
|  | 414028 | 376651 | 398374 | 370831 | 389386 |
|  | 412556 | 386376 | 423569 | 395464 | 388263 |
|  | 418242 | 388291 | 421712 | 380015 | 402117 |
|  | 402287 | 391129 | 410350 | 376738 | 388115 |
|  | 385974 | 381025 | 397149 | 379461 | 378447 |
| Average | 400697 | 379872 | 405123 | 373755 | 383746 |
| Std. Dev. | 14775 | 9111 | 13421 | 12220 | 10966 |

TABLE 3

MCF-7 Human Breast Cancer Cell Plates at Day 1

|  | Untreated cells | Oxyrase ® (20 u/mL) | Oxyrase ® + Substrate | Substrate + Buffer | Buffer |
|---|---|---|---|---|---|
|  | 327693 | 136863 | 94230 | 224766 | 226189 |
|  | 328463 | 151853 | 94142 | 187489 | 192574 |
|  | 278221 | 146289 | 126401 | 171303 | 164113 |
|  | 251612 | 135693 | 92133 | 142850 | 149039 |
|  | 218167 | 130497 | 83623 | 136132 | 147571 |
|  | 234579 | 89453 | 83304 | 135475 | 147751 |
| Average | 273123 | 131775 | 95639 | 166336 | 171206 |
| Std. Dev. | 42885 | 20198 | 14488 | 32410 | 29241 |

TABLE 4

MCF-7 Human Breast Cancer Cell Plates at Day 3

|  | Untreated cells | Oxyrase ® (20 u/mL) | Oxyrase ® + Substrate | Substrate + Buffer | Buffer |
|---|---|---|---|---|---|
|  | 283794 | 12754 | 22155 | 161152 | 187246 |
|  | 279572 | 13637 | 18781 | 151478 | 191969 |
|  | 280550 | 15577 | 22508 | 179608 | 178196 |
|  | 329354 | 14958 | 33563 | 198986 | 227023 |
|  | 375098 | 16975 | 39083 | 243881 | 269329 |
|  | 445910 | 19064 | 53255 | 363237 | 277457 |
| Average | 332380 | 15494 | 31558 | 216390 | 221870 |
| Std. Dev. | 52083 | 1711 | 10410 | 58112 | 36066 |

TABLE 5

MCF-7 Human Breast Cancer Cell Plates at Day 5

|  | Untreated cells | Oxyrase ® (20 u/mL) | Oxyrase ® + Substrate | Substrate + Buffer | Buffer |
|---|---|---|---|---|---|
|  | 343503 | 8467 | 6810 | 155311 | 236661 |
|  | 400251 | 10678 | 7896 | 175921 | 283165 |
|  | 393017 | 11018 | 8738 | 183640 | 260937 |
|  | 422401 | 11385 | 8745 | 185254 | 276639 |
|  | 452220 | 11372 | 8448 | 180844 | 264347 |
|  | 438066 | 9439 | 7470 | 214489 | 278824 |
| Average | 408243 | 10393 | 8018 | 182577 | 266762 |
| Std. Dev. | 29319 | 960 | 626 | 11885 | 12781 |

TABLE 6

MCF-7 Human Breast Cancer Cell Plates at Day 7

|  | Untreated cells | Oxyrase ® (20 u/mL) | Oxyrase ® + Substrate | Substrate + Buffer | Buffer |
|---|---|---|---|---|---|
|  | 385969 | 8933 | 6469 | 149128 | 288637 |
|  | 334494 | 10109 | 7624 | 150112 | 269256 |
|  | 335467 | 10013 | 7855 | 139841 | 255179 |
|  | 332549 | 10502 | 8251 | 176875 | 272501 |
|  | 345514 | 10614 | 7733 | 147731 | 276409 |
|  | 385861 | 9162 | 6309 | 163281 | 273191 |
| Average | 353309 | 9889 | 7374 | 154495 | 272529 |
| Std. Dev. | 21737 | 561 | 656 | 10389 | 6884 |

As shown in Tables 2-6 and FIGS. 18-22, Oxyrase® significantly affected the MCF-7 human breast cancer cell count. Particularly, the application of Oxyrase® alone to the cells resulted in a nearly 96% average cell count decrease by Day 3. By Day 7, the average cell count of cells cultured in Oxyrase® alone decreased by over 97%. The application of Oxyrase® and substrate to MCF-7 cells resulted in over a 92% average cell count decrease by Day 3 and over a 98% average cell count decrease by Day 7.

Seventh Set of Experiments

Materials and Methods

In another procedure, cells from A375 (human skin cancer), A549 (human lung cancer), HT-29 (human colon cancer), and U87-MG (human brain cancer) cells lines were thawed and maintained for 2-3 passages in the recommended media and supplements (DMEM medium, F12-K medium, McCoys 5a medium, and 10% FBS). Cells were harvested by trypsinization, counted using a ViCell counter and plated at 20,000 cells per well. Five Perkin Elmer 96 well view plates and five clear Costar 96 well plates of each cell line were made. In a first column of 8 wells, cells alone were plated; in a second column of 8 wells, cells were plated with 10 units/mL Oxyrase®; in a third column of 8 wells, cells were plated with 1 unit/mL Oxyrase®; in a fourth column of 8 wells, cells were plated with 0.1 units/mL Oxyrase®; and in a fifth column of 8 wells, cells were plated in buffer solution. All plates were placed in an incubator at 37 degrees Celsius supplied with 5% carbon dioxide and 10% humidity.

On days 0, 1, 3, 5, and 7, one Perkin Elmer 96 well view plate and one clear Costar 96 well plate were removed from the incubator and a CellTiter Glo® assay performed. Cell-Titer Glo® reagents were thawed at room temperature and mixed just before being added to each plate. Equal volume (max 125 μL) of CellTiter Glo® reagent was added to the plate and the plate incubated in the dark for 15 minutes. Plates were read using a Wallac Victor2 plate reader using the luminescence range Results In the ViCell assay, Oxyrase® showed significant aggregation at the high dosage levels. The aggregates were in the same size range as the cells: 5 to 50 microns. The machine was unable to differentiate between the cells and the aggregates. Thus, the data was inconclusive.

Tables 7-11 below indicate the number of A375 human skin cancer cells on days 0, 1, 3, 5 and 7 as well as the average numbers of cells per treatment as measured by RLU and the standard deviations. These tables are graphically represented in FIGS. 23-27.

TABLE 7

A375 Human Skin Cancer Cell Plates at Day 0

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 405423 | 405191 | 407250 | 403069 | 362061 |
|  | 427726 | 427553 | 419266 | 418648 | 381541 |
|  | 430625 | 441642 | 415574 | 423642 | 386625 |
|  | 441473 | 435380 | 430901 | 432159 | 385014 |
|  | 447931 | 461365 | 433480 | 431691 | 394631 |
|  | 432183 | 449349 | 442154 | 419480 | 379744 |
| Average | 430894 | 436747 | 424771 | 421448 | 381603 |
| Std. Dev. | 9636 | 14039 | 10741 | 7716 | 7154 |

TABLE 8

A375 Human Skin Cancer Cell Plates at Day 1

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 720233 | 61794 | 324305 | 525951 | 494828 |
|  | 719099 | 72031 | 328116 | 530098 | 523479 |
|  | 766724 | 71529 | 329422 | 532739 | 515313 |
|  | 763348 | 71724 | 326970 | 537346 | 495608 |
|  | 726169 | 75497 | 390253 | 545578 | 507303 |
|  | 711955 | 55609 | 301987 | 526494 | 509965 |
| Average | 734588 | 68031 | 333509 | 533034 | 507749 |
| Std. Dev. | 21943 | 6962 | 27039 | 6802 | 10199 |

TABLE 9

A375 Human Skin Cancer Plates at Day 3

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 874924 | 28326 | 328153 | 660068 | 636289 |
|  | 900087 | 33368 | 328728 | 650756 | 722499 |
|  | 886983 | 36846 | 348013 | 681334 | 681229 |
|  | 909443 | 36610 | 346814 | 717719 | 694308 |
|  | 902166 | 33989 | 337559 | 678330 | 687538 |
|  | 923476 | 27331 | 341071 | 684278 | 673993 |
| Average | 899513 | 32745 | 338390 | 678748 | 682643 |
| Std. Dev. | 12373 | 3278 | 6910 | 15696 | 18806 |

TABLE 10

A375 Human Skin Cancer Plates at Day 5

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 638508 | 19462 | 224385 | 613480 | 629741 |
|  | 647789 | 24999 | 264676 | 634924 | 626030 |
|  | 654520 | 26511 | 262534 | 678553 | 653167 |
|  | 648403 | 26287 | 269065 | 696012 | 681236 |
|  | 652956 | 25329 | 261254 | 646947 | 663771 |
|  | 663599 | 19565 | 193045 | 720191 | 675997 |
| Average | 650963 | 23692 | 245827 | 665018 | 654989 |
| Std. Dev. | 6063 | 2786 | 24741 | 33234 | 18677 |

TABLE 11

A375 Human Skin Cancer Plates at Day 7

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 626607 | 16880 | 91548 | 86683 | 729106 |
|  | 645530 | 21193 | 108982 | 932764 | 710301 |
|  | 685544 | 20768 | 101250 | 906665 | 760261 |
|  | 701245 | 22346 | 99663 | 921044 | 769086 |
|  | 667023 | 20722 | 99616 | 903107 | 746968 |
|  | 696407 | 17454 | 109467 | 922956 | 740487 |
| Average | 670393 | 19894 | 101754 | 908787 | 742702 |
| Std. Dev. | 24006 | 1818 | 4980 | 16802 | 16070 |

As shown in Tables 7-11 and FIGS. 23-27, Oxyrase® significantly affected the A375 human skin cancer cell count and in a dose-dependent manner. Particularly, the application of Oxyrase® at 10 u/mL to the cells resulted in a nearly 93% average cell count decrease by Day 3. By Day 7, the average cell count of cells cultured in Oxyrase® at 10 u/mL decreased by over 95%. The application of Oxyrase® at 1 u/mL to the cells resulted in over a 20% average cell count decrease by Day 3. By Day 7, the average cell count of cells cultured in Oxyrase® at 1 u/mL decreased by over 76%. The application of Oxyrase® at 0.1 u/mL resulted in tumor cell proliferation rather than necrosis.

Tables 12-16 below indicate the number of A549 human lung cancer cells on days 0, 1, 3, 5 and 7 as well as the average numbers of cells per treatment as measured by RLU and the standard deviations. These tables are graphically represented in FIGS. 28-32.

TABLE 12

A549 Human Lung Cancer Cell Plates at Day 0

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 345246 | 358472 | 363330 | 350990 | 343454 |
|  | 375448 | 403919 | 400146 | 373731 | 362483 |
|  | 351270 | 361959 | 370757 | 370832 | 361872 |
|  | 375559 | 399111 | 409948 | 394477 | 372549 |
|  | 350460 | 349194 | 377131 | 364667 | 370767 |
|  | 370618 | 393013 | 400482 | 379453 | 386696 |
| Average | 361434 | 377611 | 386966 | 372358 | 366304 |
| Std. Dev. | 12442 | 21070 | 16560 | 10195 | 10367 |

TABLE 13

A549 Human Lung Cancer Cell Plates at Day 1

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 477014 | 47237 | 304736 | 481029 | 353640 |
|  | 481232 | 52176 | 314952 | 483366 | 368979 |
|  | 478244 | 53471 | 312027 | 498753 | 379231 |
|  | 503275 | 56188 | 333275 | 511148 | 373584 |
|  | 480294 | 51186 | 312681 | 489597 | 394970 |
|  | 439986 | 40397 | 286435 | 484055 | 377755 |
| Average | 476674 | 50109 | 310685 | 491325 | 374693 |
| Std. Dev. | 18664 | 5103 | 13892 | 10593 | 12371 |

TABLE 14

A549 Human Lung Cancer Cell Plates at Day 3

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 651356 | 65500 | 310035 | 614460 | 495556 |
|  | 669875 | 57693 | 326189 | 638792 | 520736 |
|  | 670717 | 60301 | 338215 | 657829 | 549656 |
|  | 659886 | 41331 | 340267 | 647173 | 552521 |
|  | 671078 | 44570 | 323350 | 653303 | 529358 |
|  | 695468 | 36440 | 324719 | 634417 | 518080 |
| Average | 669730 | 50973 | 327129 | 640996 | 527651 |
| Std. Dev. | 9406 | 10192 | 8075 | 11773 | 16194 |

TABLE 15

A549 Human Lung Cancer Cell Plates at Day 5

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 484307 | 25266 | 298234 | 487008 | 402255 |
|  | 541222 | 31563 | 321590 | 498903 | 422726 |
|  | 510920 | 28295 | 306760 | 511846 | 435670 |
|  | 519042 | 26261 | 294355 | 510875 | 439223 |
|  | 519290 | 25629 | 294345 | 513735 | 413259 |
|  | 492427 | 23703 | 288176 | 484070 | 412025 |
| Average | 511201 | 26786 | 300577 | 501073 | 420860 |
| Std. Dev. | 15317 | 2095 | 9066 | 11079 | 11680 |

TABLE 16

A549 Human Lung Cancer Cell Plates at Day 7

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 579781 | 22252 | 347759 | 542283 | 402304 |
|  | 554002 | 27192 | 330231 | 528484 | 423048 |
|  | 571656 | 28280 | 319346 | 562994 | 418685 |
|  | 578365 | 28100 | 318500 | 542120 | 436897 |
|  | 579691 | 26867 | 321905 | 555766 | 432012 |
|  | 576857 | 21389 | 371600 | 553285 | 445579 |
| Average | 573392 | 25680 | 334890 | 547489 | 426421 |
| Std. Dev. | 7042 | 2573 | 16526 | 9860 | 11742 |

As shown in Tables 12-16 and FIGS. 28-32, Oxyrase® significantly affected the A549 human lung cancer cell count and in a dose-dependent manner. Particularly, the application of Oxyrase® at 10 u/mL to the cells resulted in over a 86% average cell count decrease by Day 3. By Day 7, the average cell count of cells cultured in Oxyrase® at 10 u/mL decreased by nearly 93%. The application of Oxyrase® at 1 u/mL to the cells resulted in over a 15% average cell count decrease by Day 3. By Day 7, the average cell count of cells cultured in Oxyrase® at 1 u/mL increased slightly, bringing the total average cell count decrease to over 13%. Again, the application of Oxyrase® at 0.1 u/mL resulted in tumor cell proliferation rather than necrosis.

Tables 17-21 below indicate the number of HT29 human colon cancer cells on days 0, 1, 3, 5 and 7 as well as the average numbers of cells per treatment as measured by RLU and the standard deviations. These tables are graphically represented in FIGS. 33-37.

TABLE 17

HT29 Human Colon Cancer Cell Plates at Day 0

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 332661 | 324181 | 310997 | 322381 | 307747 |
|  | 324424 | 320667 | 338423 | 324482 | 319226 |
|  | 303697 | 320464 | 338592 | 341301 | 319891 |
|  | 330835 | 331417 | 343504 | 350461 | 336622 |
|  | 323711 | 332198 | 317412 | 326622 | 331581 |
|  | 336573 | 354975 | 343977 | 334350 | 345278 |
| Average | 325317 | 330650 | 332151 | 333266 | 326724 |
| Std. Dev. | 8040 | 8880 | 11964 | 8771 | 11103 |

TABLE 18

HT29 Human Colon Cancer Cell Plates at Day 1

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 544467 | 70272 | 399596 | 453158 | 368826 |
|  | 537757 | 74877 | 411284 | 498678 | 358358 |
|  | 550553 | 82126 | 431625 | 477177 | 393214 |
|  | 544536 | 76798 | 390210 | 484061 | 379530 |
|  | 558428 | 76015 | 409267 | 469781 | 370672 |
|  | 543219 | 70229 | 381204 | 464625 | 375197 |
| Average | 546493 | 75053 | 403864 | 474580 | 374300 |
| Std. Dev. | 6505 | 4086 | 16192 | 14482 | 10671 |

TABLE 19

HT29 Human Colon Cancer Cell Plates at Day 3

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 743510 | 29729 | 414708 | 572576 | 688071 |
|  | 804750 | 36179 | 435458 | 579522 | 755442 |
|  | 798261 | 37877 | 400284 | 588757 | 704079 |
|  | 786509 | 36126 | 424163 | 591265 | 745260 |
|  | 803066 | 33081 | 427483 | 608671 | 735911 |
|  | 781647 | 27802 | 398647 | 581003 | 689514 |
| Average | 786291 | 33466 | 416791 | 586966 | 719713 |
| Std. Dev. | 15808 | 3262 | 12244 | 9265 | 25825 |

TABLE 20

HT29 Human Colon Cancer Cell Plates at Day 5

|  | Untreated cells | Cells + Oxyrase ® (10 u/mL) | Cells + Oxyrase ® (1 u/mL) | Cells + Substrate (0.1 u/mL) | Cells + Buffer |
| --- | --- | --- | --- | --- | --- |
|  | 773921 | 27458 | 352806 | 637560 | 700656 |
|  | 813701 | 34695 | 362090 | 638497 | 749027 |
|  | 821531 | 33493 | 401780 | 613611 | 766700 |
|  | 788522 | 33233 | 391520 | 678266 | 792948 |
|  | 795592 | 31746 | 366867 | 675839 | 792771 |
|  | 776468 | 27728 | 365518 | 636588 | 742762 |
| Average | 794956 | 31392 | 373430 | 646727 | 757477 |
| Std. Dev. | 15319 | 2533 | 15480 | 20217 | 26662 |

TABLE 21

HT29 Human Colon Cancer Cell Plates at Day 7

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 870323 | 28379 | 320388 | 642555 | 892081 |
|  | 895223 | 33410 | 407474 | 693414 | 955803 |
|  | 880451 | 35551 | 332076 | 715742 | 879193 |
|  | 907650 | 36197 | 342424 | 691590 | 925313 |
|  | 877044 | 33524 | 360478 | 725073 | 917412 |
|  | 912956 | 27801 | 366309 | 719605 | 903942 |
| Average | 890608 | 32477 | 354858 | 697997 | 912291 |
| Std. Dev. | 14669 | 2925 | 23229 | 22144 | 20552 |

As shown in Tables 17-21 and FIGS. 33-37, Oxyrase® significantly affected the HT29 human colon cancer cell count and in a dose-dependent manner. Particularly, the application of Oxyrase® at 10 u/mL to the cells resulted in over a 89% average cell count decrease by Day 3. By Day 7, the average cell count of cells cultured in Oxyrase® at 10 u/mL decreased by over 90%. The application of Oxyrase® at 1 u/mL to the cells resulted in an initial 25% average cell count increase by Day 3. By Day 7, the average cell count of cells cultured in Oxyrase® at 1 u/mL decreased, bringing the total average cell count increase to approximately 7%. Again, the application of Oxyrase® at 0.1 u/mL resulted in tumor cell proliferation rather than necrosis.

Tables 22-26 below indicate the number of U87-MG human brain cancer cells on days 0, 1, 3, 5 and 7 as well as the average numbers of cells per treatment as measured by RLU and the standard deviations. These tables are graphically represented in FIGS. 38-42.

TABLE 22

U87-MG Human Brain Cancer Cell Plates at Day 0

|  | Untreated cells | Untreated cells | Untreated cells | Untreated cells | Untreated cells |
|---|---|---|---|---|---|
|  | 337102 | 336389 | 334581 | 311104 | 331938 |
|  | 343741 | 350414 | 354552 | 317121 | 333831 |
|  | 351995 | 358680 | 355650 | 328613 | 334815 |
|  | 343369 | 344721 | 345962 | 320379 | 335596 |
|  | 341743 | 349024 | 338846 | 304674 | 336220 |
|  | 342915 | 347917 | 349362 | 335841 | 344379 |
| Average | 343478 | 347858 | 346492 | 319622 | 336130 |
| Std. Dev. | 2927 | 4868 | 6696 | 8656 | 2780 |

TABLE 23

U87-MG Human Brain Cancer Cell Plates at Day 1

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 434854 | 137817 | 332715 | 412877 | 291163 |
|  | 436787 | 143365 | 323369 | 438584 | 304777 |
|  | 405376 | 147376 | 313337 | 421517 | 301596 |
|  | 442558 | 130431 | 308229 | 408566 | 311351 |
|  | 414274 | 131437 | 304093 | 413240 | 296354 |
|  | 430870 | 123340 | 309807 | 417697 | 295889 |
| Average | 427453 | 135628 | 315258 | 418747 | 300188 |
| Std. Dev. | 13183 | 8147 | 9815 | 9753 | 6612 |

TABLE 24

U87-MG Human Brain Cancer Cell Plates at Day 3

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 556814 | 21116 | 255467 | 614971 | 428848 |
|  | 566815 | 25455 | 247791 | 622082 | 441827 |
|  | 555042 | 26285 | 251568 | 629786 | 439023 |
|  | 564140 | 27025 | 274447 | 636148 | 427078 |
|  | 567164 | 26382 | 290587 | 653493 | 431461 |
|  | 566195 | 18843 | 244041 | 645316 | 447034 |
| Average | 562695 | 24184 | 260650 | 633633 | 435879 |
| Std. Dev. | 4511 | 2803 | 14578 | 11353 | 6750 |

TABLE 25

U87-MG Human Brain Cancer Cell Plates at Day 5

|  | Untreated cells | Cells + Oxyrase ® | Cells + Oxyrase ® (1 u/mL) | Cells + Substrate (0.1 u/mL) | Cells + Buffer |
|---|---|---|---|---|---|
|  | 404194 | 14519 | 245481 | 340176 | 314664 |
|  | 415082 | 18408 | 241115 | 365306 | 326332 |
|  | 402496 | 17543 | 245552 | 348806 | 325702 |
|  | 393627 | 17560 | 215042 | 345409 | 321334 |
|  | 397846 | 17153 | 206823 | 363456 | 326876 |
|  | 438402 | 13798 | 220354 | 386903 | 332592 |
| Average | 408608 | 16497 | 229061 | 358343 | 324583 |
| Std. Dev. | 12089 | 1559 | 14988 | 13546 | 4390 |

TABLE 26

U87-MG Human Brain Cancer Cell Plates at Day 7

|  | Untreated cells | Cells + Oxyrase ® (10 u/mL) | Cells + Oxyrase ® (1 u/mL) | Cells + Substrate (0.1 u/mL) | Cells + Buffer |
|---|---|---|---|---|---|
|  | 392960 | 12695 | 128503 | 297512 | 375710 |
|  | 399727 | 14211 | 146874 | 311584 | 386271 |
|  | 390194 | 15849 | 144389 | 308812 | 375510 |
|  | 404836 | 15187 | 155503 | 300217 | 370549 |
|  | 394703 | 14508 | 141575 | 307096 | 372329 |
|  | 381641 | 12012 | 141287 | 310289 | 365932 |
| Average | 394010 | 14077 | 143022 | 305918 | 374384 |
| Std. Dev. | 5745 | 1149 | 5900 | 4703 | 4780 |

As shown in Tables 22-26 and FIGS. 38-42, Oxyrase® significantly affected the U87-MG human brain cancer cell count and in a dose-dependent manner. Particularly, the application of Oxyrase® at 10 u/mL to the cells resulted in an approximate 93% average cell count decrease by Day 3. By Day 7, the average cell count of cells cultured in Oxyrase® at 10 u/mL decreased by about 96%. The application of Oxyrase® at 1 u/mL to the cells resulted in an initial approximate 25% average cell count decrease by Day 3. By Day 7, the average cell count of cells cultured in Oxyrase® at 1 u/mL decreased further, bringing the total average cell count decrease to approximately 59% from the initial average cell count. The application of Oxyrase® at 0.1 u/mL resulted in an initial tumor cell proliferation followed by cell necrosis for a 4% decrease in total average number of cells.

Eighth Set of Experiments

An additional set of experiments was conducted to compare the actions of (a) anaerobe infection alone with (b) anaerobe infection with Oxyrase® and substrate on tumor growth.

Materials and Methods

Eighteen (18) female BALB/C mice were purchased from Charles River Laboratories at four (4) weeks old. In addition, eighteen C57BL/6 mice were purchased from Charles River Laboratories at four (4) weeks old. The animals were fed ad libitum Teklad Certified Global 18% Protein Rodent diet (2018C). The mice were housed in plastic shoebox cages with bedding and kept in a 12-hour light cycle at 20-26 degrees Celsius (68-78.8 degrees Fahrenheit) and 30-70% humidity.

4T1 murine breast cancer cells and Lewis lung carcinoma (LLC) cancer cell lines were obtained from American Type Culture Collection (ATCC, Manassas, Va.). 4T1 is an animal model for stage IV human breast cancer. The LLC cells were cultured in ATCC-formulated Dulbecco's Modified Eagle's Medium, containing 10% fetal bovine serum (FBS) and 1% of 100× Penicillin-streptomycin glutamine, while the 4T1 cells were cultured in RPMI-1649 medium containing 10% FBS and 1% of 100× Penicillin-streptomycin glutamine. Cells were cultured in a humidified incubator at 37 degrees Celsius in an appropriate atmosphere of 5% $CO_2$ and 95% air.

Tumor cells in passage four were used for the implantation and were harvested during log phase growth. BALB/c mice were inoculated with $1\times10^6$ 4 T1 cells on their right flanks. C57/CL mice were inoculated with $1\times10^6$ LLC cells on their right flanks. Tumor measurements were initiated as soon as the tumors were palpable. Thereafter, tumors were measured twice weekly. Tumors were measured in two dimensions using calipers and volume was calculated using the formula:

$$\text{Tumor volume (mm}^3) = \frac{width^2 \times \text{length}}{2}$$

where width and length are dimensions of a tumor in mm. Tumor weight may be estimated with the assumption 1 mg is equivalent to 1 $mm^3$ or tumor volume.

Animals were randomized using the stratified random sampling algorithm when tumors reached a size range of 74.9-279.5 $mm^3$ for the 4T1 model or 107.5-257.4 $mm^3$ for the LLC model. Treatments or control vehicle (PBS) were administered on Day 1 following randomization.

The following concentrations were provided by the sponsor:

*C. perfringens*

*C. perfringens* was cultured for 18-24 hours with about $7\times10^8$ cfu/mL to be used at 1:100 dilution. With respect to the substrate, 4 M sodium L-lactate was used at 1:100 dilution (final concentration 40 mM). 110 u/ml Oxyrase® was used at a final concentration of 20 u/mL.

*B. adolescentis*

BHI-OB was cultured for 18-24 hours with about $7\times10^8$ cfu/mL to be used at 1:100 dilution. With respect to the substrate, 4 M sodium L-lactate was used at 1:100 dilution (final concentration 40 mM). 110 u/ml Oxyrase® was used at a final concentration of 20 u/mL.

In order to achieve the correct concentrations, materials were prepared as follows:

Schaedler-Blood Agar Oxyplates were removed from the refrigerator and allowed to reach room temperature. The oxyplates, with the lids removed, were then placed in a Class II biological safety cabinet (BSC) to eliminate condensation. PBS, substrate, and Oxyrase® were placed in the Class II BSC. *B. adolescentis* and *C. perfringens* were removed from the incubator and placed in the Class II BSC.

With respect to treatment Group 1, 9 mL control PBS was slowly loaded by pipette into a dosing vial and cap with crimper.

Regarding treatment Group 2 (*C. perfringens* alone), 8.71 mL PBS was slowly loaded by pipette into a dosing vial. Next, 0.390 mL *C. perfringens* was slowly loaded by pipette into the dosing vial to yield 1.5 μL *C. perfringens* and 33.5 μL PBS per injection. The dosing vial was gently rolled to mix, avoiding vigorous mixing to prevent aeration. Following mixing, the dosing vial was capped with a crimper.

Regarding treatment Group 3 (Oxyrase®+substrate+*C. perfringens*), 18.0 mL Oxyrase® was slowly loaded by pipette into a dosing vial. Next, 0.150 mL *C. perfringens* and 0.150 mL substrate were slowly loaded by pipette into the dosing vial to yield 1.5 μL *C. perfringens,* 1.5 μL substrate and 180 μL Oxyrase® per injection. The dosing vial was gently rolled to mix, avoiding vigorous mixing to prevent aeration. Following mixing, the dosing vial was capped with a crimper.

Regarding treatment Group 4 (*B. adolescentis* alone), 8.71 mL PBS was slowly loaded by pipette into a dosing vial. Next, 0.390 mL *B. adolescentis* was slowly loaded by pipette into the dosing vial to yield 1.5 μL *B. adolescentis* and 33.5 μL PBS per injection. The dosing vial was gently rolled to mix, avoiding vigorous mixing to prevent aeration. Following mixing, the dosing vial was capped with a crimper.

Regarding treatment Group 5 (Oxyrase®+substrate+*B. adolescentis*), 18.0 mL Oxyrase® was slowly loaded by pipette into a dosing vial. Next, 0.150 mL *B. adolescentis* and 0.150 mL substrate were slowly loaded by pipette into the dosing vial to yield 1.5 μL *B. adolescentis,* 1.5 μL substrate and 180 μL Oxyrase® per injection. The dosing vial was gently rolled to mix, avoiding vigorous mixing to prevent aeration. Following mixing, the dosing vial was capped with a crimper.

Doses to mice were administered within 30 minutes of receiving the test article from the microbiology laboratories using 27 G needles and Hamilton syringes according to the treatment and dosage schedule in Table 27 below.

TABLE 27

Groups and dosing schedule for 4T1 and LLC syngeneic mouse models

| Tumor Model | Group (n = 3) | Treatment |
|---|---|---|
| 4T1 | 1 | PBS (control) |
| | 2 | *C. perfringens* |
| | 3 | Oxyrase ® + substrate + *C. perfringens* |
| | 4 | *B. adolescentis* |
| | 5 | Oxyrase ® + substrate + *B. adolescentis* |
| LLC | 1 | PBS (control) |
| | 2 | *C. perfringens* |
| | 3 | Oxyrase ® + substrate + *C. perfringens* |
| | 4 | *B. adolescentis* |
| | 5 | Oxyrase ® + substrate + *B. adolescentis* |

On the day of treatment, each animal received one intratumor injection of anaerobe (*Clostridium perfringens* or *Bifidobacterium adolescentis*) alone or in combination with Oxyrase® and substrate as described in Table 27 above. Termination of the study or animals occurred at Day 29 post-inoculation or when tumor sizes exceeded 1,000 $mm^3$.

Study Log Study Director Animal Study Management Software (San Francisco, Calif.) was used to randomize animals. Data collection included body weights, tumor measurements, and daily clinical observations (e.g., morbidity, mortality, feeding, grooming). All data was analyzed using GraphPad InStat3 (GraphPad Software, Inc., La Jolla, Calif.). Treatment groups were compared with vehicle control groups using one-way ANOVA statistical analysis. If a significant difference (p<0.05) was observed, the Tukey-Kramer multiple comparison test was conducted.

Results

All results for tumor volume are reported in cubic millimeters ($mm^3$). All results for body weight are reported in grams (g).

Mouse 4T1 Breast Tumor Model

Animals were randomized on day 8 post-inoculation with a mean (±standard deviation) tumor size of: 136.61±43.35, 118.15±64.56, 174.55±108.43, 256.40±41.75, and 196.60±62.83 for Groups 1, 2, 3, 4 and 5 respectively. Mean body weights (±SD) at randomization were: 17.13±0.35, 16.77±0.51, 17.20±0.30, 17.20±0.10, and 17.07±0.15 for Groups 1, 2, 3, 4 and 5 respectively. Table 28 below summarizes the mean body weights (±SD) for the entire study. At termination day (Day 19), the mean tumor size (±SD) for the control group was 1872.22±1399.88 compared to 1508.71±1204.68, 1697.77±53.17, and 2359.78±418.19 for Groups 2, 3, and 4 respectively. Animals in Group 5 had to be terminated early (Day 8) due to tumor sizes exceeding humane limits. At termination, the mean body weight (±SD) for Group 5 was 1151±237.28.

TABLE 28

4T1 Murine Breast Cancer Model Mean Body Weights (±SD)

| | Day 1 | Day 4 | Day 6 | Day 8 | Day 13 | Day 15 | Day 19 |
|---|---|---|---|---|---|---|---|
| Group 1 | | | | | | | |
| 1 | 17.1 | 17.3 | 17.9 | 18.3 | 19.7 | 20.1 | 21.0 |
| 2 | 16.8 | 17.8 | 18.0 | 18.0 | 19.2 | 19.3 | 19.9 |
| 3 | 17.5 | 18.0 | 18.7 | 18.3 | 19.3 | 19.5 | 20.1 |
| Avg. | 17.13 | 17.70 | 18.20 | 18.20 | 19.40 | 19.63 | 20.33 |
| SD | 0.35 | 0.36 | 0.44 | 0.17 | 0.26 | 0.42 | 0.59 |
| Group 2 | | | | | | | |
| 4 | 16.2 | 16.7 | 17.4 | 17.7 | 19.0 | 19.9 | 19.8 |
| 5 | 17.2 | 17.6 | 18.6 | 19.0 | 20.0 | 19.9 | 21.1 |
| 6 | 16.9 | 17.3 | 18.5 | 18.3 | 19.2 | 18.9 | 19.5 |
| Avg. | 16.77 | 17.20 | 18.17 | 18.33 | 19.40 | 19.57 | 20.13 |
| SD | 0.51 | 0.46 | 0.67 | 0.65 | 0.53 | 0.58 | 0.85 |
| Group 3 | | | | | | | |
| 7 | 17.2 | | | | | | |
| 8 | 17.5 | 15.8 | 16.6 | 17.2 | 19.7 | 19.8 | 20.6 |
| 9 | 16.9 | 16.9 | 17.8 | 19.0 | 20.8 | 21.3 | 22. |
| Avg. | 17.20 | 16.35 | 17.20 | 18.10 | 20.25 | 20.55 | 21.30 |
| SD | 0.30 | 0.78 | 0.85 | 1.27 | 0.78 | 1.06 | 0.99 |
| Group 4 | | | | | | | |
| 10 | 17.2 | 17.7 | 19.2 | 19.4 | 20.2 | 20.4 | 20.5 |
| 11 | 17.1 | 16.8 | 17.5 | 18.0 | 19.3 | 19.6 | 20.0 |
| 12 | 17.3 | 16.5 | 17.9 | 18.1 | 14.4 | 19.4 | 20.0 |
| Avg. | 17.20 | 17.00 | 18.20 | 18.50 | 17.97 | 19.80 | 20.17 |
| SD | 0.10 | 0.62 | 0.89 | 0.78 | 3.12 | 0.53 | 0.29 |
| Group 5 | | | | | | | |
| 13 | 17.1 | 16.9 | 16.9 | 17.5 | Terminated | | |
| 14 | 17.2 | 15.3 | 16.0 | 16.3 | Terminated | | |
| 15 | 16.9 | 16.5 | 17.2 | 17.2 | Terminated | | |
| Avg. | 17.07 | 16.23 | 16.70 | 17.00 | Terminated | | |
| SD | 0.15 | 0.83 | 0.62 | 0.62 | Terminated | | |

Table 29 below summarizes the tumor volumes (±SD) for the entire study. Mean body weights (±SD) at termination were: 21.33±0.59, 20.13±0.85, 21.3±0.99, and 20.17±0.29 for Groups 1, 2, 3, and 4, respectively.

TABLE 29

4T1 Murine Breast Cancer Model Tumor Volumes (±SD)

| | Pre-Study (pre-inoculation) | Day 1 | Day 4 | Day 6 | Day 8 | Day 12 | Day 19 |
|---|---|---|---|---|---|---|---|
| Group 1 | | | | | | | |
| 1 | 36.95 | 98.56 | 280.87 | 371.77 | 644.14 | 1197.84 | 2001.85 |
| 2 | 67.19 | 127.48 | 222.00 | 117.39 | 174.76 | 250.79 | 412.04 |
| 3 | 83.70 | 183.80 | 347.34 | 351.15 | 670.72 | 735.64 | 3202.78 |
| Avg. | 62.61 | 136.61 | 283.40 | 280.10 | 496.54 | 728.09 | 1872.22 |
| SD | 23.71 | 43.35 | 62.71 | 141.29 | 278.99 | 473.57 | 1399.88 |
| Median | 67.2 | 127.5 | 280.9 | 351.2 | 644.14 | 735.64 | 2001.90 |
| Group 2 | | | | | | | |
| 4 | 39.54 | 77.84 | 192.69 | 273.62 | 291.52 | 476.58 | 819.64 |
| 5 | 77.80 | 192.61 | 548.02 | 647.38 | 784.46 | 1089.71 | 2899.73 |
| 6 | 22.12 | 84.01 | 130.09 | 202.55 | 224.49 | 369.66 | 809.61 |
| Avg. | 46.49 | 118.15 | 290.26 | 374.52 | 433.49 | 645.32 | 1509.66 |
| SD | 28.48 | 64.56 | 225.40 | 238.97 | 305.79 | 388.55 | 1203.85 |
| Median | 39.50 | 84.00 | 192.70 | 273.60 | 291.52 | 476.58 | 819.64 |
| Group 3 | | | | | | | |
| 7 | 45.96 | 75.89 | | | Deceased | | |
| 8 | 72.00 | 157.11 | 230.30 | 528.96 | 760.64 | 977.88 | 1389.08 |
| 9 | 49.40 | 290.64 | 359.85 | 574.99 | 419.90 | 1203.13 | 1735.37 |
| Avg. | 55.79 | 174.55 | 295.08 | 551.97 | 590.27 | 1090.51 | 1562.23 |
| SD | 14.15 | 108.43 | 91.60 | 32.55 | 240.94 | 159.28 | 244.86 |
| Median | 49.40 | 157.10 | 295.10 | 552.00 | 590.27 | 1090.50 | 1562.20 |

TABLE 29-continued

4T1 Murine Breast Cancer Model Tumor Volumes (±SD)

| | Pre-Study (pre-inoculation) | Day 1 | Day 4 | Day 6 | Day 8 | Day 12 | Day 19 |
|---|---|---|---|---|---|---|---|
| Group 4 | | | | | | | |
| 10 | 96.07 | 287.16 | 530.59 | 759.75 | 891.67 | 1439.44 | 2020.06 |
| 11 | 68.42 | 273.16 | 283.02 | 521.83 | 658.01 | 1170.05 | 2232.43 |
| 12 | 33.14 | 208.88 | 393.25 | 542.97 | 844.95 | 1081.01 | 2826.84 |
| Avg. | 65.88 | 256.40 | 402.29 | 608.18 | 798.21 | 1230.17 | 2359.78 |
| SD | 31.55 | 41.75 | 124.03 | 131.69 | 123.64 | 186.62 | 418.19 |
| Median | 68.40 | 273.20 | 393.30 | 543.00 | 844.95 | 1170.10 | 2232.40 |
| Group 5 | | | | | | | |
| 13 | 72.54 | 169.52 | 690.74 | 1015.37 | 1424.33 | Terminated | |
| 14 | 60.81 | 151.84 | 226.32 | 317.71 | 995.59 | Terminated | |
| 15 | 150.08 | 268.43 | 564.31 | 773.85 | 1033.76 | Terminated | |
| Avg. | 94.48 | 196.60 | 493.79 | 702.31 | 1151.23 | Terminated | |
| SD | 48.51 | 62.83 | 240.10 | 354.29 | 237.28 | Terminated | |
| Median | 72.50 | 169.50 | 564.30 | 773.90 | 1033.80 | Terminated | |

Figure 43:
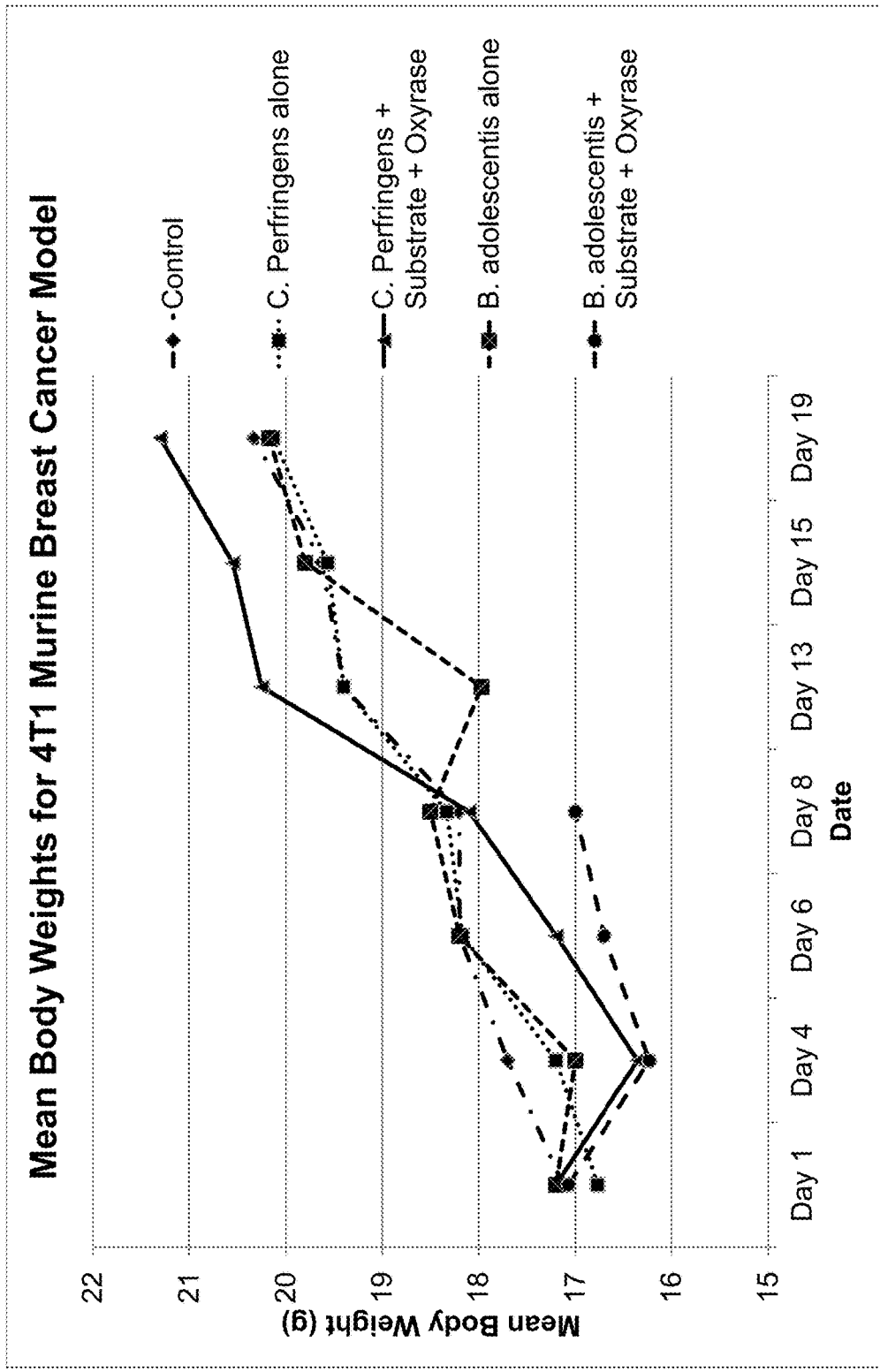
FIG. 43 is a graphical representation of the average body weights in grams±standard deviation of mice inoculated with the 4T1 murine breast cancer cell line and treated with one of the following four compositions: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.
Figure 44:
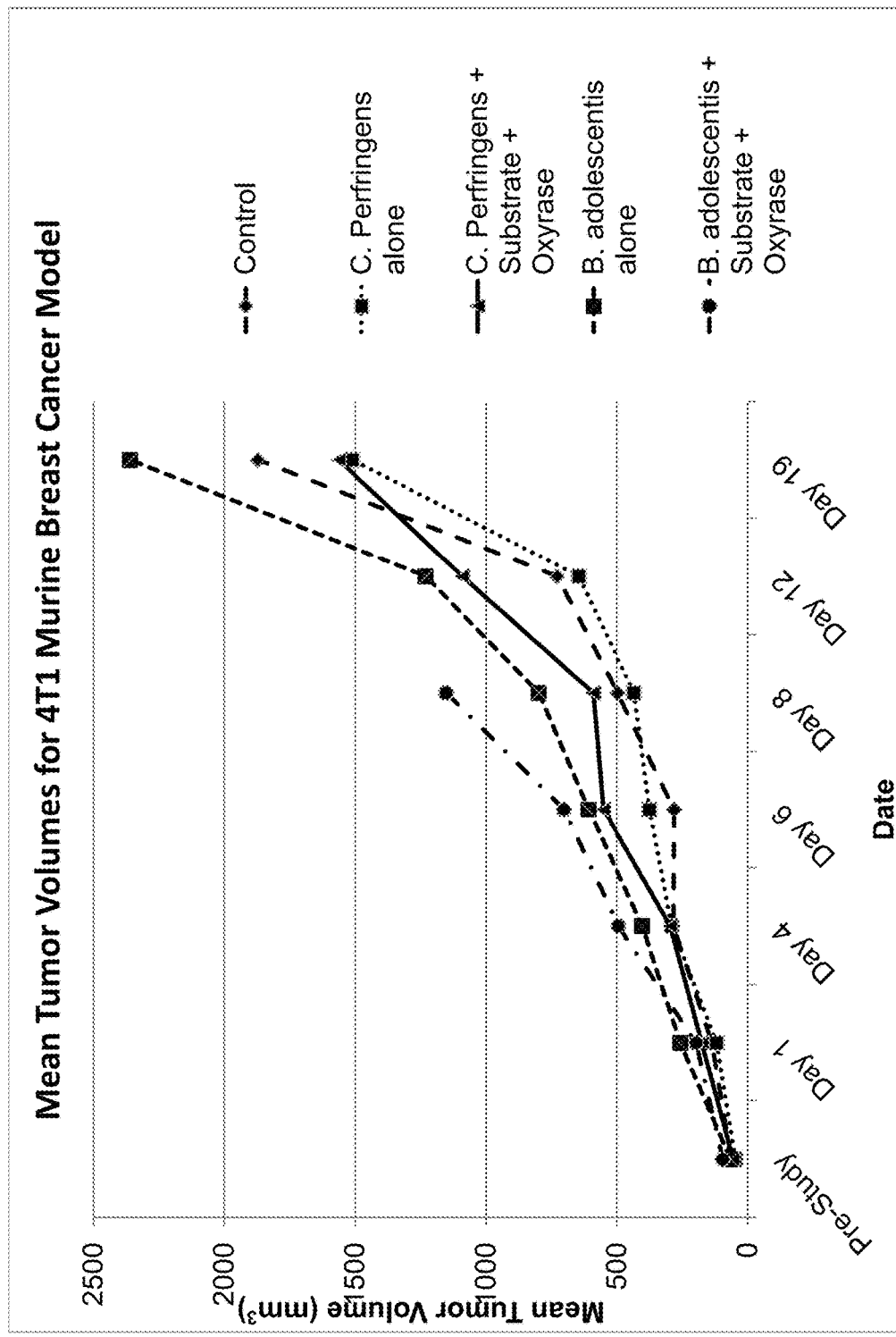
FIG. 44 is a graphical representation of the average tumor volume in $mm^3$±standard deviation of mice inoculated with the 4T1 murine breast cancer cell line and treated with one of the following: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.
Figure 45:
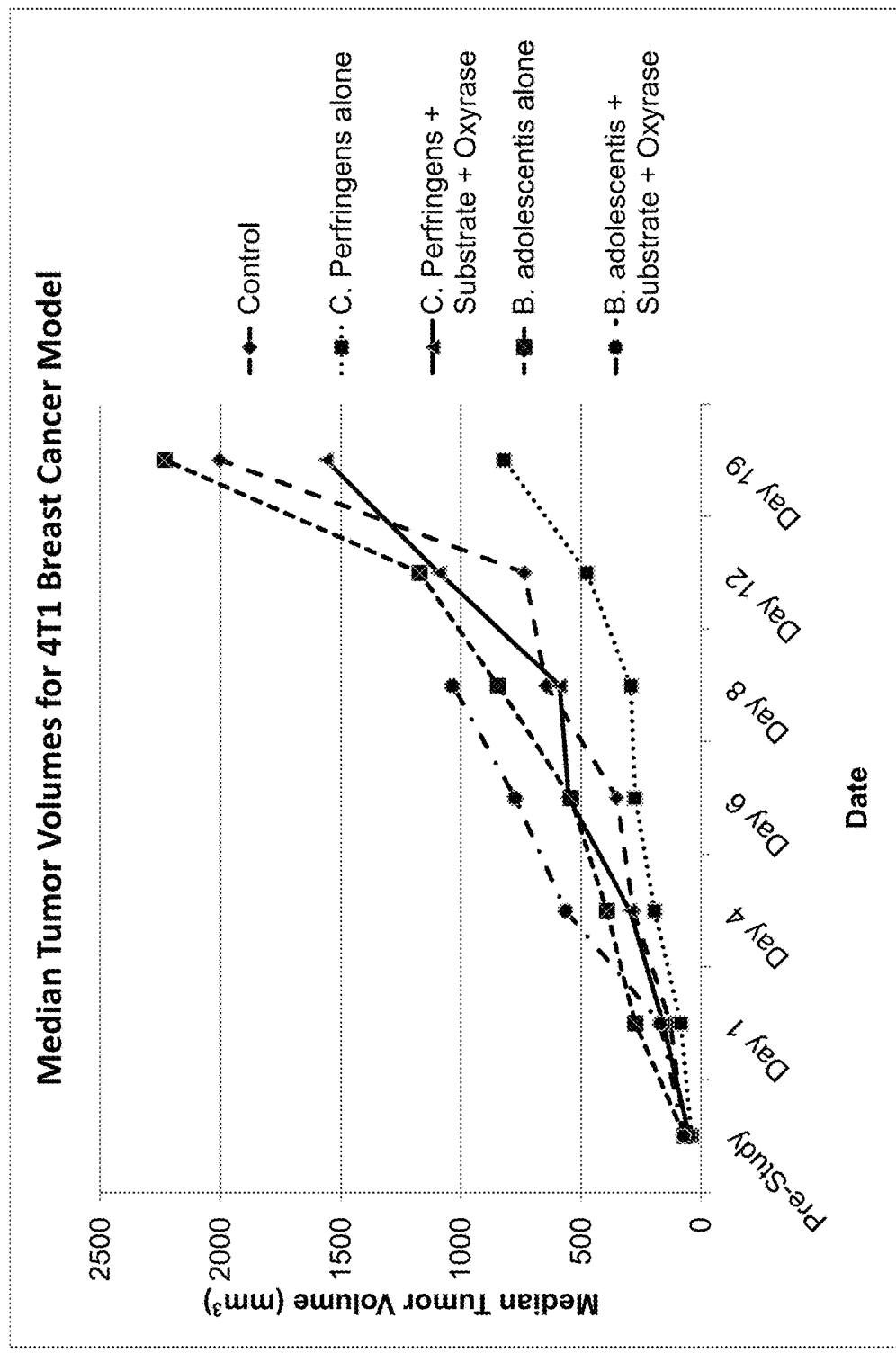
FIG. 45 is a graphical representation of the median tumor volume in $mm^3$±standard deviation of mice inoculated with the 4T1 murine breast cancer cell line and treated with one of the following: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.

FIG. 43 is a graphical illustration of the average body weights during the study period. On Day 2 post-treatment, there was a treatment-associated mortality in Group 3 (animal 7). All surviving animals in Group 3 and animals in Group 5 showed clinical signs including rough coats and hypoactivity following test article administration. FIG. 44 is a graphical illustration of mean tumor volume, while FIG. 45 is a graphical illustration of median tumor volume.

Mouse LLC Lung Cancer Model

Animals were randomized on day 8 post-inoculation with a mean (±SD) tumor size of: 169.29±40.07, 197.36±79.03, 206.56±47.49, 187.30±24.70, and 172.39±18.72 for Groups 1, 2, 3, 4, and 5 respectively. Mean body weights (±SD) at randomization were 17.23±0.23, 17.30±0.26, 17.47±0.06, 17.43±0.42, and 17.30±0.26 for Groups 1, 2, 3, 4, and 5 respectively. Table 30 below summarizes the mean body weights (±SD) for the entire study. At day of termination (Day 11), the mean tumor size (±SD) for the control group was 1243.07±314.28 compared to 1593.0±305.42, 206.56±47.49, 1280.46±215.15, and 1285.76±291.85 for Groups 2, 3, 4, and 5 respectively.

TABLE 30

LLC Murine Lung Cancer Model Mean Body Weights (±SD)

| | Day 1 | Day 4 | Day 6 | Day 8 |
|---|---|---|---|---|
| Group 1 | | | | |
| 1 | 17.1 | 17.4 | 18.8 | 18.6 |
| 2 | 17.1 | 18.0 | 18.2 | 17.3 |
| 3 | 17.5 | 19.4 | 20.4 | 20.0 |
| Avg. | 17.23 | 18.27 | 19.13 | 18.63 |
| SD | 0.23 | 1.03 | 1.14 | 1.35 |
| Group 2 | | | | |
| 4 | 17.2 | 17.9 | 18.9 | 19.2 |
| 5 | 17.6 | 19.7 | 20.5 | 21.0 |
| 6 | 17.1 | 17.3 | 18.2 | 16.6 |
| Avg. | 17.30 | 18.30 | 19.20 | 18.93 |
| SD | 0.26 | 1.25 | 1.18 | 2.21 |
| Group 3 | | | | |
| 7 | 17.5 | | Terminated | |
| 8 | 17.4 | | Terminated | |
| 9 | 17.5 | 13.2 | Terminated | |
| Avg. | 17.47 | 13.2 | Terminated | |
| SD | 0.06 | 0 | Terminated | |

TABLE 30-continued

LLC Murine Lung Cancer Model Mean Body Weights (±SD)

| | Day 1 | Day 4 | Day 6 | Day 8 |
|---|---|---|---|---|
| Group 4 | | | | |
| 10 | 17.9 | 18.6 | 18.8 | 19.6 |
| 11 | 17.1 | 17.6 | 18.4 | 19.0 |
| 12 | 17.3 | 18.0 | 17.6 | 16.5 |
| Avg. | 17.43 | 18.07 | 18.27 | 18.37 |
| SD | 0.42 | 0.50 | 0.61 | 1.64 |
| Group 5 | | | | |
| 13 | 17.9 | 17.2 | 19.2 | 17.9 |
| 14 | 17.8 | 17.0 | 19.5 | 17.8 |
| 15 | 19.0 | 18.4 | 20.5 | 19.0 |
| Avg. | 18.23 | 17.53 | 19.73 | 18.23 |
| SD | 0.67 | 0.76 | 0.68 | 0.67 |

Table 31 below summarizes the tumor volumes (±SD) for the entire study. Mean body weights (±SD) at termination were: 18.63±1.35, 18.93±2.21, 18.37±1.64, and 19.73±0.68 for Groups 1, 2, 4, and 5 respectively. All animals in Group 3 died by Day 4 following administration of the test article.

TABLE 31

LLC Murine Lung Cancer Model Tumor Volumes (±SD)

| | Pre-Study (pre-inoculation) | Day 1 | Day 4 | Day 6 | Day 8 |
|---|---|---|---|---|---|
| Group 1 | | | | | |
| 1 | 14.24 | 153.73 | 331.91 | 535.56 | 912.24 |
| 2 | 32.33 | 214.81 | 584.67 | 471.54 | 1279.31 |
| 3 | 59.33 | 139.34 | 473.68 | 679.81 | 1537.65 |
| Avg. | 35.30 | 169.29 | 463.42 | 562.30 | 1243.07 |
| SD | 22.69 | 40.07 | 126.69 | 106.68 | 314.28 |
| Median | 32.30 | 153.73 | 473.68 | 535.56 | 1279.30 |
| Group 2 | | | | | |
| 4 | 32.25 | 111.81 | 279.51 | 495.74 | 1397.70 |
| 5 | 26.14 | 212.63 | 191.72 | 493.23 | 1436.34 |
| 6 | 33.96 | 267.64 | 931.43 | 894.34 | 1944.96 |
| Avg. | 30.78 | 197.36 | 467.55 | 627.77 | 1593.00 |
| SD | 4.11 | 79.03 | 404.12 | 230.86 | 305.42 |
| Median | 32.35 | 212.63 | 279.51 | 495.74 | 1436.30 |

TABLE 31-continued

LLC Murine Lung Cancer Model Tumor Volumes (±SD)

|  | Pre-Study (pre-inoculation) | Day 1 | Day 4 | Day 6 | Day 8 |
|---|---|---|---|---|---|
| Group 3 | | | | | |
| 7 | 60.85 | 176.73 | | Terminated | |
| 8 | 127.74 | 261.32 | | Terminated | |
| 9 | 14.72 | 181.62 | 305.32 | Terminated | |
| Avg. | 67.77 | 206.56 | 305.32 | Terminated | |
| SD | 56.83 | 47.49 | 0.00 | Terminated | |
| Median | 60.85 | 181.62 | 305.32 | Terminated | |
| Group 4 | | | | | |
| 10 | 0.00 | 215.10 | 433.79 | 736.46 | 1482.22 |
| 11 | 51.25 | 178.90 | 253.76 | 934.53 | 1054.04 |
| 12 | 48.22 | 167.90 | 707.37 | 637.53 | 1305.12 |
| Avg. | 33.16 | 187.30 | 464.98 | 769.51 | 1280.46 |
| SD | 28.75 | 24.70 | 228.41 | 151.23 | 215.15 |
| Median | 48.22 | 178.90 | 433.79 | 736.46 | 1305.10 |
| Group 5 | | | | | |
| 13 | 48.34 | 152.22 | 357.31 | 531.79 | 1502.00 |
| 14 | 50.59 | 189.28 | 363.13 | 702.81 | 953.66 |
| 15 | 35.33 | 175.68 | 610.45 | 1072.45 | 1401.62 |
| Avg. | 44.75 | 172.39 | 443.63 | 769.02 | 1285.76 |
| SD | 8.24 | 18.75 | 144.50 | 276.34 | 291.95 |
| Median | 48.34 | 175.68 | 363.13 | 702.81 | 1401.60 |

Figure 46:
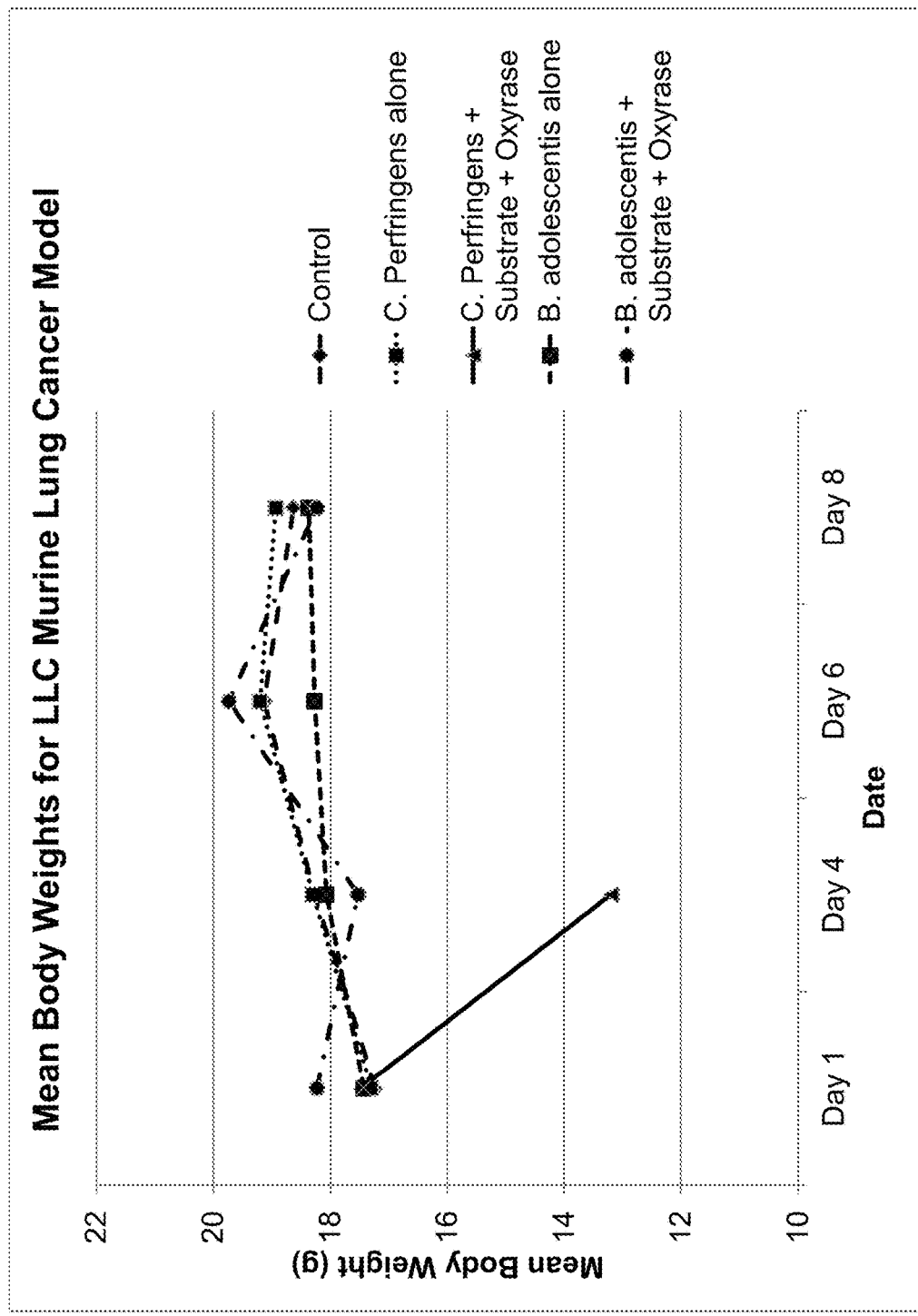
FIG. 46 is a graphical representation of the average body weights in grams±standard deviation of mice inoculated with the LLC murine lung cancer cell line and treated with one of the following: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.
Figure 47:
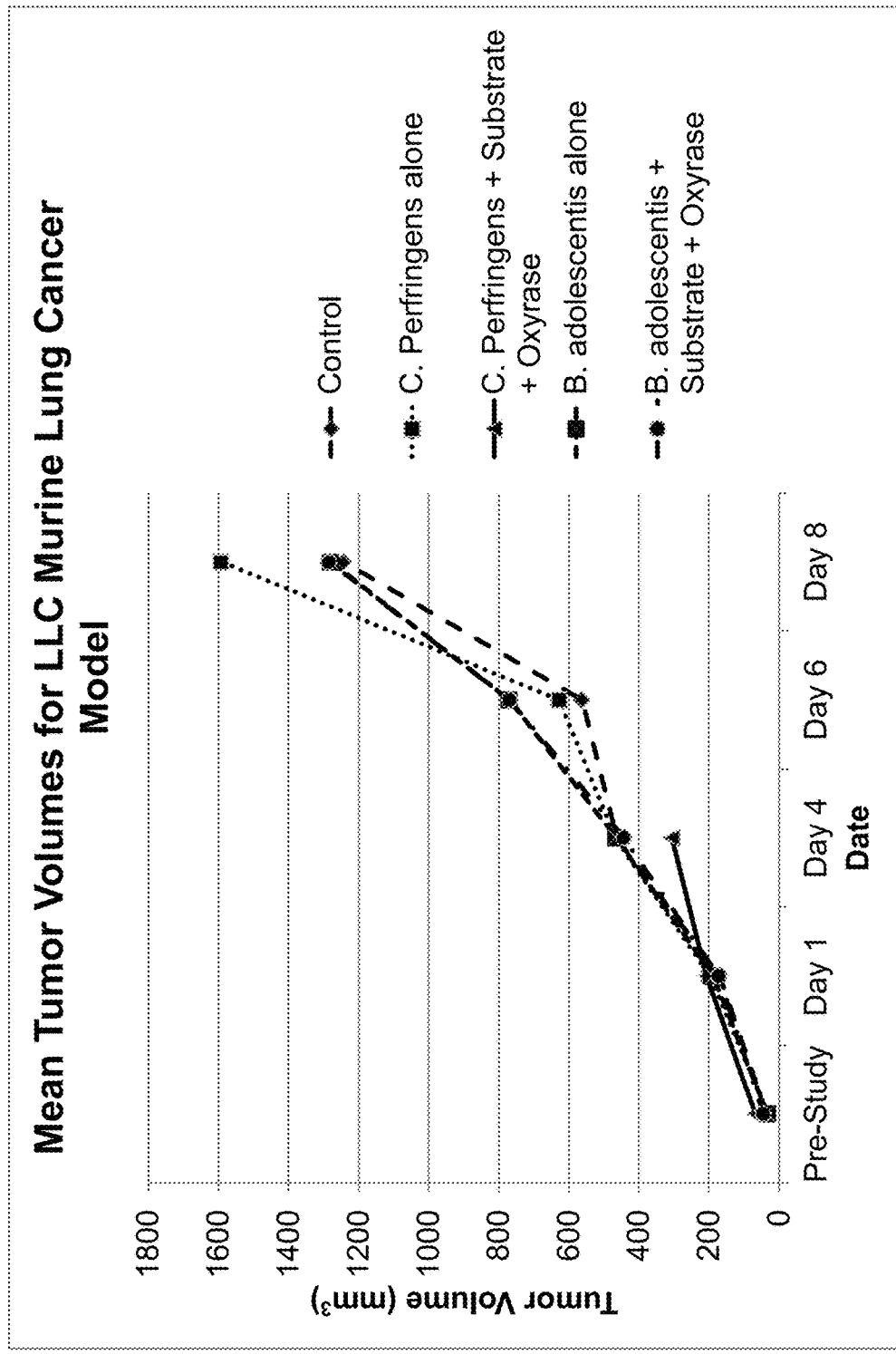
FIG. 47 is a graphical representation of the average tumor volume in $mm^3$±standard deviation of mice inoculated with the LLC murine lung cancer cell line and treated with one of the following: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.
Figure 48:
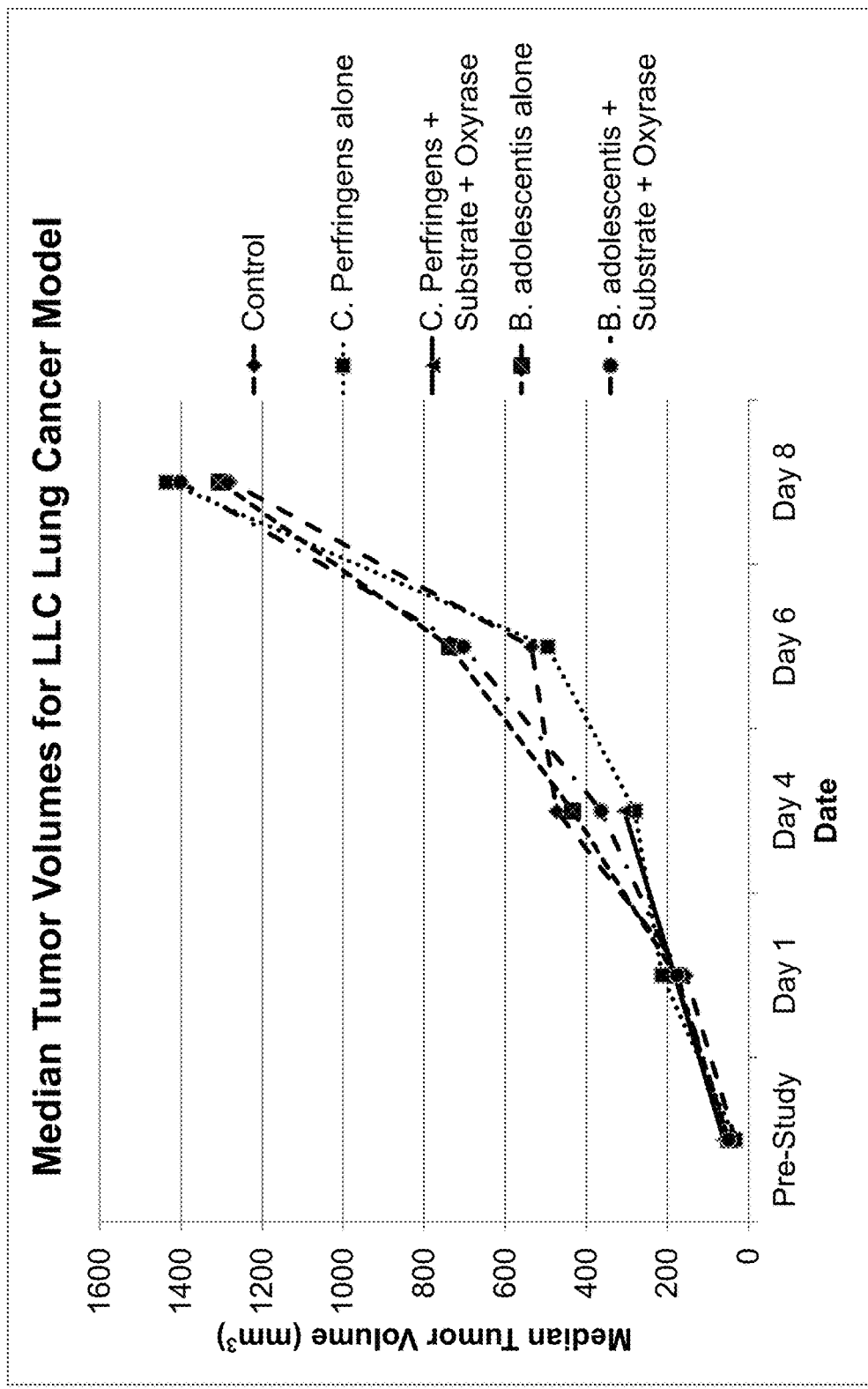
FIG. 48 is a graphical representation of the median tumor volume in $mm^3$±standard deviation of mice inoculated with the LLC murine lung cancer cell line and treated with one of the following: PBS (control); *C. perfringens* alone; *C. perfringens*, substrate, and Oxyrase®; *B. adolescentis* alone; and *B. adolescentis*, substrate, and Oxyrase®. The dates correspond to days on which measurements were taken, with 11/5 corresponding to day of inoculation with one of the five treatments.

FIG. 46 is a graphical illustration of the average body weights for the study period. FIG. 47 is a graphical illustration of the mean tumor volumes for the study period, while FIG. 48 is a graphical illustration of the median tumor volumes for the study period.

Discussion

The experimental results indicated that the inhibition of tumor cell proliferation and growth is dependent upon dosage of the Oxyrase®. More particularly, the in vitro and in vivo experiments indicated that tumor cell growth is inhibited by exposure to increasing concentrations of the Oxyrase® membrane fragments. This is seen in the change in luciferase expression of FIGS. 3-7, and in the corrected MTT assay results of FIG. 9. Oxyrase® shows activity at as little as 0.037 u/mL and has maximized activity at a concentration of 6 u/mL.

The experiments suggested that Oxyrase® decreased tumor cell viability. Supported by the results that Oxyrase® reduced the size of tumor growths, Oxyrase® may be suitable for use in cancer treatment.

The experimental results also indicated that the inhibition of tumor cell proliferation and growth is dependent upon dosage of the Oxyrase®. More particularly, the experiments indicated that tumor cell growth is inhibited by exposure to increasing concentrations of the Oxyrase® membrane fragments (i.e. tumor cell growth is dose dependent). This is seen in the changes in cell count across five distinct cell lines as shown in Tables 2-27 and FIGS. 18-42. The experiments suggested that Oxyrase® decreased tumor cell viability. Supported by the results that Oxyrase® reduced the size of tumor growths, Oxyrase® may be suitable for use in cancer treatment.

With respect to treatment of the U87 tumors, U87 was only affected by Oxyrase® under particular sets of conditions but not others. This shows that the treatment regimen needs to be optimized to gain the maximum benefit of Oxyrase®, which was not done for the above protocol. The real value of administering oxygen scavenging membrane fragments to brain tumors is likely yet to be determined.

Further experimental results as shown in Tables 28-31 and FIGS. 43-48 suggest that Oxyrase® when used in conjunction with anaerobes may suppress tumor growths. Only tumors infected with both anaerobes and Oxyrase® exhibited changes in growth. Tumors infected with only anaerobes were not affected. This is most likely due to Oxyrase® improving anaerobic infection of tumors.

It should be noted that anaerobes differed in their effects on tumors. For example, C. perfringens is a vigorous pathogen known to cause gas gangrene. When used in the third set of experiments, it killed not only the tumor but also the host animal. B. adolescentis is not a pathogen and is commonly used in yogurt. However, upon infection of tumors with Oxyrase®, B. adolescentis only affected breast tumors, which exhibited excessive growth. Therefore, animals infected with anaerobes alone did not exhibit inhibited tumor growth. These results indicate that there is an opportunity to use a wide range of either available or genetically engineered anaerobes to infect and treat tumors particularly when used with the directed administration of Oxyrase®.

In order to provide safe and efficient results, Oxyrase® dosages should be optimized. Oxyrase® could be combined with more traditional treatments, such as drug therapies or chemotherapy, to bolster its effects and create a comprehensive treatment.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method for treating a patient with a cancerous tumor, comprising:
   intratumorally administering to the patient a composition comprising a pharmaceutically effective amount of oxygen scavenging membrane fragments, wherein the oxygen scavenging membrane fragments are derived from the cytoplasmic membranes of Escherichia coli, Salmonella typhimurium, Gluconobacter oxydans, Pseudomonas aeruginosa, or Acetobacter;
   intratumorally administering to the patient a pharmaceutically effective amount of anaerobe bacteria; and,
   wherein the composition contains the oxygen scavenging membrane fragments in an amount from 0.1 unit per milliliter to 100 units per milliliter.

2. The method of claim 1, wherein the composition further comprises a hydrogen donating substance.

3. The method of claim 2, wherein the hydrogen donating substance is lactic acid, succinic acid, alpha-glycerol phosphate, formic acid, malic acid, or a salt thereof.

4. The method of claim 1, wherein the composition is in the form of an injection, solution, suspension, or emulsion.

5. The method of claim 1, wherein the composition contains the oxygen scavenging membrane fragments in an amount from 1 unit per milliliter to 10 units per milliliter.

6. The method of claim 1, wherein the tumor is a breast, cervical, colon, liver, lung, ovarian, pancreatic, prostate, brain, or bone cancer tumor.

7. The method of claim 1, wherein the composition is administered in combination with chemotherapy, immunotherapy, radiation therapy, drug therapy, or cell transplantation.

8. The method of claim 1, wherein the administration of the composition creates localized hypoxia.

9. The method of claim 1, wherein the anaerobe bacteria are present in the composition in an amount of about $10^6$ to about $10^8$ CFU/mL.

10. The method of claim 1, wherein the anaerobe bacteria is *Bacteroides fragilis, Bifidobacterium adolescentis, Clostridium perfringens, Fusobacterium nucleatum, Porphyromonas levii, Peptostreptococcus anaerobius, Prevotella melaninogenica*, or a combination thereof.

11. The method of claim 1,
wherein the anaerobe bacteria is *Bacteroides fragilis, Bifidobacterium adolescentis, Clostridium perfringens, Fusobacterium nucleatum, Porphyromonas levii, Peptostreptococcus anaerobius, Prevotella melaninogenica*, or a combination thereof.

12. The method of claim 1, wherein the composition further comprises an anti-angiogenic agent.

13. A method for treating a tumor, comprising:
intratumorally administering a composition comprising a pharmaceutically effective amount of oxygen scavenging membrane fragments, wherein the oxygen scavenging membrane fragments are derived from the cytoplasmic membranes of *Escherichia coli, Salmonella typhimurium, Gluconobacter oxydons, Pseudomonas aeruginosa*, or *Acetobacter;*
intratumorally administering a pharmaceutically effective amount of anaerobe bacteria, wherein the anaerobe bacteria is *Bacteroides fragilis, Bifidobacterium adolescentis, Clostridium perfringens, Fusobacterium nucleatum, Porphyromonas levii, Peptostreptococcus anaerobius, Prevotella melaninogenica*, or a combination thereof; and,
wherein the composition contains the oxygen scavenging membrane fragments in an amount from 0.1 unit per milliliter to 100 units per milliliter.

14. A therapeutic composition for treating a cancer tumor, comprising:
a pharmaceutically effective amount of oxygen scavenging membrane fragments and a pharmaceutically effective amount of anaerobe bacteria,
wherein the oxygen scavenging membrane fragments are derived from the cytoplasmic membranes of *Escherichia coli, Salmonella typhimurium, Gluconobacter oxydans, Pseudomonas aeruginoso*, or *Acetobacter;*
wherein the anaerobe bacteria is *Bacteroides fragilis, Bifidobacterium adolescentis, Clostridium perfringens, Fusobacterium nucleatum, Porphyromonas levii, Peptostreptococcus anaerobius, Prevotella melaninogenica*, or a combination thereof; and, wherein the composition contains the oxygen scavenging membrane fragments in an amount from 0.1 unit per milliliter to 100 units per milliliter.

15. The composition of claim 14, wherein the composition further comprises a hydrogen donating substance.

16. The composition of claim 15, wherein the hydrogen donating substance is lactic acid, succinic acid, alpha-glycerol phosphate, formic acid, malic acid, or a salt thereof.

17. The composition of claim 14, wherein the composition contains the oxygen scavenging membrane fragments in an amount from 1 unit per milliliter to 10 units per milliliter.

18. The composition of claim 14, further comprising an anti-angiogenic agent.

* * * * *